(12) United States Patent
Zahn et al.

(10) Patent No.: US 9,085,781 B2
(45) Date of Patent: Jul. 21, 2015

(54) ACETATE RESISTANCE IN YEAST BASED ON INTRODUCTION OF A MUTANT HAA1 ALLELE

(71) Applicant: Edeniq, Inc., Visalia, CA (US)

(72) Inventors: Kenneth Zahn, Visalia, CA (US); Sandra Jacobson, Three Rivers, CA (US)

(73) Assignee: Edeniq, Inc., Visalia, CA (US)

( * ) Notice: Subject to any disclaimer, the term of this patent is extended or adjusted under 35 U.S.C. 154(b) by 172 days.

(21) Appl. No.: 13/947,338

(22) Filed: Jul. 22, 2013

(65) Prior Publication Data

US 2014/0024095 A1 Jan. 23, 2014

Related U.S. Application Data

(60) Provisional application No. 61/674,676, filed on Jul. 23, 2012.

(51) Int. Cl.
C12P 7/06 (2006.01)
C12N 15/81 (2006.01)
C12P 7/10 (2006.01)
C07K 14/395 (2006.01)
C12N 1/22 (2006.01)

(52) U.S. Cl.
CPC .............. C12P 7/06 (2013.01); C07K 14/395 (2013.01); C12N 1/22 (2013.01); C12N 15/81 (2013.01); C12P 7/10 (2013.01); Y02E 50/16 (2013.01); Y02E 50/17 (2013.01)

(58) Field of Classification Search
CPC ................................ C12P 7/06; C12N 15/81
USPC ...................... 435/161, 252.3, 256.23, 320.1
See application file for complete search history.

(56) References Cited

U.S. PATENT DOCUMENTS

| 2010/0311137 A1 | 12/2010 | Brown et al. |
| 2011/0159560 A1 | 6/2011 | Donaldson et al. |
| 2012/0009640 A1 | 1/2012 | Behrouzian et al. |
| 2012/0184020 A1 | 7/2012 | Picataggio et al. |

FOREIGN PATENT DOCUMENTS

| WO | 99/51746 A1 | 10/1999 |
| WO | 2009-126795 A2 | 10/2009 |
| WO | 2011-031319 A2 | 3/2011 |
| WO | 2011/140386 A2 | 11/2011 |

OTHER PUBLICATIONS

International Search Report and Written Opinion mailed on Nov. 26, 2013 for International Patent Application No. PCT/US2013/51500, filed Jul. 22, 2013, 11 pages.
H0H2A2, UniProtKB Accession No. H0H2A2_9SACH, Feb. 22, 2012 [on line] [Retrieved on Nov. 9, 2013] http://uniprot.org/uniprot/H0H2A2.txt?version=4.
Cliften et al., Finding functional features in Saccaromyces genomes by phylogenetic footprinting, Science, 2003, vol. 301, No. 5629, pp. 71-76.
Alper et al., "Engineering Yeast Transcription Machinery for Improved Ethanol Tolerance and Production"; 2006; Science, vol. 314, pp. 1565-1568.
Fernandes et al., "Saccharomyces cerevisiae adaptation to weak acids involves the transcription factor Haa1p and Haa1p-regulated genes"; 2005; Biochemical Biophysical Research Communications; vol. 337; pp. 95-103.
Mira et al., "Genomic Expression Program Involving the Haa1p-Regulon in Saccharomyces cerevisiae Response to Acetic Acid"; OMICS, vol. 14, No. 5, pp. 587-601.
Mira et al., "Adaptive Response and Tolerance to Weak Acids in Saccharomyces cerevisiae: A Genome-W ide View"; 2010; OMICS, vol. 14, No. 5, pp. 525-540.
Mira et al., "Identification of a DNA-binding site for the transcription factor Haa1, required for Saccharomyces cerevisiae response to acetic acid stress"; 2011; Nucleic Acid Research, pp. 1-12.
Mollapour et al., "Hog1 Mitogen-Activated Protein Kinase Targets the Yeast FPS1 Aquaglyceroporin for Endocytosis, Thereby Rendering Cells Resistant to Acetic Acid"; 2007; Mol. Cell Biol., vol. 27, No. 18, pp. 6446-6456.
Mumberg et al., "Yeast vectors for the controlled expression of heterologous proteins in different backgrounds"; 1995, Gene, vol. 156, pp. 119-122.

Primary Examiner — Tekchand Saidha
(74) Attorney, Agent, or Firm — Kilpatrick Townsend & Stockton LLP

(57) ABSTRACT

Improved haa1 transcriptional regulatory proteins, polynucleotides encoding improved haa1 transcriptional regulatory proteins and vectors and cells thereof are provided, as well as methods for converting a cellulose-containing biomass feedstock to ethanol using improved haa1 transcriptional regulatory proteins and cells expressing heterologous haa1 transcriptional regulatory proteins as disclosed herein.

20 Claims, 13 Drawing Sheets p416 tef transformation vs p416 tef haa1 mutant library-TR3 acetate plates

Conversion of Acetate concentrations (A)

Summary of sequence changes in haa1 mut2 and haa1 mut40

| Haa1 mut2 | Haa1 mut40 |
|---|---|
| 440 F->Y | 508 D->Y |
| 518 P->S | 510 N->K |
| 591 I->V | 527 A->V |
| 605 H->Y | FS@553 |
| 622 S->F | 554 N->I |
| 639 S->F | Trunc@554 |
| 673 S->L | |

Fermentation of pretreated saccharified sugar cane bagasse by wild type strain TR3 or the improved mutant strain TR3 haa1 mut2

ACETATE RESISTANCE IN YEAST BASED ON INTRODUCTION OF A MUTANT HAA1 ALLELE

CROSS-REFERENCE TO RELATED PATENT APPLICATIONS

The present patent application claims benefit of priority to U.S. Patent Application No. 61/674,676, filed Jul. 23, 2012, which is incorporated by reference herein in its entirety.

BACKGROUND OF THE INVENTION

Acetate inhibition is a well-recognized impediment to the efficient fermentation of most types of biomass, particularly those with high hemicellulose contents. The release of acetic acid during the acid, heat and pressure-induced breakdown of hemicellulose is known to produce levels of acetic acid which can exceed 1%, a level which is highly inhibitory (in terms of growth, viability and/or performance of desired metabolic function e.g. fermentation of sugars) to most microorganisms. Solutions to the problem include efforts to block the initial release by altering the pretreatment conditions, removal of acetate by chemical or physical methods and genetic improvement of the fermentation organisms to utilize or better tolerate acetate.

BRIEF SUMMARY OF THE INVENTION

In some embodiments, isolated polynucleotides are provided. In some embodiments, the isolated polynucleotide encodes a transcription factor polypeptide comprising an amino acid sequence that:
a. is substantially identical (e.g., at least 60, 70, 80, 90, 95, 97, 98, or 99%) to amino acids 1-554 of SEQ ID NO:2; and
b. comprises at least one amino acid difference compared to SEQ ID NO:2 selected from the group consisting of F440Y, P518S, D508Y, N510K, A527V, I591V, H605Y, S622F, S639F, and S673L.

In some embodiments, the transcription factor polypeptide binds to SEQ ID NO:16.

In some embodiments, the amino acid sequence is at least 80% identical to SEQ ID NO:2. In some embodiments, the amino acid sequence comprises the following amino acid differences compared to SEQ ID NO:2: F440Y, P518S, I591V, H605Y, S622F, S639F, and S673L.

In some embodiments, the polypeptide has fewer than 600 (e.g., fewer than 590, 580, 570, 560, 550) amino acids.

In some embodiments, the amino acid sequence comprises the following amino acid differences compared to SEQ ID NO:2: D508Y, N510K, and A527V.

In some embodiments, the amino acid sequence comprises at least two (e.g., 2, 3, 4, 5, 6, 7, or more) amino acid differences compared to SEQ ID NO:2 selected from the group consisting of F440Y, P518S, D508Y, N510K, A527V, I591V, H605Y, S622F, S639F, and S673L.

In some embodiments, an expression cassette is provided. In some embodiments, the expression cassette comprises a heterologous promoter operably linked to the polynucleotide as described above or elsewhere herein.

In some embodiments, the promoter is heterologous to the polynucleotide.

In some embodiments, a yeast cell, or a culture comprising the yeast cell, is provided. In some embodiments, the yeast cell comprises an expression cassette as described above or elsewhere herein, wherein the yeast cell ferments sugar in the presence of acetate better than a control yeast cell lacking the expression cassette.

In some embodiments, the yeast cell is a *Saccharomyces cervisiae* or *Pichia stipitis* cell. In some embodiments, the yeast cell lacks a wild type allele of HAA1. In some embodiments, the yeast cell comprises a genomically-integrated mutant haa1 allele replacing the wild type HAA1 allele. In some embodiments, the yeast cell comprises a mutant haa1 allele on a heterologous plasmid, wherein the cell also comprises a genomic wild type allele of HAA1.

In some embodiments, the yeast cell exhibits better fermentation compared to a control yeast strain in the presence of greater than 0.5% w/v acetate. In some embodiments, the yeast cell exhibits better fermentation compared to a control yeast strain in the presence of greater than 0.8% w/v acetate. In some embodiments, the yeast cell exhibits better fermentation compared to a control strain in the presence of greater than 0.5% w/v acetic acid. In some embodiments, the yeast cell exhibits better fermentation compared to a control yeast strain in the presence of greater than 0.8% w/v acetic acid. In some embodiments, the yeast cell exhibits better fermentation compared to a control yeast strain in the presence of at least 0.5% w/v acetate or at least 0.8% w/v acetate. In some embodiments, the yeast cell exhibits better fermentation compared to a control strain in the presence of at least 0.5% w/v acetic acid or at least 0.8% w/v acetic acid. In some embodiments, the yeast cell exhibits better fermentation compared to a control yeast strain in the presence of about 0.5% w/v to about 2.0% w/v acetate, or about 0.5% w/v to about 1.0% w/v acetate, or about 0.5% to about 0.8% acetate. In some embodiments, the yeast cell exhibits better fermentation compared to a control yeast strain in the presence of at least 0.5%, 0.6%, 0.7%, 0.8%, 0.9%, 1.0%, or 1.5% acetate, or about 2.0% w/v acetate. Thus, in some embodiments, the yeast cell exhibits better fermentation compared to a control yeast strain in the presence of at least 0.5% to at least 1.0% w/v acetic acid, at least 0.8% to at least 1.5% w/v acetic acid, or at least 1.0% to about 2.0% w/v acetate. In some embodiments, the yeast cell exhibits better fermentation compared to a control yeast strain in the presence of about 0.5% w/v to about 2.0% w/v acetic acid, or about 0.5% w/v to about 1.0% w/v acetic acid, or about 0.5% to about 0.8% acetic acid. In some embodiments, the yeast cell exhibits better fermentation compared to a control yeast strain in the presence of at least 0.5%, 0.6%, 0.7%, 0.8%, 0.9%, 1.0%, or 1.5% acetic acid, or about 2.0% w/v acetic acid. Thus, in some embodiments, the yeast cell exhibits better fermentation compared to a control yeast strain in the presence of at least 0.5% to at least 1.0% w/v acetic acid, at least 0.8% to at least 1.5% w/v acetic acid, or at least 1.0% to about 2.0% w/v acetic acid.

In some embodiments, better fermentation is caused by expression of the improved Haa1 proteins resulting in increased growth of the microorganism relative to a control or reference microorganism in a specified time under specified conditions.

In some embodiments, better fermentation is caused by expression of the improved Haa1 proteins resulting in increased rate (e.g., kinetics) of formation of fermentation product or increased titer of fermentation product by a microorganism relative to a control or reference microorganism in a specified time under specified conditions.

In some embodiments, better fermentation is caused by expression of the improved Haa1 proteins resulting in increased tolerance of a microorganism to higher acetic acid levels relative to a control or reference microorganism in a specified time under specified conditions.

In some embodiments, better fermentation is caused by expression of the improved Haa1 proteins resulting in increased tolerance of a microorganism to higher acetate levels relative to a control or reference microorganism in a specified time under specified conditions.

In some embodiments, better fermentation is caused by expression of the improved Haa1 proteins resulting in decreased concentration of fermentable carbohydrates during fermentation relative to a control or reference microorganism in a specified time under specified conditions.

In some embodiments, methods of making ethanol from sugar are provided. In some embodiments, the method comprises contacting the yeast as described above or elsewhere herein to a solution comprising sugar under conditions to allow for fermentation of the sugar into ethanol; and recovering the ethanol.

In some embodiments, the solution comprises sufficient furfural to inhibit fermentation of a control yeast lacking the expression cassette. In some embodiments, the sugars are generated by cellulosic enzymes.

Also provided are aqueous mixtures comprising sugars, acetic acid and/or acetate and the yeast cell as described above or elsewhere herein. In some embodiments, the mixture comprises at least 0.5% or 0.8% w/v acetic acid or acetate. In some embodiments, the mixture comprises cellulose-containing biomass.

Also provided herein are engineered microorganisms with enhanced tolerance to acetic acid or its cognate base acetate, containing an improved Haa1 protein. The improved Haa1 protein is encoded by an HAA1 open reading frame containing one or more mutations conferring its improved characteristic. In some embodiments, microorganisms containing the improved haa1 gene either alone or in combination with the wild type copy of HAA1 have an increased fermentation of sugars to a desired product relative to the natural strain. In some embodiments, microorganisms containing the improved haa1 gene have increased fermentation in cellulosic sugar material derived from pretreated and saccharified biomass. In some embodiments, the desired fermentation product is ethanol.

Provided herein, inter alia, are improved Haa1 proteins substantially identical (e.g., at least 70%, 75%, 80%, 85%, 90%, 91%, 92%, 93%, 94%, 95%, 96%, 97%, 98%, 99%) to SEQ ID NO:2 and having improved acetate resistance compared to a control Haa1 protein comprising SEQ ID NO:2. In some embodiments, the improved Haa1 proteins are substantially identical (e.g., at least 70%, 75%, 80%, 85%, 90%, 91%, 92%, 93%, 94%, 95%, 96%, 97%, 98%, 99%) to SEQ ID NO:3 and have Haa1 protein activity conferring increased acetate tolerance compared to a control Haa1 protein comprising SEQ ID NO:2. In some embodiments, the improved Haa1 proteins are substantially identical (e.g., at least 70%, 75%, 80%, 85%, 90%, 91%, 92%, 93%, 94%, 95%, 96%, 97%, 98%, 99%) to SEQ ID NO:4 and have Haa1 protein activity conferring increased acetate tolerance compared to a control haa1 protein comprising SEQ ID NO:2. In some embodiments, the improved Haa1 proteins are substantially identical (e.g., at least 70%, 75%, 80%, 85%, 90%, 91%, 92%, 93%, 94%, 95%, 96%, 97%, 98%, 99%) to any of SEQ ID NO:5 through SEQ ID NO:15 and have improved Haa1 protein activity conferring increased acetate tolerance compared to a control Haa1 protein comprising SEQ ID NO:2.

In some embodiments, the improved Haa1 protein comprises one or more mutations at a position corresponding to a position selected from the group consisting of (a) position 440 of SEQ ID NO:2, having an amino acid other than F; (b) position 518 of SEQ ID NO:2 having an amino acid other than P; (c) position 508 of SEQ ID NO:2 having an amino acid other than D; (d) position 510 of SEQ ID NO:2 having an amino acid other than N; (e) position 527 of SEQ ID NO:2 having an amino acid other than A; (f) position 591 of SEQ ID NO:2 having an amino acid other than I; (g) position 605 of SEQ ID NO:2 having an amino acid other than H; (h) position 622 of SEQ ID NO:2 having an amino acid other than S; (i) position 639 of SEQ ID NO:2 having an amino acid other than S; (j) position 673 of SEQ ID NO:2 having an amino acid other than S and (k) position 554 of SEQ ID NO:2 having an amino acid other than N.

In some embodiments, the improved Haa1 protein is encoded by a mutant haa1 gene designated haa1 mut2 and contains seven mutations in the HAA1 coding region as put forth in SEQ ID NO:3. In some embodiments, haa1 mut2 gene is expressed from a plasmid in a yeast cell containing a wild type HAA1 allele. In some embodiments, the haa1 mut2 gene is integrated into the HAM genomic locus and replaces the wild type gene function.

In some embodiments, the improved Haa1 protein is expressed in the presence of a genomic wild type copy of HAA1 and is encoded by a mutant haa1 gene designated haa1 mut40 expressed from a heterologous plasmid construct that contains four mutations plus a C-terminal haa1 truncation. This truncated protein is caused by a nucleotide deletion and projected frameshift in the mutant haa1 allele, causing the translation product to go out of frame and become truncated after amino acid 554.

In another aspect, provided herein are polynucleotides comprising a nucleic acid encoding the improved Haa1 protein provided herein. In some embodiments, the polynucleotide comprises an expression cassette comprising a heterologous promoter operably linked to the nucleic acid. Also provided herein are vectors comprising the polynucleotides provided herein, and isolated cells or culture of cells comprising the heterologous polynucleotides provided herein. In some embodiments, the cell is a yeast cell. In some embodiments, the cell is a *Saccharomyces cerevisiae*.

In another aspect, provided herein are methods for growing cells in the presence of medium containing increasing amounts of acetate and monitoring cell growth. In some embodiments, the cells are yeast cells. In some embodiments, the methods comprise growing the cells expressing an improved Haa1 protein as described herein (e.g., comprising one or more mutations at a position corresponding to a position selected from the group consisting of (a) position 440 of SEQ ID NO:2, having an amino acid other than F; (b) position 518 of SEQ ID NO:2 having an amino acid other than P; (c) position 508 of SEQ ID NO:2 having an amino acid other than D; (d) position 510 of SEQ ID NO:2 having an amino acid other than N; (e) position 527 of SEQ ID NO:2 having an amino acid other than A; (f) position 591 of SEQ ID NO:2 having an amino acid other than I; (g) position 605 of SEQ ID NO:2 having an amino acid other than H; (h) position 622 of SEQ ID NO:2 having an amino acid other than S; (i) position 639 of SEQ ID NO:2 having an amino acid other than S; (j) position 673 of SEQ ID NO:2 having an amino acid other than S and (k) position 554 of SEQ ID NO:2 having an amino acid other than N).

In some embodiments, the cells ferment carbohydrates in the presence of acetic acid levels higher than tolerable for the natural strain. In some embodiments, the cells ferment carbohydrates in the presence of acetate levels toxic for the natural parental yeast strain. In some embodiments the cells are yeast cells.

In some embodiments, the cells ferment carbohydrates in a cellulosic sugar solution derived from pretreated biomass that has been saccharified. In some embodiments, this saccharification has been performed by cellulosic enzyme mixtures. In some embodiments, this saccharification has been performed by cells expressing cellulosic enzymes. In some embodiments, this saccharification has been performed by cells expressing cellulosic enzymes and the improved haa1 protein.

In some embodiments, the method comprises treating the pretreated biomass with a cell or culture of cells that express the improved Haa1 protein. In some embodiments, the cell is a *Saccharomyces cerevisiae*.

In some embodiments, the cellulose-containing biomass feedstock is a woody material. In some embodiments, the woody material is cellulosic or lignocellulosic plant material selected from the group consisting of orchard prunings, chaparral, mill waste, urban wood waste, municipal waste, logging waste, forest thinnings, short-rotation woody crops, and industrial waste. In some embodiments, the cellulose-containing biomass feedstock is a non-woody material. In some embodiments, the non-woody material is selected from the group consisting of gramineous agricultural residue, wheat straw, oat straw, rice straw, barley straw, rye straw, flax straw, sugar cane, bagasse, corn stover, corn stalks, corn cobs, corn husks, prairie grass, switchgrass, gamagrass, foxtail, sugar beet pulp, citrus fruit pulp, seed hulls, cellulosic animal wastes, lawn clippings, seaweed, bagasse, energy cane, and giant reed. In some embodiments, the cellulose-containing biomass feedstock is corn grain, barley grain, milo grain, wheat grain or rice grain.

The range shown is 0-300 mM or 0-1.5% w/v.

Figure 4:
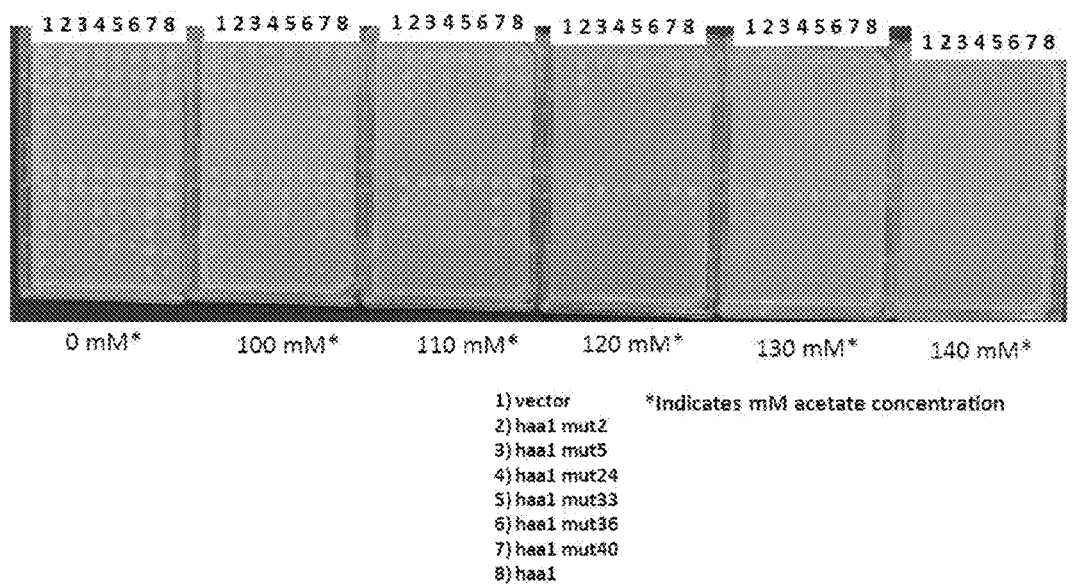

FIG. 4. Screening for acetate resistance among candidates containing plasmid-borne haa1 alleles.

Colony growth plating assay of candidates containing plasmids bearing different haa1 alleles is shown. From left to right, an increasing amount of acetate is applied in the plates which all contain a synthetic defined media of CSM (complete supplement mixture) with glucose and lacking uracil. Medium lacking uracil is used to provide selection for the URA3 marked plasmid. Acetate concentrations are shown at the bottom of the panel; 0 mM, 100 mM, 120 mM, 130 mM, 140 mM. Candidate strains are spotted in ten-fold dilutions from top-to-bottom in each set of plates. Two sets of equivalent dilutions are spotted in each plate as duplicate platings to evaluate phenotypic reproducibility. Strains plated in the experiment are indicated a number at the top of each dilution series and by the legend on the bottom; 1 and 8 are plasmid vector and wild type HAA1 plasmid clone controls, respectively, 2-7 are independent candidates containing different cloned haa1 alleles. Plates were incubated for eight days to produce the result shown.

Figure 5:
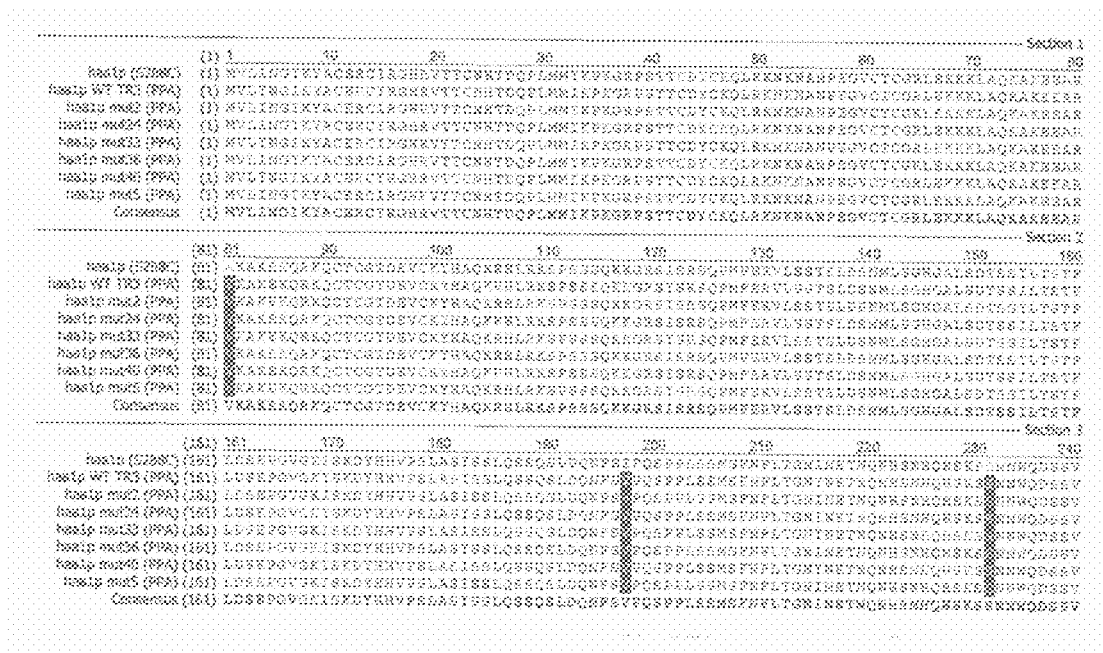
Figure 5:
Figure 5:
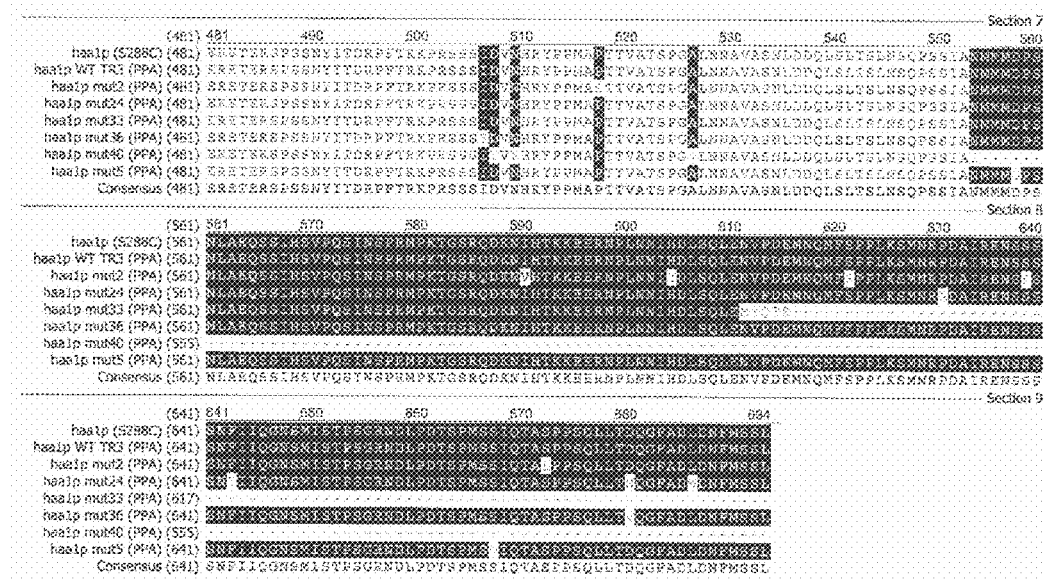

FIG. 5. Sequence illustration of six site-directed acetate resistant mutants in the carboxyl terminus of the HAA1 gene (HAA1 gene sequence from Wild type (WT) S288C=SEQ ID NO:1; WT TR3=SEQ ID NO:2; mut2=SEQ ID NO:3; mut24=SEQ ID NO:17; mut33=SEQ ID NO:18; mut36=SEQ ID NO:19; mut40=SEQ ID NO:4; mut5=SEQ ID NO:20; consensus=SEQ ID NO:21). FIG. 5A: alignment of Haa1 partial polypeptide comprising amino acids 1-240; FIG. 5B: alignment of Haa1 partial polypeptide comprising amino acids 241-480; FIG. 5C: alignment of Haa1 partial polypeptide comprising amino acids 481-694.

Protein sequences of six acetate resistant mutants culled from the original set of 40 isolates recovered from an acid gradient plate are shown. The DNA sequence of each mutant was determined and conceptual translation of the DNA sequence was used to obtain the amino acid sequence. Alignment of all of the amino acid sequences was carried out using the Clustal program. The entire amino acid sequence of the Haa1 protein is shown. The top line displays the sequence of the non-mutant Haa1 protein determined from yeast strain S288C, in which the genome sequence has been entirely determined. Below this the sequence of the wild type HAA1 gene from strain TR3, the strain employed in these studies, is presented. Numbering indicates the amino acid position and blocks of black lettering on white background indicate entirely conserved sequences. In addition beyond position 553, blocks of white lettering on black background show entirely conserved amino acids in all sequences. Dashed lines indicate the extent of deletions in two of the sequences. Grey shading of the amino acid coding letter indicates amino acid positions that have amino acid substitutions which are not conserved. Black shading of the amino acid coding indicates amino acid positions that have amino acid substitutions which are conserved.

FIG. 6. Summary of amino acid changes in the two of the most highly acetate resistant haa1 mutants Sequence differences of haa1 mutants 2 and 40 from the wild type sequence are indicated. Amino acid abbreviations are shown below:

| | | | | |
|---|---|---|---|---|
| F—phenylalanine | Y—tyrosine | P—proline | S—serine | I—isoleucine |
| V—valine | H—histidine | L—leucine | D—glutamic acid | |
| K—lysine | A—alanine | | | |
| FS—indicates a frameshift mutation | | | | |
| Trunc—indicates the point of premature protein termination | | | | |

Figure 7:
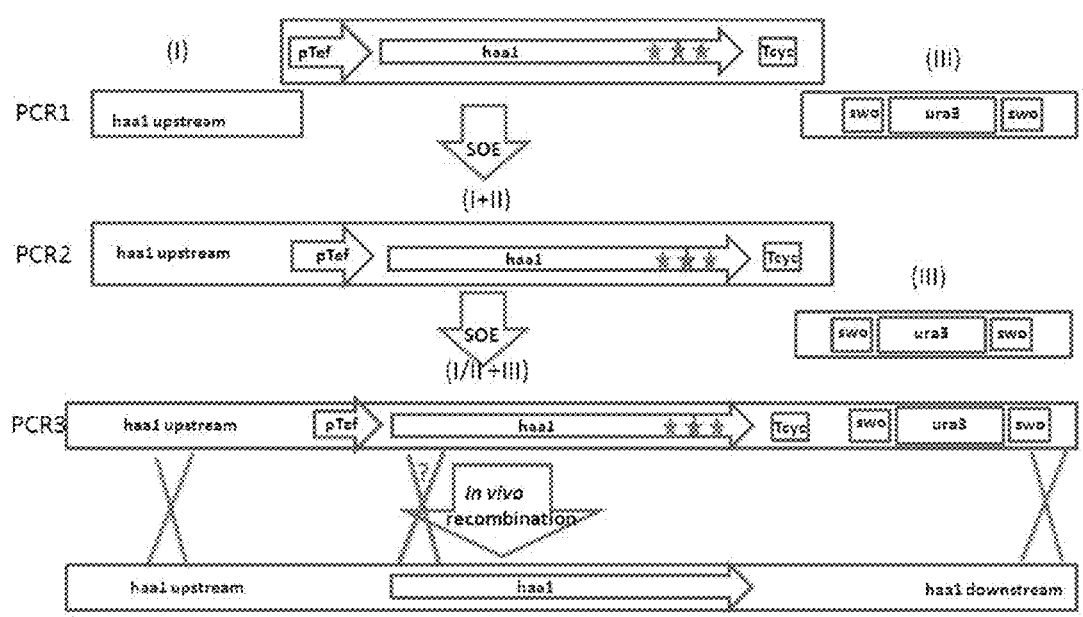

FIG. 7. Schematic representation of the procedure used to integrate haa1 alleles into the chromosome of *Saccharomyces cerevisiae* strain TR3

In the top portion (PCR 1), three PCR fragments were synthesized independently; from left, a ~1000 bp piece (I) to provide homology to the region upstream of HAA1, an ~3 kB piece containing the haa1 gene including heterologous Tef promoter and cyc1 terminator (II), a 1.5 kB piece encompassing the URA3 gene and two identical flanking swo segments (III). In PCR 2, fragments 1+II are recombined in vitro using overlap extension PCR (SOE) based on homology between the primers at the 3' end of the haa1 upstream and the 5' end of the pTef promoter piece. In PCR 3, the recombined haa1 upstream/pTef-haa1-cyc1 fragment is recombined in vitro with the downstream ura3 piece to produce a 5.5 kB fragment bearing a selectable marker. The 5.5 kB fragment was then purified and used for transformation of *S. cerevisiae* strain TR3. Two possible crossover sites are shown in the lower portion; the left side crossover results in insertion of the Tef promoter into the chromosome whereas the right side crossover results in recombination within the HAA1 open reading frame and retains the endogenous HAA1 promoter.

Figure 8:
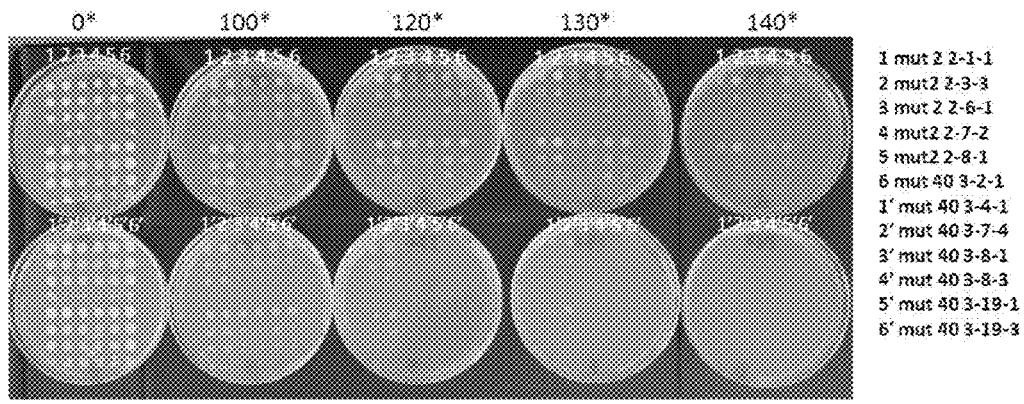

FIG. 8. Screening for acetate resistance among candidates with chromosomally inserted haa1 alleles.

Colony growth plating assay of candidates containing chromosomal insertions of haa1 mut2 or mut40 alleles is shown. From left to right, an increasing amount of acetate is applied in the plates which all contain a base media of CSM glucose. Acetate concentrations are shown at the top of the panel; 100 mM, 120 mM, 130 mM, 140 mM. Candidate strains are spotted in ten-fold dilutions from top-to-bottom in each set of plates. Two sets of equivalent dilutions are spotted in each plate. Strains plated in the experiment are indicated with a number at the top of each dilution series and by the legend on the right side; 1-5 are independent candidates containing haa1 mut2 allele insertions, 6 and 1'-6' are independent clones containing haa1 mut40 allele insertions. Plates were incubated for four days to produce the result shown.

Figure 9:
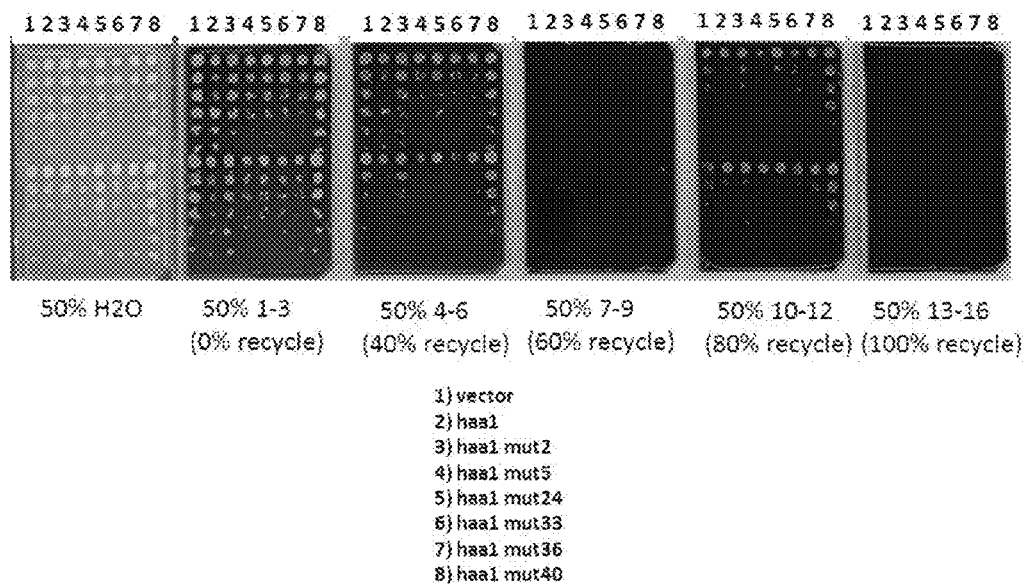

FIG. 9. Screening for resistance to biomass among candidates containing plasmid-borne haa1 alleles.

Colony growth plating assay of candidates containing plasmids bearing different haa1 alleles is shown. Every plate has one half volume substituted by either $H_2O$ (the leftmost plate) or a saccharified pretreated biomass sample prepared by a different pretreatment (the right five plates). All plates were prepared with CSM glucose media lacking uracil. From left to right, 50% of a 0%, 40%, 60% or 80% "recycle HPHT" mixture respectively was added to the plates. "Recycle HPHT" is defined as biomass that has been pretreated by EdeniQ proprietary thermomechanical means, saccharified by cellulosic enzymes, glucose fermented into ethanol by EdeniQ proprietary yeast, centrifuged to recover the supernatant used for diluting fresh biomass to a particular % solids and subjecting it to the same form of pretreatment and saccharification. Candidate strains are spotted in ten-fold dilutions from top-to-bottom in each set of plates. Two sets of equivalent dilutions are spotted in each plate. Strains plated in the experiment are indicated a number at the top of each dilution series and by the legend on the bottom. 1 and 2 are plasmid vector and wild type HAA1 plasmid clone controls, 3-8 are independent candidates containing different cloned haa1 alleles. Plates were incubated for eight days to produce the result shown.

Figure 10:
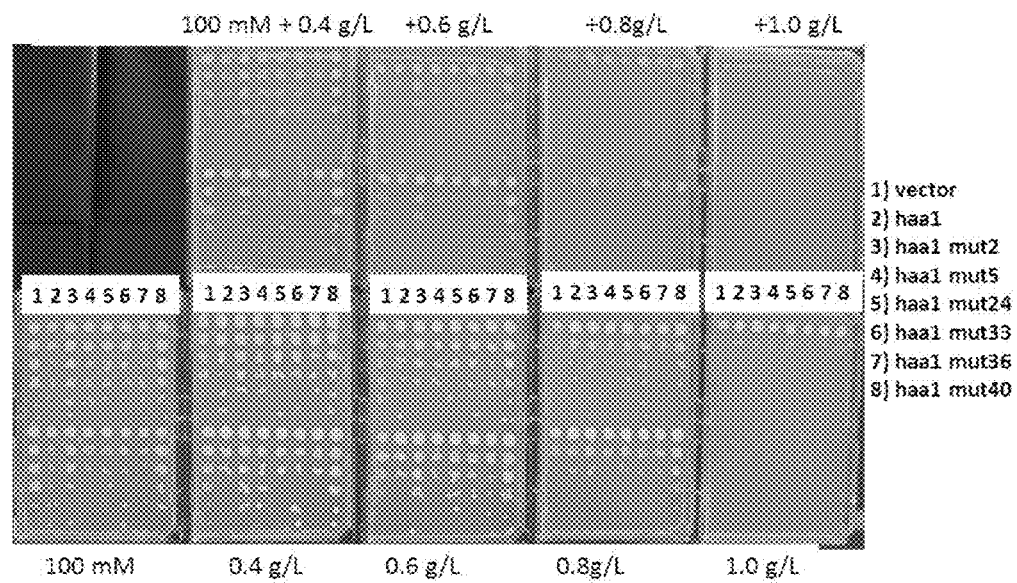

FIG. 10. Screening for furfural resistance and/or furfural plus acetate resistance among candidates containing plasmid-borne haa1 alleles.

Spot testing of candidates containing plasmids bearing different haa1 alleles is shown. From left to right, an increasing amount of furfural was added into the solid medium plates. All plates contain a base media of CSM glucose lacking uracil or the same media plus 100 mM acetate. The plate on the lower left has only 100 mM acetate added. In all other plates furfural concentrations are shown at the top and bottom of the panel; 0.4 g/L, 0.6 g/L, 0.8 g/L and 1.0 g/L. In addition to varying furfural, the upper set of plates contains acetate at 100 mM. Candidate strains are spotted in ten-fold dilutions from top to bottom in each set of plates. Strains plated in the experiment are indicated as a number at the top of each dilution series and by the legend on the right. 1 and 2 are plasmid vector and wild type Haa1 protein plasmid clone controls, 3-8 are independent candidates containing different cloned haa1 alleles. Plates were incubated for eight days to produce the result shown.

Figure 11:
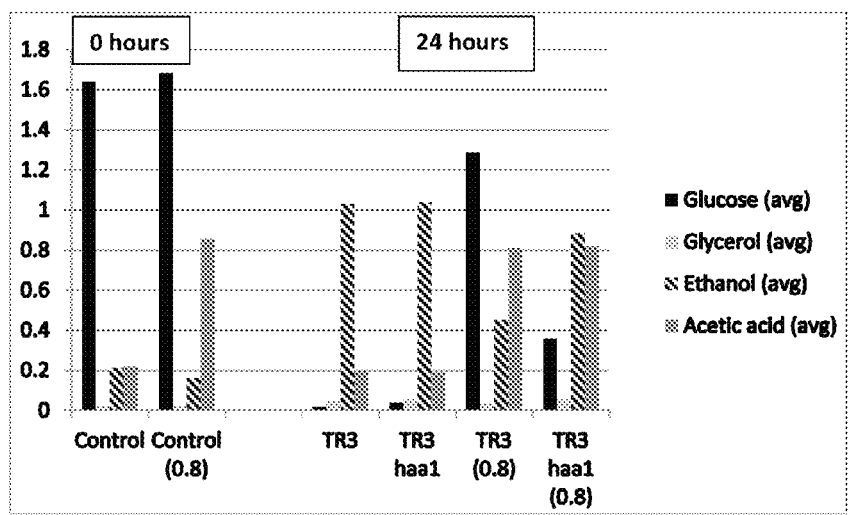

FIG. 11. Fermentation of Sugar Cane Bagasse Biomass by the wild type strain TR3 or the TR3 haa1 mut2 mutant strain improved for acetate resistance.

Graphical representation of the levels of key metabolites present in pretreated saccharified sugarcane bagasse during biomass fermentation by wild type control and the improved haa1 mut2 yeast strains. Metabolite levels of glucose, glycerol, ethanol and acetate are shown (% w/v) on the Y-axis at T=0 (control, control (0.8)) or after 24 hours of fermentation by strains TR3, TR3 haa1, TR3(0.8), TR3 haa1 (0.8) to the right along the X-axis where (0.8) indicates addition of acetate to greater than 0.8% w/v and haa1 indicates the chromosomally integrated copy of the haa1 mut2 allele. Note that two control conditions are used, differing only by the addition of acetate to greater than 0.8% w/v. All determinations were by HPLC measurement. Control samples were run in duplicate; experimental samples were run in triplicate.

DEFINITIONS

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "isolated," when applied to a protein or nucleic acid, denotes that the protein or nucleic acid, respectively, is essentially free of other cellular components with which it is associated in the natural state. It is preferably in a substantially homogeneous state, and for example, can be in either a dry or aqueous solution. Purity and homogeneity are typically determined using analytical chemistry techniques such as polyacrylamide gel electrophoresis or high performance liquid chromatography.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same. The term "substantially identical" refers to two or more sequences or subsequences that have a specified percentage of amino acid residues or nucleotides that are the same (i.e., at least about 40% identity, 45%, 50%, 55%, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see e.g., NCBI web site http://www.ncbi.nlm.nih.gov/BLAST/ or the like). The definition includes sequences that have deletions and/or additions, as well as those that have substitutions. As described below, algorithms can account for gaps and the like. When not specified, identity or substantial identity is determined over the entire length of the reference sequence. When specified, identity can be determined over a region that is at least about 10 amino acids or nucleotides in length, at least about 25 amino acids or nucleotides in length, or over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An exemplary algorithm suitable for determining percent sequence identity and sequence similarity is BLAST 2.0 algorithm, which is described in Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

To determine which amino acid of a first protein "corresponds" to the position of an amino acid in a second protein, the amino acid sequences of the two proteins are optimally aligned (e.g., using a BLAST algorithm). This is particularly useful, for example, where two proteins have high homology but where one protein contains one or more insertions or deletions relative to the second protein. In such cases, for example, position 57 of a first protein may align with position 51 in a second protein when the two proteins are optimally aligned. Thus position 51 of the second protein "corresponds" to position 57 of the first protein.

A "heterologous sequence," "heterologous polypeptide," or a "heterologous nucleic acid", as used herein, is one that originates from a source foreign to the particular host cell, or, if from the same source, is modified from its original form. Thus, a heterologous expression cassette in a cell is an expression cassette that is not endogenous to the particular host cell, for example by being linked to nucleotide sequences from an expression vector rather than chromosomal DNA or by being linked to a heterologous promoter or by being linked to a reporter gene, etc.

"Expression cassette" refers to a polynucleotide comprising a promoter or other regulatory sequence operably linked to a sequence encoding a protein.

"Acetic Acid" also known as ethanoic acid is an organic compound with the chemical formula $CH_3COOH$. The hydrogen center in the carboxyl group (—COOH) in carboxylic acids such as acetic acid can separate from the molecule by ionization: $CH_3CO_2H \rightarrow CH_3CO_2^- + H^+$ Because of this release of the proton ($H^+$), acetic acid has acidic character. Acetic acid is a weak monoprotic acid. In aqueous solution, it has a pKa value of 4.75. Its conjugate base is acetate ($CH_3COO^-$).

"Acetate" is a derivative of acetic acid which can occur in the form of salts or esters. The acetate anion $[CH_3COO]^-$, is one of the carboxylate family. It is the conjugate base of acetic acid. Above a pH of 5.5, acetic acid converts to acetate: $CH_3COOH \leftrightarrows CH_3COO^- + H^+$. Many acetate salts are ionic consistent with their tendency to dissolve in water. Acetate is a common anion in biology. It is mainly utilized by organisms in the form of acetyl coenzyme A.

"Furfural" is defined as a heterocyclic aldehyde with a chemical formula of $OC_4H_3CHO$. It is formed from plant material containing the polysaccharide hemicellulose when reacted with dilute acid and/or heat whereby hemicellulose undergoes hydrolysis to yield xylose which can be subjected to a dehydration reaction forming furfural.

"Pretreatment" is defined as a physical means of reducing the recalcitrance of lignocellulosic biomass such that the plant cell walls are less resistant to deconstruction.

"Biomass" is defined as biological material from living or recently living organisms.

"Lignocellulosic biomass" is defined as biological material of plants that is comprised in part of lignin, hemicellulose and cellulose.

The term "cellulose-containing biomass feedstock" is defined herein to mean any cellulosic or lignocellulosic plant material, waste material, including but not limited to, leaves and stalks of both woody and non-woody plants. The term "woody" is used herein both in the botanical sense to mean "comprising wood"; that is, composed of extensive xylem tissue as found in trees and shrubs, and also in the sense of "being woodlike". Accordingly, "nonwoody" refers to materials lacking these characteristics. Cellulose-containing biomass feedstock includes, but is not limited to, crops such as starch crops (e.g., corn, wheat, rice or barley), sugar crops (e.g., sugarcane, energy cane or sugarbeet), forage crops (e.g., grasses, alfalfa, or clover), and oilseed crops (e.g., soybean, sunflower, or safflower); wood products such as trees, shrubs, and wood residues (e.g., sawdust, bark or the like from forest clearings and mills); waste products such as municipal solid waste (MSW; e.g., paper, food and yard wastes or wood), and process waste; and aquatic plants such as algae, water weed, water hyacinth, or reed and rushes.

In some embodiments, cellulose-containing biomass feedstock from woody plants can include orchard prunings, chaparral, mill waste (such as bark, chips, shavings, sawdust, and the like), urban wood waste (such as discarded lumber, wood pallets, crates, tree and brush trimmings, etc.), municipal waste (such as newspaper and discarded grocery produce), logging waste and forest thinnings (tree tops, limbs and cull material), short-rotation woody crops such as poplar and cottonwood, and industrial waste (such as wood pulp sludge).

The preponderance of biomass from non-woody plants in agriculture is derived from monocotyledonous plants, and especially grassy species belonging to the family Gramineae. Of primary interest are gramineous agricultural residues; that is, the portion of grain-bearing plants that remain after harvesting the seed. Illustrative of such residues, without limitation thereto, are wheat straw, oat straw, rice straw, barley straw, rye straw, flax straw, sugar cane, corn stover, corn stalks, corn cobs, corn husks, and the like. Also included within this definition are grasses not conventionally cultivated for agricultural purposes, such as prairie grasses (e.g.

big bluestem, little bluestem, Indian grass), switchgrass, gamagrass, and foxtail. In some embodiments, the agricultural biomass comprises corn kernel, barley kernel, milo kernel, wheat kernel or rice kernel.

Byproducts of agriculture industrial process can have high amounts of acetic acid, furfural and 5-HMF that can inhibit growth and/or fermentation of microorganisms.

Other agricultural byproducts in the category of biomass include waste streams components from commercial processing of crop materials (such as sugar beet pulp, citrus fruit pulp, sugarcane bagasse, seed hulls, and the like), cellulosic animal wastes, lawn clippings, seaweed, etc. In some embodiments, the biomass is distillers grains.

Any of the aforementioned biomass materials would be utilized as substrates for fermentative conversion to ethanol.

"Biomass derived intermediate" refers to a carbohydrate or non-sugar intermediate derived from biomass deconstruction.

"Hemicellulose" refers to any of several branched heteropolymers including arabinoxylans present along with cellulose in most plant cell walls. Hemicellulose has a random amorphous structure that is easily hydrolyzed by dilute acid or base or hemicellulose enzymes to liberate xylose and other carbohydrates.

"Xylan" refers to a variety of complex polysaccharides found in plant cell walls consisting of xylose.

"Cellulose" refers to a polysaccharide consisting of a linear chain of beta 1-4 linked D glucose units.

"Cellulosic enzymes" or "cellulase" refers to proteins that catalyze the hydrolysis of cellulose.

"Saccharified" means release of carbohydrates such as glucose and xylose from pretreated biomass using chemical or biological methods, including enzymatic digestion. Cellulosic enzymes commonly used for saccharification of pretreated biomass include, but are not limited to lignin peroxidases, cellobiohydrolases, endoglucanases, beta-glucosidases and xylanases. Cellulosic enzyme mixtures may be a mixture of any of the above enzymes and can be derived from organisms naturally expressing the enzymes or from organisms expressing these enzymes as heterologous proteins.

"Control cell" refers to a cell that expresses an unmodified form of the Haa1 protein. In some embodiments, the control cell expresses an unmodified form of the Haa1 protein from the endogenous chromosomal gene locus. In some embodiments, the control cell contains an expression cassette or vector that does not encode an Haa1 protein.

DETAILED DESCRIPTION OF THE INVENTION

Improved Haa1 Transcription Factor Proteins

As shown in the Examples, a series of amino acid changes have been introduced in the yeast gene HAA1 and have been shown to improve tolerance to acetic acid of yeast strains carrying the mutations. Thus, the improved Haa1 proteins described herein, wherein expressed in a microorganism (e.g., yeast), increase the amount of microorganism growth relative to a control or reference microorganism in a specified time under specified conditions. In some embodiments, the improved Haa1 proteins described herein increase the rate (e.g., kinetics) of fermentation or increase the titer of fermentation product performed by a microorganism relative to a control or reference Haa1 protein in a specified time under specified conditions. In some embodiments, the improved Haa1 proteins enable the microorganisms to tolerate higher acetic acid levels in the medium relative to a control or reference microorganism. In some embodiments, the improved Haa1 proteins enable the microorganisms to tolerate higher acetate levels in the medium relative to a control or reference microorganism. In some embodiments, the improved Haa1 proteins enable the microorganisms to decrease the concentration of fermentable carbohydrates during fermentation. In some embodiments, the carbohydrates fermented are polysaccharides from cellulose and/or hemicellulose. In some embodiments, the carbohydrates measured are fermentable sugars. In some embodiments, the conditions are those specified in the examples.

In some embodiments, there is greater than 50% increase in titer of fermentation product performed by the haa1 mutant strain compared to a control strain under conditions of greater than 0.5% acetate under specified time and conditions.

In some embodiments, there is greater than 50% increase in titer of fermentation product performed by the haa1 mutant strain compared to a control strain under conditions of greater than 0.8% acetic acid under specified time and conditions.

In some embodiments, the cell comprising a mutant haa1 allele described herein has improved acetate resistance compared to a control yeast cell. For example, in some embodiments, the cell comprising a mutant haa1 allele described herein has increased resistance to solutions or biomass containing 0.01%, 0.05%, 0.1%, 0.2%, 0.3%, 0.4%, 0.5%, 0.6%, 0.7%, or 0.8% more w/v acetate as compared to a control cell. In some embodiments, the cell comprising a mutant haa1 allele described herein has improved acetic acid resistance compared to a control yeast cell. For example, in some embodiments, the cell comprising a mutant haa1 allele described herein has increased resistance to solutions or biomass containing 0.01%, 0.05%, 0.1%, 0.2%, 0.3%, 0.4%, 0.5%, 0.6%, 0.7%, or 0.8% more w/v acetic acid as compared to a control cell. In some embodiments, the increased resistance to acetate and/or acetic acid is determined by measuring the growth of the cell in solutions or biomass containing acetate and/or acetic acid. In some embodiments, the increased resistance to acetate and/or acetic acid is determined by measuring the rate of formation of a fermentation product or titer of a fermentation product in solutions or biomass containing acetate and/or acetic acid. In some embodiments, the cell is a yeast cell.

In some embodiments, an increase in the amount of fermented carbohydrate can be determined by measuring the amount of desired product produced from fermenting the biomass hydrolysate under specified conditions. For example, in some embodiments, the carbohydrate is derived from glucan, xylan, or another fermentable sugar polysaccharide. In some embodiments, the carbohydrate is a sugar biomass-derived intermediate. In some embodiments, the downstream product is a non-sugar biomass-derived intermediate. In some embodiments, the conditions are those specified in the examples.

The improved or unmodified Haa1 protein control preparations provided herein can be of any origin, e.g., they can be from bacteria, yeast, fungus or other organisms. In some embodiments, the Haa1 proteins are yeast proteins. In some embodiments, the Haa1 proteins are Haa1 protein variants having at least 70%, 75%, 80%, 85%, 90%, 91%, 92%, 93%, 94%, 95%, 96%, 97%, 98%, 99%, or higher sequence identity to a yeast Haa1 protein, e.g., a Haa1 protein of SEQ ID NOS:1-15 (e.g., SEQ ID NOS:1, 2, 3, 4, 5, 6, 7, 8, 9, 10, 11, 12, 13, 14, 15) and in some embodiments contain one or more of the mutations described herein.

Accordingly, in some embodiments, the unmodified form of the Haa1 protein is a wild-type or a naturally occurring Haa1 protein, such as, for example, a yeast Haa1 protein. In some embodiments, a control yeast is a yeast that expresses an unmodified form of the Haa1 protein. In some embodiments, the control yeast expresses an unmodified form of the Haa1 protein from the endogenous chromosomal gene locus. In some embodiments, the control yeast contains an expression cassette or vector that does not encode an Haa1 protein.

The improved Haa1 proteins provided herein comprise one or more amino acid substitutions relative to the unmodified Haa1 protein. In some embodiments, the amino acid substitution(s) comprise at least an amino acid substitution at a position corresponding to a position selected from the group consisting of (a) position 440 of SEQ ID NO:2, having an amino acid other than F; (b) position 518 of SEQ ID NO:2 having an amino acid other than P; (c) position 508 of SEQ ID NO:2 having an amino acid other than D; (d) position 510 of SEQ ID NO:2 having an amino acid other than N; (e) position 527 of SEQ ID NO:2 having an amino acid other than A; (f) position 591 of SEQ ID NO:2 having an amino acid other than I; (g) position 605 of SEQ ID NO:2 having an amino acid other than H; (h) position 622 of SEQ ID NO:2 having an amino acid other than S; (i) position 639 of SEQ ID NO:2 having an amino acid other than S; (j) position 673 of SEQ ID NO:2 having an amino acid other than S and (k) position 554 of SEQ ID NO:2 having an amino acid other than N.

In some embodiments, the improved Haa1 protein is a mutant Haa1 protein comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to SEQ ID NO:1 or 2 and having improved Haa1 protein activity compared with a control Haa1 protein of SEQ ID NO: 2 wherein the amino acid of the mutant Haa1 protein corresponding to position 440 is Phenylalanine (F) substituted with Tyrosine (Y); position 518 is Proline (P) substituted with Serine (S); position 591 is Isoleucine (I) substituted with Valine (V); position 605 is Histidine (H) substituted with Tyrosine (Y); position 622 is Serine (S) substituted with Phenylalanine (F); position 639 is Serine (S) substituted with Phenylalanine (F); and position 673 is Serine (S) substituted with Leucine (L).

In some embodiments, the improved Haa1 protein is a mutant Haa1 protein comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NO:4 and having improved Haa1 protein activity compared with a control Haa1 protein of SEQ ID NO: 2 wherein the amino acid of the mutant Haa1 protein corresponding to position 508 is Aspartic Acid (D) substituted with tyrosine (Y); position 510 is Asparagine (N) substituted with Lysine (K); position 527 is alanine (A) substituted with Valine (V); position 553 has a single base pair insertion in the codon resulting in frameshift here and asparagine (N) substitution with isoleucine (I); additionally resulting in premature translational termination after position 554 and truncation of the haa1 protein.

In some embodiments, the improved Haa1 protein is a mutant Haa1 protein comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS:1, 2, 3, 4, 5, 6, 7, 8, 9, 10, 11, 12, 13, 14, 15 and having improved Haa1 protein activity compared with a control Haa1 protein of SEQ ID NO: 2.

Further provided herein are improved Haa1 proteins having improved Haa1 activity compared to a control Haa1 protein (e.g., a Haa1 protein comprising SEQ ID NO:1). In some embodiments, the improved Haa1 protein is a mutant Haa1 protein substantially identical to SEQ ID NO:2 and improved acetic acid tolerance compared to a strain containing a control Haa1 protein (e.g., a Haa1 protein comprising SEQ ID NO:1 or SEQ ID NO:2).

In some embodiments, the amino acid of the mutant Haa1 protein corresponding to position 440 of SEQ ID NO:2 is any amino acid other than F, and the control Haa1 protein has the same amino acid sequence as the mutant Haa1 protein except that the amino acid of the control Haa1 protein corresponding to position 440 of SEQ ID NO:2 is F. In some embodiments, the amino acid of the mutant Haa1 protein corresponding to position 440 of SEQ ID NO:2 is Tyrosine (Y), for example, as set forth in SEQ ID NO:5.

In some embodiments, the amino acid of the mutant Haa1 protein corresponding to position 508 of SEQ ID NO:2 is any amino acid other than D, and the control Haa1 protein has the same amino acid sequence as the mutant Haa1 protein except that the amino acid of the control Haa1 protein corresponding to position 508 of SEQ ID NO:2 is D. In some embodiments, the amino acid of the mutant Haa1 protein corresponding to position 508 of SEQ ID NO:2 is Tyrosine (Y), for example, as set forth in SEQ ID NO:6. In some embodiments, the mutant Haa1 protein having a substitution at the position corresponding to position 508 of SEQ ID NO:2 further comprises a C-terminal deletion. In one embodiment, the C-terminal deletion begins at the position corresponding to amino acid 555 of SEQ ID NO:2. In some embodiments, the mutant Haa1 protein having a substitution at the position corresponding to position 508 of SEQ ID NO:2 comprises a deletion of amino acids corresponding to positions 555-694 of SEQ ID NO:2.

In some embodiments, the amino acid of the mutant Haa1 protein corresponding to position 510 of SEQ ID NO:2 is any amino acid other than N, and the control Haa1 protein has the same amino acid sequence as the mutant Haa1 protein except that the amino acid of the control Haa1 protein corresponding to position 510 of SEQ ID NO:2 is N. In some embodiments, the amino acid of the mutant Haa1 protein corresponding to position 510 of SEQ ID NO:2 is Lysine (K), for example, as set forth in SEQ ID NO:7. In some embodiments, the mutant Haa1 protein having a substitution at the position corresponding to position 510 of SEQ ID NO:2 further comprises a C-terminal deletion. In one embodiment, the C-terminal deletion begins at the position corresponding to amino acid 555 of SEQ ID NO:2. In some embodiments, the mutant Haa1 protein having a substitution at the position corresponding to position 510 of SEQ ID NO:2 comprises a deletion of amino acids corresponding to positions 555-694 of SEQ ID NO:2.

In some embodiments, the amino acid of the mutant Haa1 protein corresponding to position 518 of SEQ ID NO:2 is any amino acid other than P, and the control Haa1 protein has the same amino acid sequence as the mutant Haa1 protein except that the amino acid of the control Haa1 protein corresponding to position 510 of SEQ ID NO:2 is P. In some embodiments, the amino acid of the mutant Haa1 protein corresponding to position 518 of SEQ ID NO:2 is Serine (S), for example, as set forth in SEQ ID NO:8.

In some embodiments, the amino acid of the mutant Haa1 protein corresponding to position 527 of SEQ ID NO:2 is any amino acid other than A, and the control Haa1 protein has the same amino acid sequence as the mutant Haa1 protein except that the amino acid of the control Haa1 protein corresponding to position 527 of SEQ ID NO:2 is A. In some embodiments, the amino acid of the mutant Haa1 protein corresponding to position 527 of SEQ ID NO:2 is Valine (V), for example, as set forth in SEQ ID NO:9. In some embodiments, the mutant Haa1 protein having a substitution at the position corresponding to position 527 of SEQ ID NO:2 further comprises a C-terminal deletion. In one embodiment, the C-terminal deletion begins at the position corresponding to amino acid 555 of SEQ ID NO:2. In some embodiments, the mutant Haa1 protein having a substitution at the position corresponding to position 527 of SEQ ID NO:2 comprises a deletion of amino acids corresponding to positions 555-694 of SEQ ID NO:2.

In some embodiments, the amino acid of the mutant Haa1 protein corresponding to position 554 of SEQ ID NO:2 is any amino acid other than N, and the control Haa1 protein has the same amino acid sequence as the mutant Haa1 protein except that the amino acid of the control Haa1 protein corresponding to position 554 of SEQ ID NO:2 is N. In some embodiments, the amino acid of the mutant Haa1 protein corresponding to position 554 of SEQ ID NO:2 is Isoleucine (I), for example, as set forth in SEQ ID NO:10. In some embodiments, the mutant Haa1 protein having a substitution at the position corresponding to position 554 of SEQ ID NO:2 further comprises a C-terminal deletion. In one embodiment, the C-terminal deletion begins at the position corresponding to amino acid 555 of SEQ ID NO:2. In some embodiments, the mutant Haa1 protein having a substitution at the position corresponding to position 554 of SEQ ID NO:2 comprises a deletion of amino acids corresponding to positions 555-694 of SEQ ID NO:2.

In some embodiments, the amino acid of the mutant Haa1 protein corresponding to position 591 of SEQ ID NO:2 is any amino acid other than I, and the control Haa1 protein has the same amino acid sequence as the mutant Haa1 protein except that the amino acid of the control Haa1 protein corresponding to position 510 of SEQ ID NO:2 is I. In some embodiments, the amino acid of the mutant Haa1 protein corresponding to position 591 of SEQ ID NO:2 is Valine (V), for example, as set forth in SEQ ID NO:11.

In some embodiments, the amino acid of the mutant Haa1 protein corresponding to position 605 of SEQ ID NO:2 is any amino acid other than H, and the control Haa1 protein has the same amino acid sequence as the mutant Haa1 protein except that the amino acid of the control Haa1 protein corresponding to position 605 of SEQ ID NO:2 is H. In some embodiments, the amino acid of the mutant Haa1 protein corresponding to position 605 of SEQ ID NO:2 is Tyrosine (Y), for example, as set forth in SEQ ID NO:12.

In some embodiments, the amino acid of the mutant Haa1 protein corresponding to position 622 of SEQ ID NO:2 is any amino acid other than S, and the control Haa1 protein has the same amino acid sequence as the mutant Haa1 protein except that the amino acid of the control Haa1 protein corresponding to position 510 of SEQ ID NO:2 is S. In some embodiments, the amino acid of the mutant Haa1 protein corresponding to position 622 of SEQ ID NO:2 is Phenylalanine (F), for example, as set forth in SEQ ID NO:13.

In some embodiments, the amino acid of the mutant Haa1 protein corresponding to position 639 of SEQ ID NO:2 is any amino acid other than S, and the control Haa1 protein has the same amino acid sequence as the mutant Haa1 protein except that the amino acid of the control Haa1 protein corresponding to position 639 of SEQ ID NO:2 is S. In some embodiments, the amino acid of the mutant Haa1 protein corresponding to position 639 of SEQ ID NO:2 is Phenylalanine (F), for example, as set forth in SEQ ID NO:14.

In some embodiments, the amino acid of the mutant Haa1 protein corresponding to position 673 of SEQ ID NO:2 is any amino acid other than S, and the control Haa1 protein has the same amino acid sequence as the mutant Haa1 protein except that the amino acid of the control Haa1 protein corresponding to position 673 of SEQ ID NO:2 is S. In some embodiments, the amino acid of the mutant Haa1 protein corresponding to position 673 of SEQ ID NO:2 is Leucine (L), for example, as set forth in SEQ ID NO:15.

In some embodiments, the mutant Haa1 protein comprises one, two, three, four, five, or more mutations as described herein. For example, in some embodiments, the mutant Haa1 protein is substantially identical to SEQ ID NO:2 and comprises one, two, three, four, five, six, or seven, or more mutations selected from the group consisting of mutations at a position corresponding to a position selected from the group consisting of (a) position 440 of SEQ ID NO:2, having an amino acid other than F; (b) position 518 of SEQ ID NO:2 having an amino acid other than P; (c) position 591 of SEQ ID NO:2 having an amino acid other than I; (d) position 605 of SEQ ID NO:2 having an amino acid other than H; (e) position 622 of SEQ ID NO:2 having an amino acid other than S; (f) position 639 of SEQ ID NO:2 having an amino acid other than S; and (g) position 673 of SEQ ID NO:2 having an amino acid other than S.

In some embodiments, the mutant Haa1 protein comprises one, two, three, four, five, or more mutations as described herein. In some embodiments, the mutant Haa1 protein has a C-terminal truncation starting at the amino acid corresponding to position 554 of SEQ ID NO:2. For example, in some embodiments, the mutant Haa1 protein is substantially identical to amino acids 1-554 of SEQ ID NO:2 and comprises one, two, three, four, or more mutations selected from the group consisting of mutations at a position corresponding to a position selected from the group consisting of (a) position 508 of SEQ ID NO:2, having an amino acid other than D; (b) position 510 of SEQ ID NO:2 having an amino acid other than N; (c) position 527 of SEQ ID NO:2 having an amino acid other than A; (d) position 554 of SEQ ID NO:2 having an amino acid other than N; (e) position 555 containing a stop mutation due to translational frameshift due to upstream nucleotide insertion.

Wildtype Haa1 protein has been reported to be a transcription factor that binds to SEQ ID NO:16 in promoter sequences (e.g., the ACRE region of the TPO3 promoter). See, e.g., Mira, N. P., *Nuc. Acids Res.* 1-12 (2011). Without intending to limit the scope of the invention, it is believed that improved haa1 mutant proteins described herein also bind to SEQ ID NO:16 in promoter sequences, thereby regulating transcription. Promoter binding assays are described in, e.g., Mira, N. P., *Nuc. Acids Res.* 1-12 (2011), and can be used to measure protein binding to DNA sequences.

The improved Haa1 protein discussed herein may be recombinantly expressed by molecular cloning into an expression vector containing a suitable promoter and other appropriate transcription regulatory elements, and transferred into prokaryotic or eukaryotic host cells to produce recombinant enzymes. Techniques for such manipulations are fully described by Sambrook et al. (Molecular Cloning: A Laboratory Manual; Cold Spring Harbor Laboratory, Cold Spring Harbor, N.Y., (1989); Current Protocols in Molecular Biology, Ausubel et al., Green Pub. Associates and Wiley-Interscience, New York (1988); Yeast Genetics: A Laboratory Course Manual, Rose et al., Cold Spring Harbor Laboratory, Cold Spring Harbor, N.Y., (1990)).

A variety of techniques are available and known to those skilled in the art for introduction of nucleic acid constructs into a cellular host. Transformation of microbial cells may be accomplished through, e.g., use of polyethylene glycol, calcium chloride, viral infection, DEAE dextran, phage infection, electroporation and other methods known in the art. Transformation of fungus, in particular *Pichia*, may be accomplished, for example, according to "*Pichia* Protocols", in *Methods Mol. Biol.*, Higgins, David R. and Cregg, James M.; Eds. (Humana, Totowa, N.J.) (1998). Introduction of the recombinant vector into yeasts can be accomplished by methods including electroporation, use of spheroplasts, lithium acetate, and the like.

Polynucleotides comprising a nucleic acid encoding the improved Haa1 protein are also provided. In some embodiments, the polynucleotide comprises an expression cassette comprising a heterologous promoter operably linked to the nucleic acid. Also provided herein are vectors comprising the polynucleotides provided herein, and isolated cells or culture of cells comprising the polynucleotides that is heterologous to the cell. In some embodiments, the cell is a bacteria or yeast cell. In some embodiments, the cell is a *Saccharomyces cerevisiae*.

8. Yeasts

In some embodiments, the improved Haa1 proteins or other enzymes discussed herein are heterologously expressed in one or more yeast strain. Any yeast strain can be used according to the present invention. Yeast are unicellular microorganisms that belong to one of three classes: Ascomycetes, Basidiomycetes and Fungi Imperfecti. While pathogenic yeast strains, or nonpathogenic mutants thereof, can be used in accordance with the present invention, nonpathogenic yeast strains will generally be used. Exemplary genera of yeast strains include *Saccharomyces, Candida, Cryptococcus, Hansenula, Kluyveromyces, Pichia, Rhodotorula, Schizosaccharomyces* and *Yarrowia*. Exemplary species of yeast strains include *Saccharomyces cerevisiae, Saccharomyces carlsbergensis, Candida albicans, Candida kefyr, Candida tropicalis, Candida intermedia, Cryptococcus laurentii, Cryptococcus neoformans, Hansenula anomala, Hansenula polymorphs, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are meant to be included within the aforementioned species. In some embodiments, a yeast strain capable of replicating plasmids to a particularly high copy number is used. In some embodiments, a temperature-tolerant yeast strain is used. In some embodiments, an inhibitor-tolerant yeast strain is used.

The present invention provides for yeast strains that express the improved Haa1 protein discussed herein. Yeast expressing the improved Haa1 protein discussed herein can be generated as is known in the art. For example, expression cassettes comprising a promoter operably linked to a coding sequence for the improved Haa1 protein discussed herein can be (optionally inserted into a nucleic acid vector and) introduced into the yeast. A number of expression vectors for various yeast species are known in the art and some can be obtained commercially. Vectors can optionally include an origin of replication and/or a marker gene for identifying cells transformed with the vector. In some embodiments, the expression cassettes are stably introduced into a yeast chromosome or extrachromosomal DNA.

Any number of promoters can be used to drive expression from the expression cassettes of the invention. Exemplary promoters include, e.g., constitutive or inducible promoters. Recombinant gene expression can be driven by promoters including, but not limited to, the yeast GAL10 gene promoter, the phosphoglycerate kinase (PGK) promoter (see, e.g., Tuite, M. F. et. al. (1982) *EMBO Journal* 1, 603-608; WO 84/04757), GAL10/PGK promoter chimeras (see, e.g., U.S. Pat. No. 5,739,007) or other yeast promoters such as alcohol dehydrogenase (see, e.g., Bennetzen, J. L. and Hall, B. D. *J. Biol. Chem.* 257:3018 (1982); Ammerer, G. in *Methods in Enzymology* Vol. 101, p. 192 (1983)) phosphoglycerate kinase (see, e.g., Derynck, R., Hitzemann, R. A., Gray, P. W., Goeddel, D. V., in *Experimental Manipulation of Gene Expression*, 1983, p. 247, ed. M. Inouye, Academic Press), triose phosphate isomerase (see, e.g., Alber, T. and Kawasaki, G., *J. Molec and Applied Genet.* 1: 419-434 (1982)), or enolase (see, e.g., Innes, M. A. et al. *Science* 226:21 (1985)) can be used in a similar manner.

Expression vectors used in yeast cells can also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

9. Method for Converting a Cellulose-containing Biomass Feedstock to Ethanol

In some embodiments, the pretreated and saccharified cellulosic biomass feedstock is added directly to cells containing the mutant Haa1 protein provided herein to form an aqueous mixture and incubated under conditions to allow for efficient fermentation of cellulosic sugars to ethanol or other products. Accordingly, provided herein are methods for converting cellulosic sugars derived from biomass feedstocks into ethanol. In some embodiments, the cellulose-containing biomass feedstock is corn grain or corn stover. In some embodiments, the cellulose-containing biomass feedstock is sugarcane bagasse.

In some embodiments, the cellulose-containing biomass feedstock is contacted with a cell expressing an improved Haa1 protein. The heterologous Haa1 protein-expressing cell can be any cell known in the art, including bacteria, yeast, or other cells.

In some embodiments, the cellulose-containing biomass feedstock is first pre-treated to render the cellulose more available to the enzymes. In some embodiments, the feedstock is ground into finer pieces or otherwise treated to increase surface area of the material. In some embodiments, the pre-treatment comprises at least one of the following: acid hydrolysis (see, e.g., U.S. Pat. Nos. 4,174,976 and 5,597,714; and PCT Publication WO/2006/086861), steam explosion (see, e.g., U.S. Pat. No. 6,506,282 and PCT Publication WO/2000/039387), autohydrolysis, ionic liquids (see, e.g., U.S. Pat. No. 6,824,599), hot water, ammonia explosion (see, e.g., U.S. Pat. No. 5,037,663), extrusion (see, e.g., U.S. Pat. No. 7,037,096), or microwave treatment (see, e.g., U.S. Pat. No. 5,196,069).

In some embodiments, the cellulose-containing biomass feedstock is first pre-treated to render biomass particles having small sizes (e.g., milled). It has been noted that yield of biofuel (e.g., ethanol) can be improved by using biomass particles having small sizes, e.g., biomass particles having a relatively uniform particle size of less than 1600 microns. For example, at least 75%, 85%, or 95% of the pretreated biomass particles have a particle size from about 100 microns to about 800 microns, or a particle size from about 100 microns to about 500 microns. Pretreated biomass particles can be generated by, e.g., a hammer mill or a colloid mill or a shear mill or a cavitation mill; serial combinations of any two or more of these can also be employed. For example, the colloidal mill can be used to select the resulting particle size distribution through the use of gap rotational controls. A relatively precise particle size distribution can be obtained from much larger biomass material using a colloid mill in contrast to alternative pretreatment techniques such as comminution with a hammer mill. An appropriate gap size on the colloid mill can produce a highly uniform suspension of biomass, where the maximum particle size of the biomass is greatly reduced and significantly more uniform compared to using only the comminution device. The radial gap size for a colloidal mill used in a corn ethanol plant can range from 0.104-0.728 millimeters, e.g., from 0.104-0.520 millimeters, e.g., from 0.208-0.520 millimeters, such that the resulting particle sizes are in the range of 100-800 microns. For example, in some embodiments, a gap setting of 0.1-0.15 is used for corn stover or other cellulosic biomass and a gap setting of 0.2-0.3 mm is used for grains including but not limited to corn kernels. As a second example, a shear mill can be used to reduce particle size of cellulose-containing materials under high shear action, especially for fibrous woody material. In shear milling, the material is processed through several generator stages (typically three) of a dispersing device which produces very fine suspensions. The stages consist of rotor-stator combinations to reduce particle size and create a very narrow size distribution from larger-sized woody feedstock material. Various combinations of generators can be used to achieve desired particle size reductions, such as suspensions containing particles in the range of 100 to 300 microns. Techniques for generating biomass particles having small sizes are fully described by, e.g., U.S. Patent Application Publication No. 20100055741, the content of which is incorporated by reference in its entirety herein.

In some embodiments, fermentation temperatures will be controlled between 28-35° C. and pH 4.0-5.5. In some embodiments, a temperature-tolerant yeast cell strain can be used, and accordingly a higher fermentation temperatures can be used (e.g., at or above 35° C., 36° C., 37° C., 38° C., 39° C., 40° C., 41° C., or 42° C.).

In some embodiments, the cellulose-containing biomass feedstock can be used as an inexpensive form of sugar (i.e., for value added products). In some of these embodiments, excess sugar is bled from the saccharification tank(s) (i.e., where the enzymes are converting plant material to sugar), for example using a sequential membrane, filtrate wash, or other sugar removal system. This reduces the sugar concentration in the saccharification tank(s) and allows for hydrolysis to continue without being inhibited by excess sugar. Residual non-sugar producing solids can be optionally purged forward for further processing or for other uses (such as for fuel value in a cogeneration system).

Acetic acid or its cognate base acetate can accumulate resulting from some biomass pretreatment methods. The methods, polynucleotide sequences and cells provided herein provide for cells with increased resistance to high levels of acetic acid (e.g., >0.8%), which are toxic to most yeast cells. Thus, in some embodiments, the biomass contacted with the cell expressing the Haa1 mutant protein has at least 0.5%, 0.8%, or 1.0% acetic acid and/or acetate.

Furfurals can accumulate in some pretreatment methods and/or saccharification reactions. Furfurals can in some embodiments act as yeast growth inhibitors. Thus, bacteria or yeast that consume furfurals can also be added to the fermentation to selectively reduce or eliminate the furfurals. The methods, polynucleotide sequences and cells provided herein provide for cells with increased resistance to high levels of furfural (>1000 ppm) which are toxic to most yeast. The methods, polynucleotide sequences and cells provided herein also provide for cells with increased resistance to elevated levels of furfural (>600 ppm) in combination with 100 mM acetate.

In some embodiments, the mixture of improved yeast cells and the cellulose-containing biomass feedstock are incubated to result in production of sugars from cellulose or other plant material and subsequent fermentation of the sugars into alcohols. Industrial fermentation conditions are known in the art. In some embodiments, a modified form of Simultaneous Saccharification and Fermentation (SSF) can be accomplished by using a small saccharification step in order to produce a small amount of sugar to promote yeast growth. This partially converted media is then sent to the fermenter. After the fermenter volume is approximately 10-20% of the total fermenter volume the yeast inoculum is added. The tank is then continuously filled in a fed batch mode over a period of 25-35 hours and then held at 35° C. until the fermentation is complete (~72 hrs). This allows sufficient use of the sugars to prevent inhibition of the process. To improve alcohol production, yeast strains with a high ethanol tolerance can be selected. In some embodiments, yeast growth stimulants can also be added to the mixture. For example, sterols can be added to stimulate yeast growth and enzyme production.

In some embodiments, the yeasts provided herein are exceptionally efficient for the production of ethanol. However, some of the same yeasts can be used for saccharification without subsequent fermentation. This can be accomplished, for example, by, e.g., allowing the yeasts to generate biomass hydrolysate, limiting ethanol production, followed by deactivation of the yeast so the fluid contains free enzymes and proteins. In the case of yeasts that have the expressed enzymes attached to the surface, the yeasts can be cultivated, deactivated with ultrasound and then used as immobilized enzymes within the saccharification vessel. The yeast can be filtered at the end of the saccharification process along with the other solids in this manner.

In some embodiments, the mixture of yeast cells and the cellulose-containing biomass feedstock are incubated to result in production of biomass-derived intermediates from cellulose or other plant material. As defined herein, the term "biomass-derived intermediate" refers to a carbohydrate intermediate derived from biomass deconstruction. In some embodiments, the biomass-derived intermediates are simple sugars, e.g., monosaccharides and disaccharides such as glucose, fructose, mannose, and galactose, sucrose, maltose, lactose, cellobiose, and derivatives thereof. In some embodiments, the biomass-derived intermediates are partial hydrolysis or partial depolymerization intermediates, e.g., cellobiose. In some embodiments, the biomass-derived intermediates are non-sugar biomass-derived intermediates. In some embodiments, the non-sugar biomass-derived intermediates are polyols, e.g., sorbitol, anhydrosorbitol, glycerol, and propanediol. In some embodiments, the non-sugar biomass-derived intermediates are isomerization and dehydration products derived from biomass hydrolysis and fermentation process, e.g., "reversion products," "acyclic intermediates," and "fructofuranosyl intermediates" as described in Chheda et al., *Angew. Chem. Int. Ed.* 46:7164-7183, 2007. In some embodiments, the non-sugar biomass-derived intermediates are additional dehydration and fragmentation products of acyclic intermediates and fructofuranosyl intermediates as described in Chheda et al., *Angew. Chem. Int. Ed.* 46:7164-7183, 2007. In some embodiments, the non-sugar biomass-derived intermediates include furans, e.g., furfural, 5-hydroxymethylfurfural, di-formylfuran, and derivatives thereof (e.g., 2,5-funandicarboxylic acid, di(hydroxymethyl)tetrahydrofuran, methyl tetrahydrofuran). Additional examples of biomass-derived intermediates are known in the art and disclosed in Chheda et al., *Angew. Chem. Int. Ed.* 46:7164-7183, 2007. In some embodiments, the non-sugar biomass-derived intermediates are amino acids and organic acids, such as levulinic acid, formic acid, fumaric acid, aspartic acid, succinic acid, malic acid, 3-hydroxypropionic acid, aspartic acid, itaconic acid, glutamic acid, glucaric acid, gluconic acid. If desired, any of the above products (i.e., sugar biomass-derived intermediates or non-sugar biomass-derived intermediates) can be further purified from the remainder of the reaction mixtures and/or chemically or enzymatically converted to yet another desired product.

The activity or amount of fermentation of the strain expressing the improved Haa1 protein described herein can be determined directly by HPLC assay for ethanol. The improved activity can also be determined by measuring the amount of carbohydrates converted to the desired product by HPLC. The amount of acetic acid can be determined directly by HPLC assay.

The applications of increased acetic acid or acetate tolerance of yeast strains include commercial processes as those employed in corn ethanol plants and cellulosic ethanol biorefineries or a merging of fermentation of the two corn grains; in operations for production of bio-based chemicals; and as a selective mechanism against growth of native contaminating yeast strains in fermentations.

EXAMPLES

1. Background

Biological conversion of sugars present in lignocellulosic biomass to a desired end product is confined to microorganisms that typically use glucose and/or xylose as carbon sources. The efficient use of sugars in biofuels applications is particularly important due to the high fractional percentage of hemicellulose containing xylan, the branched polymeric precursor to xylose. Upon biomass pretreatment, the hemicellulose and therefore xylan is disrupted to liberate inhibitors of microbiological fermentation. One of the pretreatment products derived from xylan is acetic acid which can form from hydrolysis of acetyl groups attached to xylan polymers during the pretreatment processes.

Figure 3:
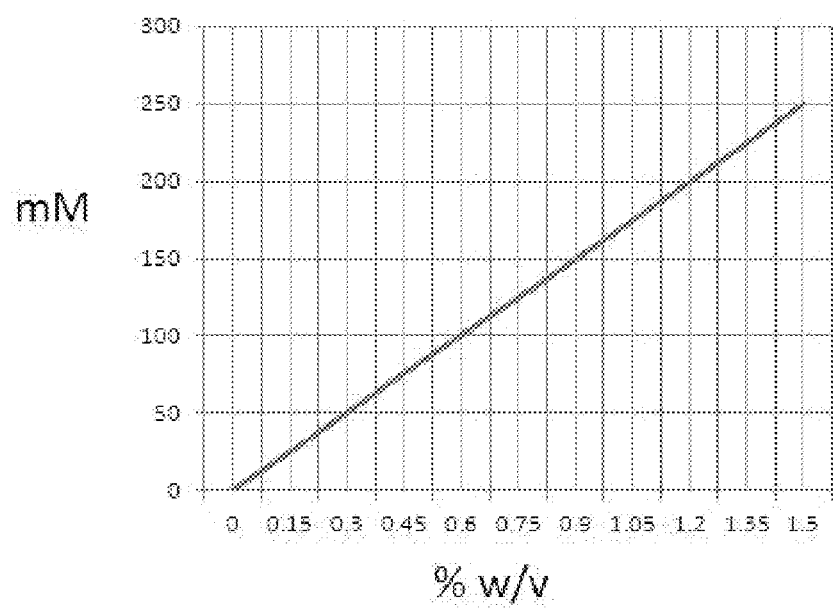
FIG. 3. Conversion of Acetate Concentration from mM to % w/V

The yeast *Saccharomyces cerevisiae* is a preferred organism for biological conversion of sugars into desired metabolic products. Its long history of industrial applications is evidence of its robust metabolic pathways, high tolerance to ethanol, rapid growth rate, and efficient conversion of glucose. However, it is sensitive to acetic acid in concentrations starting above 50 mM (about 0.3% w/v; see FIG. 3 for conversion graph). This poses a problem for biofuels application in which pretreated biomass can liberate acetic acid at higher concentrations. In the case of thermo-mechanical pretreatment, acetic acid levels associated with hemicellulose deconstruction can reach >0.5% w/v using greater than 10% biomass solids.

Acetic acid can exist as the protonated acid, or as its conjugate base acetate. The pKa of acetic acid is 4.75, near the pH at which fermentations are performed with *S. cerevisiae*. At pH <5.5, acetic acid present in the cellulosic sugars material will be at equilibrium favoring acetic acid over acetate. The metabolic inhibitory effect mediated by this organic acid is more pronounced in its undissociated state at lower pH.

The mechanism of acetic acid toxicity has been investigated, but commercially relevant strains of engineered *S. cerevisiae* strains with higher tolerance to acetic acid have not been reported. Naturally arising yeast variants have been used commercially in producing sake and sourdough, but the mixture and concentrations of inhibitors generated during biomass pretreatment for cellulosic ethanol production present a novel acetic acid mileu for organisms to handle.

Further, yeast strains have differing sensitivities to acetic acid; *Pichia stipitis*, which ferments xylose, is highly sensitive at 0.5% typically, whereas *Zygosaccharomyces bailii* is highly resistant at this concentration. This reflects differing ability to utilize and/or evade the toxic effects of acetate in these species. Acetic acid toxicity derives from alteration of the proton gradient across the cell membrane leading to cell wall defects, disruption of mitochondrial function, inhibition of growth rate and extension of lag phase, decreased life span, down regulation of genes involved in mitochondrial protein synthesis and carbohydrate metabolism, and/or up regulation of genes involved in amino acid metabolism. Metabolomic analysis of bacteria showed that acetic acid stress impacted numerous functions including lactate, formate and ethanol fermentation pathways, electron transport, and fatty acid biosynthesis.

Some of the pleiotropic effects on metabolic function derive from altered gene regulation as shown by transcriptomic studies. This pointed to transcriptional regulation of acetic acid stress response genes via transcription factors and associated protein complexes. Therefore a protein that can regulate acetic acid response that is naturally present in *S. cerevisiae* was targeted for PCR mutagenesis. Adaptive selection has traditionally been used for commercial yeast strains; however the generation of yeast with enhanced functional capabilities has been greatly accelerated due to *S. cerevisiae* genomic sequence availability and the requisite molecular biological tools.

This approach to generate commercially useful strains that have higher tolerance to acetic acid through genetic engineering builds on the cell's natural defense mechanisms of resistance or adaptation. *Saccharomyces* can respond to high concentration of acid by actively extruding it or neutralizing it. The vacuole is a cellular organelle which plays a major role in intracellular pH regulation. Cellular metabolism depends on maintenance of a pH difference of ~1.7 pH units between the vacuole and cytoplasm such that the vacuole is usually at a pH of 6 or lower while the cytoplasm is closer to neutrality. The vacuolar $H^+$ ATPase is the pump which drives this reaction. Another $H^+$ ATPase resides in the plasma membrane and pumps protons out. Other transporters contribute to maintenance of the pH gradient by moving amino acids, polyamines and metal ions in or out of the vacuole or by pumping monocarboxylic acid anions out through the plasma membrane. Movement of imidazole-containing amino acids such as histidine appears to function prominently in the vacuole-dependent "buffering" process.

At lower pH, acetate exists substantially in the undissociated state ($CH_3COOH$), a form which potently inhibits growth. The undissociated acid, being uncharged, readily diffuses across the cell membrane only to dissociate in the higher pH environment of the cytosol. Such dissociation generates protons and the acid anion ($CH_3COO^-$). The acid anion will tend to accumulate intracellularly to very high levels as, being charged, it cannot very readily diffuse from the cell.

This high anion accumulation may generate an abnormally high turgor pressure. It can also influence free radical production, leading to the severe oxidative stress that is a major component of weak organic acid stress in aerobic *S. cerevisiae*. The proton release can potentially acidify the cytosol. This acidification, if it occurs, will inhibit many metabolic functions. Reductions in *S. cerevisiae* intracellular pH have been demonstrated following the addition of acetate although a reduction in intracellular pH is not always a feature of organic acid stress.

The HAA1 gene is located centromere-proximal on chromosome XV1 and encodes a DNA-binding transcription factor. Null mutants in HAA1 are more sensitive to butyric acid, propionic acid and acetic acid (Fernandes 2005). The pleiotropic response of acetic acid stress is further explained by the fact that the HAA1 gene has an Adr1 protein regulatory binding site upstream, a carbon source-responsive zinc-finger transcription factor, required for transcription of the glucose-repressed gene ADH2, of peroxisomal protein genes, and of genes required for ethanol, glycerol, and fatty acid utilization.

Provided herein are engineered microorganisms with enhanced tolerance to acetic acid or its cognate base acetate.

2. Cloning and Expression of HAA1 Wild Type *S. Cerevisiae* Gene

The HAA1 gene was cloned in the plasmid shuttle vector p416 Tef (Mumberg et al., 1995) by PCR amplification of a DNA fragment from *Saccharomyces cerevisiae* strain TR3, cleavage with restriction enzymes Xba I and Sal I and ligation into the appropriate sites of the vector for expression from the plasmid-borne Tef promoter.

Mutagenesis of the carboxy-terminal ~350 amino acids of the HAA1 gene was carried out by PCR synthesis of a smaller Xba I-Sal I DNA subfragment of the HAA1 gene using the Mutazyme protocol (GeneMorph II Kit). This fragment was then recloned into the same vector using the same restriction enzyme cleavage and ligation protocol, and the mixture of mutated and non-mutated DNAs was transformed into strain TR3.

Figure 1:
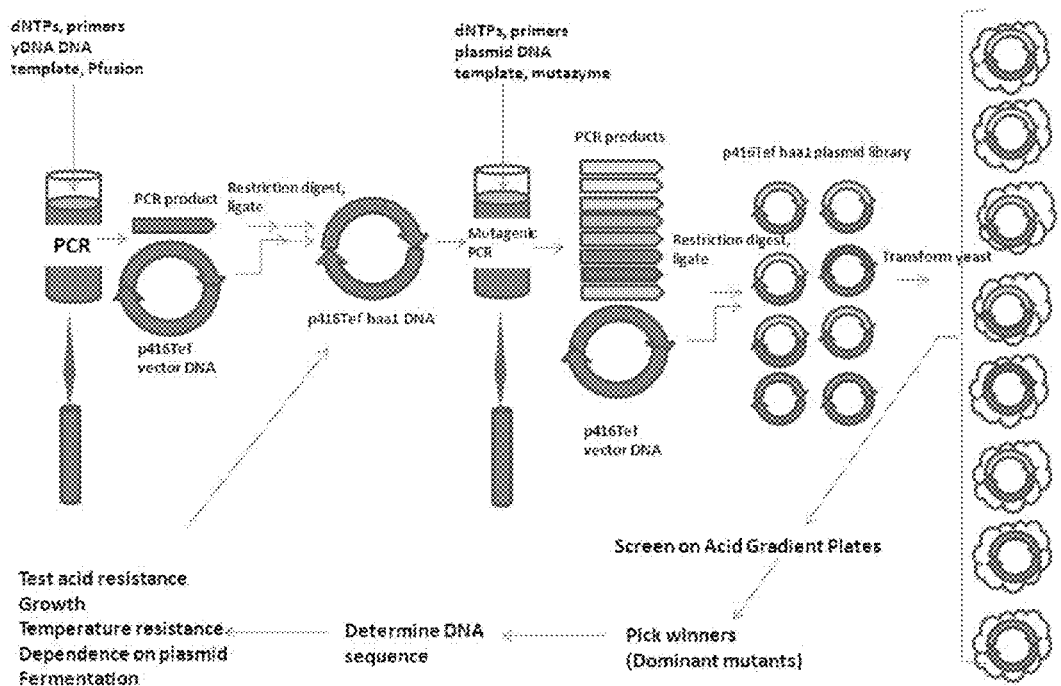
FIG. 1. Schematic representation of the experimental process leading to the isolation of novel haa1 alleles The upper left shows PCR synthesis of the HAA1 gene from yeast DNA and cloning in the shuttle plasmid vector p416 Tef. The upper middle shows mutagenic PCR of the HAA1 gene generating many allelic variants to create a library of mutants and their transformation into yeast. The lower right portion shows the process of screening these mutants, picking out the most acetate resistant variants and determining their DNA sequence. Other relevant characteristics of the mutants are also studied such as growth rate, fermentation ability temperature resistance and dependence of the acetate resistant phenotype on the resident plasmid.
Figure 2:
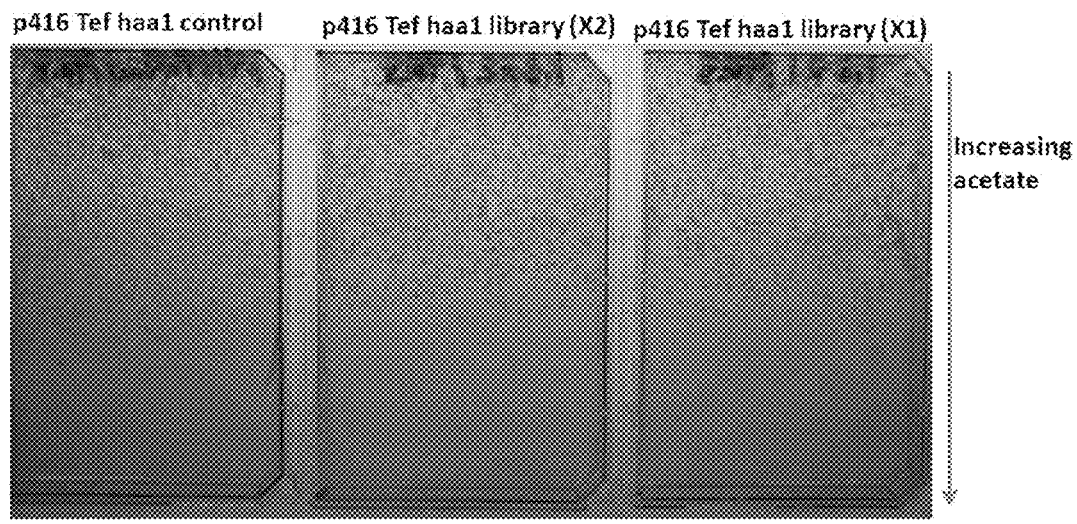
FIG. 2. Acetate gradient plates for screening haa1 mutant libraries for acetate resistant variants Three acetate gradient plates are shown. From left to right, a control plating of the unmutagenized HAA1 gene cloned in the p416 Tef vector, high density plating of the mutagenized haa1 gene "library" cloned in the p416 Tef vector and lower density plating of the same mutagenized library as shown in the middle panel. The arrow indicates the direction of increasing concentration of acetate in the plate. Colonies with higher tolerance to increased levels of acetate were isolated from the leading edge of the cell plating area by manually picking individual colonies and re-streaking for single clonal isolates on a fresh agar-substrate Petri dish.

After appropriate recovery of transformants in rich media, a set of 40 independent acetate resistant mutants was isolated from the leading edge of an acetate gradient plate, containing the higher acetate concentration, made with media selective for the vector. The mutants were colony purified and plasmid DNA was isolated and retransformed into bacteria in order to amplify it for DNA sequence determination. A simplified scheme of the protocol used to mutagenize, clone and screen for mutants is shown in FIG. 1. Acetate gradient plate screening is illustrated in FIG. 2.

3. Haa1 Mutant Screening

Each of the mutants was grown in liquid selective media and the cell densities were normalized to enable spot testing on a series of plates containing increasing acetate concentrations. A subset of six of the more highly acetate resistant strains was chosen for further characterization (FIG. 4). Sequences of these mutants were aligned to determine if any consistent pattern of mutated residues was present (FIG. 5A-C). This was further refined to two distinct mutant strains which showed consistent growth on 140 mM acetate (0.82% w/v). The sequence differences from the wild type sequence are shown in FIG. 6.

4. Integration of Haa1 Mutant Alleles into *S. Cerevisiae* Genome

Both haa1 mutant alleles were PCR amplified along with the flanking DNA containing the heterologous constitutive promoter and downstream terminator. In addition, a URA3 marker was incorporated into the fragment to provide a selectable marker for the transformation and homology to the HAA1 locus was incorporated in the fragment on both sides to promote integration into this region of the chromosome. The DNA fragments were used to transform a yeast strain that was deficient for uridine biosynthesis and 10-20 URA3 recombinants were isolated for each mutant. The strategy of PCR synthesis by the overlapping PCR method and integration of the PCR fragment into the genomic HAA1 locus is shown in FIG. 7.

PCR analysis of the chromosomal DNA was carried out and those candidates demonstrated to contain full-length insertions of both alleles along with the flanking DNA were analyzed for acetate resistance. Clonal isolates containing genomic insertion of only one of the alleles conferred acetate resistance (haa1 mut2). Both alleles were subjected to counterselection on plates containing 5-fluoroorotic acid to identify recombinants which had lost the URA3 marker. Again, several ura-candidates of each of the alleles were characterized by DNA sequencing to demonstrate that the amino acid changes were incorporated into the yeast genome.

Acetate resistance of the recombinants was again assayed. It was clear from the DNA sequencing experiment that the mutational changes of both alleles were incorporated into the genomic HAA1 locus as predicted. However, one integrated allele (haa1 mut2) could provide acetate resistance as the sole source of Haa1 function, whereas the other could not (haa1 mut 40). This result is depicted in FIG. 8.

Example 1

Selection of Haa1 Viable Cells from Colonies at Leading Edge of Acetate Gradient Plates Gradient plates containing acetate (pH 4.5) were poured using a modification of the method (BRYSON V, SZYBALSKI W. Microbial selection. Science. 1952 Jul. 18; 116(3003):45-51). Plate pouring was carried out in a sterile biological safety cabinet. Omni trays (NUNC, 86×128 mm) were used and inclined on the short edge by leaning the plate bottom on the plate lid. Molten CSM agar (-uracil) was prepared from the standard CSM premix (MP Biochemicals) and 0.7 ml 5M sodium acetate (pH 4.5) was added to 30 ml of agar which was poured into the plate and allowed to solidify as the lower "wedge". The plate was laid horizontally in the sterile hood and the upper "wedge" of 30 ml of CSM agar (-uracil) was poured on top of the lower layer. The plate was allowed to solidify and mixtures of freshly transformed yeast cells were spread on the plates using sterile glass beads. "Libraries" of transformed yeast cells were plated which contained a mixture of the mutagenized gene encoding the Haa1 protein inserted within the p416 tef shuttle vector. These were incubated at 30° C. for 5-7 days in order to produce distinct large colonies which could be subsequently re-isolated using sterile toothpicks and streaked on CSM (-uracil) agar without acetate for colony purification. An example of such a gradient plating is shown in FIG. 2. Forty distinct clearly separated colonies were isolated from the leading edge of the gradient in this way. These represented a random sampling of the most putatively highly acetate-resistant haa1 mutants.

Example 2

Comparative Growth of Haa1 Mutants on Single Concentration Acetate Medium in Petri Dishes Putative haa1 mutants colony purified from the gradient plates were subjected to a detailed analysis of acetate resistance by replating on a series of CSM (-uracil) plates containing fixed concentrations of acetate, prepared as described above, but without introduction of a gradient. The plates contained 0 mM, 100 mM, 110 mM, 120 mM, 130 mM or 140 mM acetate and were prepared in standard petri dishes (BD Falcon, 100×15 mm). Cells were grown overnight in culture tubes containing CSM (-uracil) liquid media and normalization to similar OD600 values was carried by measurement of OD600 in a spectrophotometer (Genesys 10UV) and dilution with sterile media. Appropriately diluted cultures were then sterilely transferred to 96 well plates (Greiner Bio One, PS-microplate, flat bottom) and serially diluted with sterile water in 10-fold steps down adjacent columns of the plate. Approximately equal volumes (3 ul) were transferred to each of the series of fixed concentration acetate plates using a 48 pin replicator (V&P Scientific, VP 407AH multi-blot replicator). In this way, acetate resistance of up to six strains could be compared on a single petri plate. Duplicate plates at each concentration of acetate were used for the analysis. Plates were allowed to incubate approximately 5 days at 30° C. and then growth was compared. A sample of this result is shown in FIG. 4.

Example 3

Colony Growth Plating Assay to Assess Acetate Resistance of Haa1 Plasmid Bearing Strains in Recycle Medium To investigate the growth properties of haa1 mutant strains in a more relevant biomass-based growth material, cells were plated on solid medium containing varying percentages of pretreated, saccharified and fermented cellulosic sugars mixtures.

A series of plates was prepared by mixing one volume of 2× concentrated CSM (-uracil) agar and one volume of sterile high pressure/high temperature pretreated (HPHT) recycle mixture or sterile water as a control. HPHT mixtures were prepared by mixing mechanically treated biomass samples with water and treating in a sealed pressure cell at high temperature, allowing the mixture to cool and then saccharifying with a mixture of cellulolytic enzymes and then subjecting this to fermentation with EdeniQ proprietary *Saccharomyces cerevisiae* strains. The saccharified and fermented HPHT mixture was then centrifuged to remove solids and the supernatant was treated in a rotary evaporator to remove ethanol (Buchi Rotavapor R-215). This mixture was diluted with water appropriately (0%, 40%, 60%, 80%, 100%) and mixed with biomass and another round of HPHT treatment followed by saccharification was performed to generate the "HPHT recycle" mixture. This material was subjected to centrifugation to remove solids and filter sterilized to generate the 0%, 40%, 60%, 80%, 100% HPHT which were then mixed 1:1 with the molten 2×CSM (-uracil) agar components. CSM agar-HPHT recycle mixtures were poured into Omni trays (NUNC) as described above to create a series of plates containing recycle mixtures at five different concentrations. Six plasmid-borne versions of the haa1 gene isolated from a mutagenic "library" and containing changes at various positions in the haa1 gene were compared to a naïve strain containing the p416 Tef vector or a strain bearing the unmutated haa1 gene. Each isolate was grown in selective media and cell concentrations were normalized as described above. Spot testing was carried out as described above using the 48 pin replicator. Plates were incubated at 30° C. for eight days and growth was compared.

Higher levels of acetate resistance were observed when strains bearing certain plasmids are plated in a 50% mixture of CSM-ura media and "recycle HPHT" extracts under some conditions. For example, the haa1 mut40 mutant gave >100 fold greater colony forming units when normalized to the reference strain in plating controls when grown on biomass "recycle HPHT" medium at the 80% recycle level. This result is shown in FIG. 9.

Example 4

Colony Growth Assay on Acetate-furfural Containing Plates

To demonstrate that synergistic inhibitor effects are contributing to the inhibition phenotypes observed in more complex mixtures, an experiment testing the effect of a series of increasing furfural concentrations mixed either with no acetate or 100 mM acetate with was performed A set of plates was prepared by mixing CSM (-uracil) agar and a series of increasing amounts of furfural dissolved in ethanol (0.4 g/ml, 0.6 g/ml, 0.8 g/ml and 1.0 g/ml). Another set of plates was prepared by adding acetate to 100 mM as described above and then combining this with a series of increasing amounts of furfural dissolved in ethanol as described above. Control plates were prepared containing CSM (-uracil) agar and 100 mM acetate. CSM (-uracil) agar-furfural-acetate mixtures were poured into Omni trays (NUNC) as described above to create a series of plates containing furfural-acetate mixtures at the four different concentrations. Six plasmid-borne versions of the haa1 gene isolated from a mutagenic "library" and containing changes at various positions in the haa1 gene were compared to a naïve strain containing the p416 Tef vector or a strain bearing the unmutated haa1 gene. Each isolate was grown in selective media and cell concentrations were normalized as described above. Spot testing was carried out as described above using the 48 pin replicator as shown in FIG. 10. Plates were incubated at 30° C. for eight to ten days and growth was compared.

It can be seen that tolerance to higher furfural levels occurred in the absence of acetate (lower panel). Presence of 100 mM acetate in the mix reduced furfural tolerance of the TR3 *Saccharomyces cerevisiae* yeast strain by more than 0.2 grams/liter. Cells expressing the improved Haa1 mut2 and Haa1 mut40 proteins produced >100 fold increase in colony forming units when normalized to a reference strain in 600 ppm furfural and 100 mM acetate. This result can be seen in FIG. 10.

Example 5

Fermentation with WT and Haa1 Mut2 in Pretreated/Saccharified Biomass Cellulosic Sugars Extract Single colonies of either the TR3 wild type or TR3 haa1 mut2 strain were isolated from cultures streaked onto YPDC plates and inoculated into 2.5 ml volumes of YPDC liquid media and incubated overnight at 30° C. in an orbital shaker at 130 rpm. Each cell type was subcultured overnight in 200 ml YPDC liquid media in a 1 L baffled Erlenmeyer flask and incubated as described above. Cells were pelleted by centrifugation at 5000 rpm for 10 minutes and then resuspended and pre-adapted overnight in a mixture of 70% of 4% molasses medium/30% pretreated saccharified sugar cane bagasse at 34° C. in a Thermo MaxQ rotary shaker at 130 rpm. A portion of the culture was diluted 1:100 in distilled water and stained with methylene blue and then counted on a Petroff-Hausser brightline hemocytometer to determine viable cell number.

Saccharified bagasse that had been subjected to thermomechanical pretreatment was adjusted to 18% solids for fermentation with the wild type and improved haa1 mut2 yeast strains. Fermentation was carried out at 34° C., in 500 ml Erlenmeyer flasks containing 100 g of biomass sealed with a rubber stopper and aspirator needle in a Thermo MaxQ rotary shaker at 130 rpm. $40 \times 10^6$ cells of either the wild type or the haa1 mut2 allele were added per gram of biomass to the flasks. In half of the flasks, acetate in the form of 5M sodium acetate pH 4.8, was supplemented to a final concentration of greater than 0.8% w/v. The control (T0) was 0.85% w/v; wild type TR3 (T24 hr fermentation) was 0.81% w/v; improved TR3 haa1 mut2 (T24 hr fermentation) was 0.82% w/v. Flasks were sampled at 0 hours and 24 hours after addition of the fermentation organisms.

Samples were analyzed for sugars, acetic acid, glycerol and ethanol on a Bio-Rad Labs Aminex HPX87H 300×7.8 mm, analytical HPLC column employing a mobile phase of 0.005N $H_2SO_4$ at a flow rate of 0.6 ml/minute.

As shown in control experiments in FIG. 11, the parental wild type strain TR3 or the mutant, TR3 haa1 mut2, in the absence of exogenous acetate can completely ferment glucose present in saccharified sugarcane bagasse within 24 hours to quantitatively yield ethanol.

As also shown in the control experiments, the level of acetate present as a result of pretreatment of the biomass, approximately 0.2% w/v, does not significantly inhibit the fermentation. When fermentation flasks were supplemented with acetate to greater than 0.8% w/v, strong inhibitory effects were observed with the parental strain TR3, with only about 20% of the glucose utilized at 24 hrs. In contrast, the TR3 haa1 mut2 strain utilized 80% of the available glucose under the same conditions at 24 hrs and produced almost twice as much ethanol. Specifically, there is greater than 50% increase in titer of fermentation product performed by the haa1 mutant strain compared to control strain under conditions of greater than 0.8% w/v acetate under at 24 hrs under these fermentation conditions using pretreated/saccharified bagasse biomass.

Similar results were obtained with pretreated saccharified corn stover at the same solids concentration as sugar cane bagasse. The faster fermentation kinetics of the improved haa1 mut2 engineered yeast strain is useful in commercial operations where higher and faster throughput can lower operational expense.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. An isolated polynucleotide encoding a transcription factor polypeptide comprising an amino acid sequence that:
   a. is at least 95% identical to amino acid sequence of SEQ ID NO:2; and
   b. comprises at least one amino acid difference compared to SEQ ID NO:2 selected from the group consisting of F440Y, P518S, D508Y, N510K, A527V, I591V, H605Y, S622F, S639F, and S673L.

2. The isolated polynucleotide of claim 1, wherein the amino acid sequence is at least 95% identical to SEQ ID NO:2.

3. The isolated polynucleotide of claim 2, wherein the amino acid sequence comprises the following amino acid differences compared to SEQ ID NO:2: F440Y, P518S, I591V, H605Y, S622F, S639F, and S673L.

4. The isolated polynucleotide of claim 1, wherein the polypeptide has a C-terminal deletion resulting in a polypeptide having fewer than 600 (e.g., fewer than 590, 580, 570, 560, 550) amino acids.

5. The isolated polynucleotide of claim 1, wherein the amino acid sequence comprises the following amino acid differences compared to SEQ ID NO:2: D508Y, N510K, and A527V.

6. The isolated polynucleotide of claim 1, wherein the amino acid sequence comprises at least two (e.g., 2, 3, 4, 5, 6, 7, or more) amino acid differences compared to SEQ ID NO:2 selected from the group consisting of F440Y, P518S, D508Y, N510K, A527V, I591V, H605Y, S622F, S639F, and S673L.

7. An expression cassette comprising a heterologous promoter operably linked to the polynucleotide of claim 1.

8. The expression cassette of claim 7, wherein the promoter is heterologous to the polynucleotide.

9. A yeast cell comprising the expression cassette of claim 7, wherein the yeast cell ferments sugar in the presence of acetate with increased kinetics or increased fermentation-product titer than a control yeast cell lacking the expression cassette.

10. The yeast cell of claim 9, wherein the yeast cell is a *Saccharomyces cervisiae* or *Pichia stipitis* cell.

11. The yeast cell of claim 10, wherein the yeast cell lacks a wild type allele of HAA1.

12. The yeast cell of claim 10 comprising a genomically-integrated mutant haa1 allele replacing the wild type HAA1 allele.

13. The yeast cell of claim 10 comprising a mutant haa1 allele on a heterologous plasmid, wherein the cell also comprises a genomic wild type allele of HAA1.

14. The yeast cell of claim 9 exhibiting fermentation with increased kinetics or increased fermentation-product titer compared to a control yeast strain in the presence of 0.5% w/v or more acetate or 0.5% w/v or more acetic acid.

15. The yeast cell of claim 9 exhibiting fermentation with increased kinetics or increased fermentation-product titer compared to a control yeast strain in the presence of 0.8% w/v or more acetate or 0.8% w/v or more acetic acid.

16. A method of making ethanol from sugar, the method comprising contacting the yeast of claim 10 to a solution comprising sugar under conditions to allow for fermentation of the sugar into ethanol; and recovering the ethanol.

17. The method of claim 16, wherein the solution comprises sufficient furfural to inhibit fermentation of a control yeast lacking the expression cassette.

18. An aqueous mixture comprising sugars, acetic acid and/or acetate and the yeast cell of claim 10.

19. The mixture of claim 18, wherein the mixture comprises at least 0.5% or at least 0.8% w/v acetic acid or acetate.

20. The mixture of claim 18, wherein the mixture comprises cellulose-containing biomass.

* * * * *

SEQUENCE LISTING

```
<160> NUMBER OF SEQ ID NOS: 21

<210> SEQ ID NO 1
<211> LENGTH: 694
<212> TYPE: PRT
<213> ORGANISM: Saccharomyces cerevisiae
<220> FEATURE:
<223> OTHER INFORMATION: Saccharomyces cerevisiae strain S288c wildtype
      promoter DNA-binding transcription factor Haa1p,
      locus YPR008W, control Haa1 protein,
      transcriptional activator

<400> SEQUENCE: 1

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
            20                  25                  30

Ile Lys Pro Lys Gly Arg Pro Ser Thr Thr Cys Asp Tyr Cys Lys Gln
        35                  40                  45

Leu Arg Lys Asn Lys Asn Ala Asn Pro Glu Gly Val Cys Thr Cys Gly
    50                  55                  60

Arg Leu Glu Lys Lys Lys Leu Ala Gln Lys Ala Lys Glu Glu Ala Arg
65                  70                  75                  80

Ala Lys Ala Lys Glu Lys Gln Arg Lys Gln Cys Thr Cys Gly Thr Asp
                85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
        115                 120                 125

Phe Glu Arg Val Leu Ser Ser Thr Ser Leu Asp Ser Asn Met Leu Ser
    130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Ile Pro Gln Ser Pro Pro Leu Ser Ser Met Ser
```

```
            195                 200                 205
Phe Asn Phe Leu Thr Gly Asn Ile Asn Glu Thr Asn Gln Asn His Ser
210                 215                 220

Asn His Gln His Ser Lys Ser Gly Asn Trp Gln Asp Ser Ser Val
225                 230                 235                 240

Ser Leu Pro Ala Lys Ala Asp Ser Arg Leu Asn Met Met Asp Lys Asn
                    245                 250                 255

Asn Ser Val Gly Leu Asp Leu Leu Gly His Ser Lys Arg Ile Ser Pro
                260                 265                 270

Ile Ser Asn Ser Arg Val Gly Glu Val Ser Val Pro Leu Glu Glu Tyr
            275                 280                 285

Ile Pro Ser Asp Ile Asp Gly Val Gly Arg Val Thr Asp Lys Ser Ser
        290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                    325                 330                 335

Asn Cys Asn Arg Ile Asn Ser Lys Ser Tyr Ser Lys Thr Asn Ser Met
                340                 345                 350

Asn Gly Asn Gly Met Asn Asn Ser Asn Asn Asn Ile Asn Ser Asn
            355                 360                 365

Gly Asn Asp Lys Asn Asn Asn Ser Ser Arg Gln Glu His Gln Gly
370                 375                 380

Asn Gly Leu Phe Asp Met Phe Thr Asp Ser Ser Ser Ile Ser Thr Leu
385                 390                 395                 400

Ser Arg Ala Asn Leu Leu Leu Gln Glu Lys Ile Gly Ser Gln Glu Asn
                    405                 410                 415

Ser Val Lys Gln Glu Asn Tyr Ser Lys Asn Pro Gln Leu Arg His Gln
                420                 425                 430

Leu Thr Ser Arg Ser Arg Ser Phe Ile His His Pro Ala Asn Glu Tyr
            435                 440                 445

Leu Lys Asn Thr Phe Gly Asn Ser His Ser Asn Asp Ile Gly Lys Gly
        450                 455                 460

Val Glu Val Leu Ser Leu Thr Pro Ser Phe Met Asp Ile Pro Glu Lys
465                 470                 475                 480

Glu Arg Glu Thr Glu Arg Ser Pro Ser Ser Asn Tyr Ile Thr Asp Arg
                    485                 490                 495

Pro Phe Thr Arg Lys Pro Arg Ser Ser Ser Ile Asp Val Asn His Arg
                500                 505                 510

Tyr Pro Pro Met Ala Pro Thr Thr Val Ala Thr Ser Pro Gly Ala Leu
            515                 520                 525

Asn Asn Ala Val Ala Ser Leu Asp Asp Gln Leu Ser Leu Thr Ser
        530                 535                 540

Leu Asn Ser Gln Pro Ser Ser Ile Ala Asn Met Met Asp Pro Ser
545                 550                 555                 560

Asn Leu Ala Glu Gln Ser Ser Ile His Ser Val Pro Gln Ser Ile Asn
                    565                 570                 575

Ser Pro Arg Met Pro Lys Thr Gly Ser Arg Gln Asp Lys Asn Ile His
                580                 585                 590

Thr Lys Lys Glu Glu Arg Asn Pro Leu Asn Asn Ile His Asp Leu Ser
            595                 600                 605

Gln Leu Glu Asn Val Pro Asp Glu Met Asn Gln Met Phe Ser Pro Pro
        610                 615                 620
```

```
Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
            645                 650                 655

Arg Asn Asp Leu Pro Asp Thr Ser Pro Met Ser Ser Ile Gln Thr Ala
        660                 665                 670

Ser Pro Pro Ser Gln Leu Leu Thr Asp Gln Gly Phe Ala Asp Leu Asp
            675                 680                 685

Asn Phe Met Ser Ser Leu
        690

<210> SEQ ID NO 2
<211> LENGTH: 694
<212> TYPE: PRT
<213> ORGANISM: Saccharomyces cerevisiae
<220> FEATURE:
<223> OTHER INFORMATION: Saccharomyces cerevisiae strain TR3 wildtype
      promoter DNA-binding transcription factor Haa1p,
      control Haa1 protein, transcriptional activator

<400> SEQUENCE: 2

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
            20                  25                  30

Ile Lys Pro Lys Gly Arg Pro Ser Thr Thr Cys Asp Tyr Cys Lys Gln
        35                  40                  45

Leu Arg Lys Asn Lys Asn Ala Asn Pro Glu Gly Val Cys Thr Cys Gly
50                  55                  60

Arg Leu Glu Lys Lys Leu Ala Gln Lys Ala Lys Glu Glu Ala Arg
65                  70                  75                  80

Val Lys Ala Lys Glu Lys Gln Arg Lys Gln Cys Thr Cys Gly Thr Asp
            85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
            115                 120                 125

Phe Glu Arg Val Leu Ser Ser Thr Ser Leu Asp Ser Asn Met Leu Ser
130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
            165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Pro Leu Ser Ser Met Ser
            195                 200                 205

Phe Asn Phe Leu Thr Gly Asn Ile Asn Glu Thr Asn Gln Asn His Ser
            210                 215                 220

Asn His Gln His Ser Lys Ser Ser Asn Asn Trp Gln Asp Ser Ser Val
225                 230                 235                 240

Ser Leu Pro Ala Lys Ala Asp Ser Arg Leu Asn Met Met Asp Lys Asn
            245                 250                 255

Asn Ser Val Gly Leu Asp Leu Leu Gly His Ser Lys Arg Ile Ser Pro
            260                 265                 270
```

-continued

```
Ile Ser Asn Ser Arg Val Gly Glu Val Ser Val Pro Leu Glu Glu Tyr
            275                 280                 285
Ile Pro Ser Asp Ile Asp Gly Val Gly Arg Val Thr Asp Lys Ser Ser
290                 295                 300
Leu Val Tyr Asp Trp Pro Phe Asp Glu Ser Ile Glu Arg Asn Phe Ser
305                 310                 315                 320
Thr Thr Ala Thr Ala Ala Thr Gly Glu Ser Lys Phe Asp Ile Asn Asp
                325                 330                 335
Asn Cys Asn Arg Ile Asn Ser Lys Ser Tyr Ser Lys Thr Asn Ser Met
            340                 345                 350
Asn Gly Asn Gly Met Asn Asn Ser Asn Asn Asn Ile Asn Ser Asn
            355                 360                 365
Gly Asn Asp Lys Asn Asn Asn Ser Ser Arg Gln Glu His Gln Gly
    370                 375                 380
Asn Gly Leu Phe Asp Met Phe Thr Asp Ser Ser Ser Ile Ser Thr Leu
385                 390                 395                 400
Ser Arg Ala Asn Leu Leu Leu Gln Glu Lys Ile Gly Ser Gln Glu Asn
                405                 410                 415
Ser Val Lys Pro Glu Asn Tyr Ser Lys Asn Pro Gln Leu Arg His Gln
            420                 425                 430
Leu Thr Ser Arg Ser Arg Ser Phe Ile His His Pro Ala Asn Glu Tyr
        435                 440                 445
Leu Lys Asn Thr Phe Gly Asn Ser His Ser Asn Asp Ile Gly Lys Gly
    450                 455                 460
Val Glu Val Leu Ser Leu Thr Pro Ser Phe Met Asp Ile Pro Glu Lys
465                 470                 475                 480
Glu Arg Glu Thr Glu Arg Ser Pro Ser Ser Asn Tyr Ile Thr Asp Arg
                485                 490                 495
Pro Phe Thr Arg Lys Pro Arg Ser Ser Ser Ile Asp Val Asn His Arg
            500                 505                 510
Tyr Pro Pro Met Ala Pro Thr Thr Val Ala Thr Ser Pro Gly Ala Leu
        515                 520                 525
Asn Asn Ala Val Ala Ser Asn Leu Asp Asp Gln Leu Ser Leu Thr Ser
    530                 535                 540
Leu Asn Ser Gln Pro Ser Ser Ile Ala Asn Met Met Met Asp Pro Ser
545                 550                 555                 560
Asn Leu Ala Glu Gln Ser Ser Ile His Ser Val Pro Gln Ser Ile Asn
                565                 570                 575
Ser Pro Arg Met Pro Lys Thr Gly Ser Arg Gln Asp Lys Asn Ile His
            580                 585                 590
Thr Lys Lys Glu Glu Arg Asn Pro Leu Asn Asn Ile His Asp Leu Ser
        595                 600                 605
Gln Leu Glu Asn Val Pro Asp Glu Met Asn Gln Met Phe Ser Pro Pro
    610                 615                 620
Leu Lys Ser Met Asn Arg Pro Asp Ala Ile Arg Glu Asn Ser Ser Ser
625                 630                 635                 640
Ser Asn Phe Ile Ile Gln Gly Asn Ser Met Ile Ser Thr Pro Ser Gly
                645                 650                 655
Arg Asn Asp Leu Pro Asp Thr Ser Pro Met Ser Ser Ile Gln Thr Ala
            660                 665                 670
Ser Pro Pro Ser Gln Leu Leu Thr Asp Gln Gly Phe Ala Asp Leu Asp
        675                 680                 685
Asn Phe Met Ser Ser Leu
```

<210> SEQ ID NO 3
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3 promoter DNA-binding transcription factor Haa1p site-directed acetate resistant mutant mut2 (TR3mut2), transcriptional activator

<400> SEQUENCE: 3

```
Met Val Leu Ile Asn Gly Ile Lys Tyr Ala Cys Glu Arg Cys Ile Arg
  1               5                  10                  15
Gly His Arg Val Thr Thr Cys Asn His Thr Asp Gln Pro Leu Met Met
                 20                  25                  30
Ile Lys Pro Lys Gly Arg Pro Ser Thr Thr Cys Asp Tyr Cys Lys Gln
             35                  40                  45
Leu Arg Lys Asn Lys Asn Ala Asn Pro Glu Gly Val Cys Thr Cys Gly
 50                  55                  60
Arg Leu Glu Lys Lys Lys Leu Ala Gln Lys Ala Lys Glu Glu Ala Arg
 65                  70                  75                  80
Val Lys Ala Lys Glu Lys Gln Arg Lys Gln Cys Thr Cys Gly Thr Asp
                 85                  90                  95
Glu Val Cys Lys Tyr His Ala Gln Lys Arg His Leu Arg Lys Ser Pro
            100                 105                 110
Ser Ser Ser Gln Lys Lys Gly Arg Ser Ile Ser Arg Ser Gln Pro Met
            115                 120                 125
Phe Glu Arg Val Leu Ser Ser Thr Ser Leu Asp Ser Asn Met Leu Ser
130                 135                 140
Gly His Gly Ala Leu Ser Asp Thr Ser Ser Ile Leu Thr Ser Thr Phe
145                 150                 155                 160
Leu Asp Ser Glu Pro Gly Val Gly Lys Ile Ser Lys Asp Tyr His His
                165                 170                 175
Val Pro Ser Leu Ala Ser Ile Ser Ser Leu Gln Ser Ser Gln Ser Leu
            180                 185                 190
Asp Gln Asn Phe Ser Val Pro Gln Ser Pro Leu Ser Ser Met Ser
            195                 200                 205
Phe Asn Phe Leu Thr Gly Asn Ile Asn Glu Thr Asn Gln Asn His Ser
210                 215                 220
Asn His Gln His Ser Lys Ser Asn Asn Trp Gln Asp Ser Ser Val
225                 230                 235                 240
Ser Leu Pro Ala Lys Ala Asp Ser Arg Leu Asn Met Met Asp Lys Asn
                245                 250                 255
Asn Ser Val Gly Leu Asp Leu Leu Gly His Ser Lys Arg Ile Ser Pro
            260                 265                 270
Ile Ser Asn Ser Arg Val Gly Glu Val Ser Val Pro Leu Glu Glu Tyr
            275                 280                 285
Ile Pro Ser Asp Ile Asp Gly Val Gly Arg Val Thr Asp Lys Ser Ser
            290                 295                 300
Leu Val Tyr Asp Trp Pro Phe Asp Glu Ser Ile Glu Arg Asn Phe Ser
305                 310                 315                 320
Thr Thr Ala Thr Ala Ala Thr Gly Glu Ser Lys Phe Asp Ile Asn Asp
                325                 330                 335
Asn Cys Asn Arg Ile Asn Ser Lys Ser Tyr Ser Lys Thr Asn Ser Met
```

```
                340                 345                 350
Asn Gly Asn Gly Met Asn Asn Ser Asn Asn Asn Ile Asn Ser Asn
            355                 360                 365
Gly Asn Asp Lys Asn Asn Asn Ser Ser Arg Gln Glu His Gln Gly
            370                 375                 380
Asn Gly Leu Phe Asp Met Phe Thr Asp Ser Ser Ile Ser Thr Leu
385                 390                 395                 400
Ser Arg Ala Asn Leu Leu Leu Gln Glu Lys Ile Gly Ser Gln Glu Asn
                405                 410                 415
Ser Val Lys Pro Glu Asn Tyr Ser Lys Asn Pro Gln Leu Arg His Gln
                420                 425                 430
Leu Thr Ser Arg Ser Arg Ser Tyr Ile His His Pro Ala Asn Glu Tyr
                435                 440                 445
Leu Lys Asn Thr Phe Gly Asn Ser His Ser Asn Asp Ile Gly Lys Gly
                450                 455                 460
Val Glu Val Leu Ser Leu Thr Pro Ser Phe Met Asp Ile Pro Glu Lys
465                 470                 475                 480
Glu Arg Glu Thr Glu Arg Ser Pro Ser Ser Asn Tyr Ile Thr Asp Arg
                485                 490                 495
Pro Phe Thr Arg Lys Pro Arg Ser Ser Ser Ile Asp Val Asn His Arg
                500                 505                 510
Tyr Pro Pro Met Ala Ser Thr Thr Val Ala Thr Ser Pro Gly Ala Leu
                515                 520                 525
Asn Asn Ala Val Ala Ser Asn Leu Asp Asp Gln Leu Ser Leu Thr Ser
                530                 535                 540
Leu Asn Ser Gln Pro Ser Ser Ile Ala Asn Met Met Met Asp Pro Ser
545                 550                 555                 560
Asn Leu Ala Glu Gln Ser Ser Ile His Ser Val Pro Gln Ser Ile Asn
                565                 570                 575
Ser Pro Arg Met Pro Lys Thr Gly Ser Arg Gln Asp Lys Asn Val His
                580                 585                 590
Thr Lys Lys Glu Glu Arg Asn Pro Leu Asn Asn Ile Tyr Asp Leu Ser
                595                 600                 605
Gln Leu Glu Asn Val Pro Asp Glu Met Asn Gln Met Phe Phe Pro Pro
            610                 615                 620
Leu Lys Ser Met Asn Arg Pro Asp Ala Ile Arg Glu Asn Ser Phe Ser
625                 630                 635                 640
Ser Asn Phe Ile Ile Gln Gly Asn Ser Met Ile Ser Thr Pro Ser Gly
                645                 650                 655
Arg Asn Asp Leu Pro Asp Thr Ser Pro Met Ser Ser Ile Gln Thr Ala
                660                 665                 670
Leu Pro Pro Ser Gln Leu Leu Thr Asp Gln Gly Phe Ala Asp Leu Asp
                675                 680                 685
Asn Phe Met Ser Ser Leu
      690

<210> SEQ ID NO 4
<211> LENGTH: 554
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant mut40
      (TR3mut40), transcriptional activator
```

```
<400> SEQUENCE: 4

Met Val Leu Ile Asn Gly Ile Lys Tyr Ala Cys Glu Arg Cys Ile Arg
  1               5                  10                  15

Gly His Arg Val Thr Thr Cys Asn His Thr Asp Gln Pro Leu Met Met
             20                  25                  30

Ile Lys Pro Lys Gly Arg Pro Ser Thr Thr Cys Asp Tyr Cys Lys Gln
         35                  40                  45

Leu Arg Lys Asn Lys Asn Ala Asn Pro Glu Gly Val Cys Thr Cys Gly
     50                  55                  60

Arg Leu Glu Lys Lys Lys Leu Ala Gln Lys Ala Lys Glu Glu Ala Arg
 65                  70                  75                  80

Val Lys Ala Lys Glu Lys Gln Arg Lys Gln Cys Thr Cys Gly Thr Asp
                 85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
            115                 120                 125

Phe Glu Arg Val Leu Ser Ser Thr Ser Leu Asp Ser Asn Met Leu Ser
        130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Pro Leu Ser Ser Met Ser
        195                 200                 205

Phe Asn Phe Leu Thr Gly Asn Ile Asn Glu Thr Asn Gln Asn His Ser
210                 215                 220

Asn His Gln His Ser Lys Ser Ser Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
            260                 265                 270

Ile Ser Asn Ser Arg Val Gly Glu Val Ser Val Pro Leu Glu Glu Tyr
        275                 280                 285

Ile Pro Ser Asp Ile Asp Gly Val Gly Arg Val Thr Asp Lys Ser Ser
    290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
            340                 345                 350

Asn Gly Asn Gly Met Asn Asn Ser Asn Asn Asn Ile Asn Ser Asn
        355                 360                 365

Gly Asn Asp Lys Asn Asn Asn Ser Ser Arg Gln Glu His Gln Gly
    370                 375                 380

Asn Gly Leu Phe Asp Met Phe Thr Asp Ser Ser Ile Ser Thr Leu
385                 390                 395                 400

Ser Arg Ala Asn Leu Leu Leu Gln Glu Lys Ile Gly Ser Gln Glu Asn
                405                 410                 415
```

```
Ser Val Lys Pro Glu Asn Tyr Ser Lys Asn Pro Gln Leu Arg His Gln
            420                 425                 430

Leu Thr Ser Arg Ser Arg Ser Phe Ile His His Pro Ala Asn Glu Tyr
        435                 440                 445

Leu Lys Asn Thr Phe Gly Asn Ser His Ser Asn Asp Ile Gly Lys Gly
    450                 455                 460

Val Glu Val Leu Ser Leu Thr Pro Ser Phe Met Asp Ile Pro Glu Lys
465                 470                 475                 480

Glu Arg Glu Thr Glu Arg Ser Pro Ser Ser Asn Tyr Ile Thr Asp Arg
                485                 490                 495

Pro Phe Thr Arg Lys Pro Arg Ser Ser Ile Tyr Val Lys His Arg
            500                 505                 510

Tyr Pro Pro Met Ala Pro Thr Thr Val Ala Thr Ser Pro Gly Val Leu
            515                 520                 525

Asn Asn Ala Val Ala Ser Asn Leu Asp Asp Gln Leu Ser Leu Thr Ser
        530                 535                 540

Leu Asn Ser Gln Pro Ser Ser Ile Ala Ile
545                 550

<210> SEQ ID NO 5
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant 440 F->Y,
      transcriptional activator

<400> SEQUENCE: 5

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
            20                  25                  30

Ile Lys Pro Lys Gly Arg Pro Ser Thr Thr Cys Asp Tyr Cys Lys Gln
        35                  40                  45

Leu Arg Lys Asn Lys Asn Ala Asn Pro Glu Gly Val Cys Thr Cys Gly
    50                  55                  60

Arg Leu Glu Lys Lys Leu Ala Gln Lys Ala Lys Glu Glu Ala Arg
65                  70                  75                  80

Val Lys Ala Lys Glu Lys Gln Arg Lys Gln Cys Thr Cys Gly Thr Asp
                85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
        115                 120                 125

Phe Glu Arg Val Leu Ser Ser Thr Ser Leu Asp Ser Asn Met Leu Ser
    130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Pro Leu Ser Ser Met Ser
        195                 200                 205
```

```
Phe Asn Phe Leu Thr Gly Asn Ile Asn Glu Thr Asn Gln Asn His Ser
    210                 215                 220

Asn His Gln His Ser Lys Ser Ser Asn Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
            260                 265                 270

Ile Ser Asn Ser Arg Val Gly Glu Val Ser Val Pro Leu Glu Glu Tyr
        275                 280                 285

Ile Pro Ser Asp Ile Asp Gly Val Gly Arg Val Thr Asp Lys Ser Ser
    290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
            340                 345                 350

Asn Gly Asn Gly Met Asn Asn Ser Asn Asn Asn Ile Asn Ser Asn
        355                 360                 365

Gly Asn Asp Lys Asn Asn Asn Ser Ser Arg Gln Glu His Gln Gly
    370                 375                 380

Asn Gly Leu Phe Asp Met Phe Thr Asp Ser Ser Ser Ile Ser Thr Leu
385                 390                 395                 400

Ser Arg Ala Asn Leu Leu Leu Gln Glu Lys Ile Gly Ser Gln Glu Asn
                405                 410                 415

Ser Val Lys Pro Glu Asn Tyr Ser Lys Asn Pro Gln Leu Arg His Gln
            420                 425                 430

Leu Thr Ser Arg Ser Arg Ser Tyr Ile His His Pro Ala Asn Glu Tyr
        435                 440                 445

Leu Lys Asn Thr Phe Gly Asn Ser His Ser Asn Asp Ile Gly Lys Gly
    450                 455                 460

Val Glu Val Leu Ser Leu Thr Pro Ser Phe Met Asp Ile Pro Glu Lys
465                 470                 475                 480

Glu Arg Glu Thr Glu Arg Ser Pro Ser Ser Asn Tyr Ile Thr Asp Arg
                485                 490                 495

Pro Phe Thr Arg Lys Pro Arg Ser Ser Ser Ile Asp Val Asn His Arg
            500                 505                 510

Tyr Pro Pro Met Ala Pro Thr Thr Val Ala Thr Ser Pro Gly Ala Leu
        515                 520                 525

Asn Asn Ala Val Ala Ser Asn Leu Asp Asp Gln Leu Ser Leu Thr Ser
    530                 535                 540

Leu Asn Ser Gln Pro Ser Ser Ile Ala Asn Met Met Asp Pro Ser
545                 550                 555                 560

Asn Leu Ala Glu Gln Ser Ser Ile His Ser Val Pro Gln Ser Ile Asn
                565                 570                 575

Ser Pro Arg Met Pro Lys Thr Gly Ser Arg Gln Asp Lys Asn Ile His
            580                 585                 590

Thr Lys Lys Glu Glu Arg Asn Pro Leu Asn Asn Ile His Asp Leu Ser
        595                 600                 605

Gln Leu Glu Asn Val Pro Asp Glu Met Asn Gln Met Phe Ser Pro Pro
    610                 615                 620
```

```
Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
            645                 650                 655

Arg Asn Asp Leu Pro Asp Thr Ser Pro Met Ser Ser Ile Gln Thr Ala
        660                 665                 670

Ser Pro Pro Ser Gln Leu Leu Thr Asp Gln Gly Phe Ala Asp Leu Asp
    675                 680                 685

Asn Phe Met Ser Ser Leu
        690

<210> SEQ ID NO 6
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant 508 D->Y,
      transcriptional activator

<400> SEQUENCE: 6

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
            20                  25                  30

Ile Lys Pro Lys Gly Arg Pro Ser Thr Thr Cys Asp Tyr Cys Lys Gln
        35                  40                  45

Leu Arg Lys Asn Lys Asn Ala Asn Pro Glu Gly Val Cys Thr Cys Gly
50                  55                  60

Arg Leu Glu Lys Lys Lys Leu Ala Gln Lys Ala Lys Glu Glu Ala Arg
65                  70                  75                  80

Val Lys Ala Lys Glu Lys Gln Arg Lys Gln Cys Thr Cys Gly Thr Asp
            85                  90                  95

Glu Val Cys Lys Tyr His Ala Gln Lys Arg His Leu Arg Lys Ser Pro
        100                 105                 110

Ser Ser Ser Gln Lys Lys Gly Arg Ser Ile Ser Arg Ser Gln Pro Met
    115                 120                 125

Phe Glu Arg Val Leu Ser Ser Thr Ser Leu Asp Ser Asn Met Leu Ser
130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
            165                 170                 175

Val Pro Ser Leu Ala Ser Ile Ser Ser Leu Gln Ser Ser Gln Ser Leu
        180                 185                 190

Asp Gln Asn Phe Ser Val Pro Gln Ser Pro Pro Leu Ser Ser Met Ser
    195                 200                 205

Phe Asn Phe Leu Thr Gly Asn Ile Asn Glu Thr Asn Gln Asn His Ser
210                 215                 220

Asn His Gln His Ser Lys Ser Ser Asn Asn Trp Gln Asp Ser Ser Val
225                 230                 235                 240

Ser Leu Pro Ala Lys Ala Asp Ser Arg Leu Asn Met Met Asp Lys Asn
            245                 250                 255

Asn Ser Val Gly Leu Asp Leu Leu Gly His Ser Lys Arg Ile Ser Pro
        260                 265                 270
```

```
Ile Ser Asn Ser Arg Val Gly Glu Val Ser Val Pro Leu Glu Glu Tyr
            275                 280                 285
Ile Pro Ser Asp Ile Asp Gly Val Gly Arg Val Thr Asp Lys Ser Ser
290                 295                 300
Leu Val Tyr Asp Trp Pro Phe Asp Glu Ser Ile Glu Arg Asn Phe Ser
305                 310                 315                 320
Thr Thr Ala Thr Ala Ala Thr Gly Glu Ser Lys Phe Asp Ile Asn Asp
                325                 330                 335
Asn Cys Asn Arg Ile Asn Ser Lys Ser Tyr Ser Lys Thr Asn Ser Met
            340                 345                 350
Asn Gly Asn Gly Met Asn Asn Ser Asn Asn Asn Ile Asn Ser Asn
            355                 360                 365
Gly Asn Asp Lys Asn Asn Asn Ser Ser Arg Gln Glu His Gln Gly
    370                 375                 380
Asn Gly Leu Phe Asp Met Phe Thr Asp Ser Ser Ser Ile Ser Thr Leu
385                 390                 395                 400
Ser Arg Ala Asn Leu Leu Leu Gln Glu Lys Ile Gly Ser Gln Glu Asn
            405                 410                 415
Ser Val Lys Pro Glu Asn Tyr Ser Lys Asn Pro Gln Leu Arg His Gln
            420                 425                 430
Leu Thr Ser Arg Ser Arg Ser Phe Ile His His Pro Ala Asn Glu Tyr
            435                 440                 445
Leu Lys Asn Thr Phe Gly Asn Ser His Ser Asn Asp Ile Gly Lys Gly
            450                 455                 460
Val Glu Val Leu Ser Leu Thr Pro Ser Phe Met Asp Ile Pro Glu Lys
465                 470                 475                 480
Glu Arg Glu Thr Glu Arg Ser Pro Ser Ser Asn Tyr Ile Thr Asp Arg
                485                 490                 495
Pro Phe Thr Arg Lys Pro Arg Ser Ser Ser Ile Tyr Val Asn His Arg
            500                 505                 510
Tyr Pro Pro Met Ala Pro Thr Thr Val Ala Thr Ser Pro Gly Ala Leu
            515                 520                 525
Asn Asn Ala Val Ala Ser Asn Leu Asp Asp Gln Leu Ser Leu Thr Ser
    530                 535                 540
Leu Asn Ser Gln Pro Ser Ser Ile Ala Asn Met Met Met Asp Pro Ser
545                 550                 555                 560
Asn Leu Ala Glu Gln Ser Ser Ile His Ser Val Pro Gln Ser Ile Asn
                565                 570                 575
Ser Pro Arg Met Pro Lys Thr Gly Ser Arg Gln Asp Lys Asn Ile His
            580                 585                 590
Thr Lys Lys Glu Glu Arg Asn Pro Leu Asn Asn Ile His Asp Leu Ser
            595                 600                 605
Gln Leu Glu Asn Val Pro Asp Glu Met Asn Gln Met Phe Ser Pro Pro
    610                 615                 620
Leu Lys Ser Met Asn Arg Pro Asp Ala Ile Arg Glu Asn Ser Ser Ser
625                 630                 635                 640
Ser Asn Phe Ile Ile Gln Gly Asn Ser Met Ile Ser Thr Pro Ser Gly
                645                 650                 655
Arg Asn Asp Leu Pro Asp Thr Ser Pro Met Ser Ser Ile Gln Thr Ala
            660                 665                 670
Ser Pro Pro Ser Gln Leu Leu Thr Asp Gln Gly Phe Ala Asp Leu Asp
            675                 680                 685
Asn Phe Met Ser Ser Leu
```

690

<210> SEQ ID NO 7
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant 510 N->K,
      transcriptional activator

<400> SEQUENCE: 7

```
Met Val Leu Ile Asn Gly Ile Lys Tyr Ala Cys Glu Arg Cys Ile Arg
  1               5                  10                  15

Gly His Arg Val Thr Thr Cys Asn His Thr Asp Gln Pro Leu Met Met
             20                  25                  30

Ile Lys Pro Lys Gly Arg Pro Ser Thr Thr Cys Asp Tyr Cys Lys Gln
         35                  40                  45

Leu Arg Lys Asn Lys Asn Ala Asn Pro Glu Gly Val Cys Thr Cys Gly
 50                  55                  60

Arg Leu Glu Lys Lys Leu Ala Gln Lys Ala Lys Glu Glu Ala Arg
 65                  70                  75                  80

Val Lys Ala Lys Glu Lys Gln Arg Lys Gln Cys Thr Cys Gly Thr Asp
                 85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
            115                 120                 125

Phe Glu Arg Val Leu Ser Ser Thr Ser Leu Asp Ser Asn Met Leu Ser
130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Pro Leu Ser Ser Met Ser
            195                 200                 205

Phe Asn Phe Leu Thr Gly Asn Ile Asn Glu Thr Asn Gln Asn His Ser
210                 215                 220

Asn His Gln His Ser Lys Ser Ser Asn Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
            260                 265                 270

Ile Ser Asn Ser Arg Val Gly Glu Val Ser Val Pro Leu Glu Glu Tyr
            275                 280                 285

Ile Pro Ser Asp Ile Asp Gly Val Gly Arg Val Thr Asp Lys Ser Ser
290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
```

```
                    340                 345                 350
Asn Gly Asn Gly Met Asn Asn Ser Asn Asn Asn Ile Asn Ser Asn
            355                 360                 365
Gly Asn Asp Lys Asn Asn Asn Ser Ser Arg Gln Glu His Gln Gly
        370                 375                 380
Asn Gly Leu Phe Asp Met Phe Thr Asp Ser Ser Ile Ser Thr Leu
385                 390                 395                 400
Ser Arg Ala Asn Leu Leu Leu Gln Glu Lys Ile Gly Ser Gln Glu Asn
                405                 410                 415
Ser Val Lys Pro Glu Asn Tyr Ser Lys Asn Pro Gln Leu Arg His Gln
            420                 425                 430
Leu Thr Ser Arg Ser Arg Ser Phe Ile His His Pro Ala Asn Glu Tyr
        435                 440                 445
Leu Lys Asn Thr Phe Gly Asn Ser His Ser Asn Asp Ile Gly Lys Gly
    450                 455                 460
Val Glu Val Leu Ser Leu Thr Pro Ser Phe Met Asp Ile Pro Glu Lys
465                 470                 475                 480
Glu Arg Glu Thr Glu Arg Ser Pro Ser Ser Asn Tyr Ile Thr Asp Arg
                485                 490                 495
Pro Phe Thr Arg Lys Pro Arg Ser Ser Ser Ile Asp Val Lys His Arg
            500                 505                 510
Tyr Pro Pro Met Ala Pro Thr Thr Val Ala Thr Ser Pro Gly Ala Leu
        515                 520                 525
Asn Asn Ala Val Ala Ser Asn Leu Asp Asp Gln Leu Ser Leu Thr Ser
    530                 535                 540
Leu Asn Ser Gln Pro Ser Ser Ile Ala Asn Met Met Met Asp Pro Ser
545                 550                 555                 560
Asn Leu Ala Glu Gln Ser Ser Ile His Ser Val Pro Gln Ser Ile Asn
                565                 570                 575
Ser Pro Arg Met Pro Lys Thr Gly Ser Arg Gln Asp Lys Asn Ile His
            580                 585                 590
Thr Lys Lys Glu Glu Arg Asn Pro Leu Asn Asn Ile His Asp Leu Ser
        595                 600                 605
Gln Leu Glu Asn Val Pro Asp Glu Met Asn Gln Met Phe Ser Pro Pro
    610                 615                 620
Leu Lys Ser Met Asn Arg Pro Asp Ala Ile Arg Glu Asn Ser Ser Ser
625                 630                 635                 640
Ser Asn Phe Ile Ile Gln Gly Asn Ser Met Ile Ser Thr Pro Ser Gly
                645                 650                 655
Arg Asn Asp Leu Pro Asp Thr Ser Pro Met Ser Ser Ile Gln Thr Ala
            660                 665                 670
Ser Pro Pro Ser Gln Leu Leu Thr Asp Gln Gly Phe Ala Asp Leu Asp
        675                 680                 685
Asn Phe Met Ser Ser Leu
    690

<210> SEQ ID NO 8
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant 518 P->S,
      transcriptional activator
```

<400> SEQUENCE: 8

```
Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
            20                  25                  30

Ile Lys Pro Lys Gly Arg Pro Ser Thr Thr Cys Asp Tyr Cys Lys Gln
        35                  40                  45

Leu Arg Lys Asn Lys Asn Ala Asn Pro Glu Gly Val Cys Thr Cys Gly
    50                  55                  60

Arg Leu Glu Lys Lys Lys Leu Ala Gln Lys Ala Lys Glu Glu Ala Arg
65                  70                  75                  80

Val Lys Ala Lys Glu Lys Gln Arg Lys Gln Cys Thr Cys Gly Thr Asp
                85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
        115                 120                 125

Phe Glu Arg Val Leu Ser Ser Thr Ser Leu Asp Ser Asn Met Leu Ser
    130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Pro Leu Ser Ser Met Ser
        195                 200                 205

Phe Asn Phe Leu Thr Gly Asn Ile Asn Glu Thr Asn Gln Asn His Ser
    210                 215                 220

Asn His Gln His Ser Lys Ser Ser Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
            260                 265                 270

Ile Ser Asn Ser Arg Val Gly Glu Val Ser Val Pro Leu Glu Glu Tyr
        275                 280                 285

Ile Pro Ser Asp Ile Asp Gly Val Gly Arg Val Thr Asp Lys Ser Ser
    290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
            340                 345                 350

Asn Gly Asn Gly Met Asn Asn Ser Asn Asn Asn Ile Asn Ser Asn
        355                 360                 365

Gly Asn Asp Lys Asn Asn Asn Ser Ser Arg Gln Glu His Gln Gly
    370                 375                 380

Asn Gly Leu Phe Asp Met Phe Thr Asp Ser Ser Ile Ser Thr Leu
385                 390                 395                 400

Ser Arg Ala Asn Leu Leu Leu Gln Glu Lys Ile Gly Ser Gln Glu Asn
                405                 410                 415
```

Ser Val Lys Pro Glu Asn Tyr Ser Lys Asn Pro Gln Leu Arg His Gln
            420                 425                 430

Leu Thr Ser Arg Ser Arg Ser Phe Ile His His Pro Ala Asn Glu Tyr
        435                 440                 445

Leu Lys Asn Thr Phe Gly Asn Ser His Ser Asn Asp Ile Gly Lys Gly
    450                 455                 460

Val Glu Val Leu Ser Leu Thr Pro Ser Phe Met Asp Ile Pro Glu Lys
465                 470                 475                 480

Glu Arg Glu Thr Glu Arg Ser Pro Ser Ser Asn Tyr Ile Thr Asp Arg
                485                 490                 495

Pro Phe Thr Arg Lys Pro Arg Ser Ser Ile Asp Val Asn His Arg
            500                 505                 510

Tyr Pro Pro Met Ala Ser Thr Thr Val Ala Thr Ser Pro Gly Ala Leu
        515                 520                 525

Asn Asn Ala Val Ala Ser Asn Leu Asp Asp Gln Leu Ser Leu Thr Ser
    530                 535                 540

Leu Asn Ser Gln Pro Ser Ser Ile Ala Asn Met Met Met Asp Pro Ser
545                 550                 555                 560

Asn Leu Ala Glu Gln Ser Ser Ile His Ser Val Pro Gln Ser Ile Asn
                565                 570                 575

Ser Pro Arg Met Pro Lys Thr Gly Ser Arg Gln Asp Lys Asn Ile His
            580                 585                 590

Thr Lys Lys Glu Glu Arg Asn Pro Leu Asn Asn Ile His Asp Leu Ser
        595                 600                 605

Gln Leu Glu Asn Val Pro Asp Glu Met Asn Gln Met Phe Ser Pro Pro
    610                 615                 620

Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
                645                 650                 655

Arg Asn Asp Leu Pro Asp Thr Ser Pro Met Ser Ser Ile Gln Thr Ala
            660                 665                 670

Ser Pro Pro Ser Gln Leu Leu Thr Asp Gln Gly Phe Ala Asp Leu Asp
        675                 680                 685

Asn Phe Met Ser Ser Leu
    690

<210> SEQ ID NO 9
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant 527 A->V,
      transcriptional activator

<400> SEQUENCE: 9

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
            20                  25                  30

Ile Lys Pro Lys Gly Arg Pro Ser Thr Thr Cys Asp Tyr Cys Lys Gln
        35                  40                  45

Leu Arg Lys Asn Lys Asn Ala Asn Pro Glu Gly Val Cys Thr Cys Gly
    50                  55                  60

```
Arg Leu Glu Lys Lys Lys Leu Ala Gln Lys Ala Lys Glu Glu Ala Arg
 65                  70                  75                  80

Val Lys Ala Lys Glu Lys Gln Arg Lys Gln Cys Thr Cys Gly Thr Asp
             85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
        115                 120                 125

Phe Glu Arg Val Leu Ser Ser Thr Ser Leu Asp Ser Asn Met Leu Ser
        130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Leu Ser Ser Met Ser
        195                 200                 205

Phe Asn Phe Leu Thr Gly Asn Ile Asn Glu Thr Asn Gln Asn His Ser
210                 215                 220

Asn His Gln His Ser Lys Ser Ser Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
            260                 265                 270

Ile Ser Asn Ser Arg Val Gly Glu Val Ser Val Pro Leu Glu Glu Tyr
        275                 280                 285

Ile Pro Ser Asp Ile Asp Gly Val Gly Arg Val Thr Asp Lys Ser Ser
        290                 295                 300

Leu Val Tyr Asp Trp Pro Phe Asp Glu Ser Ile Glu Arg Asn Phe Ser
305                 310                 315                 320

Thr Thr Ala Thr Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
            340                 345                 350

Asn Gly Asn Gly Met Asn Asn Ser Asn Asn Asn Ile Asn Ser Asn
        355                 360                 365

Gly Asn Asp Lys Asn Asn Asn Ser Ser Arg Gln Glu His Gln Gly
        370                 375                 380

Asn Gly Leu Phe Asp Met Phe Thr Asp Ser Ser Ser Ile Ser Thr Leu
385                 390                 395                 400

Ser Arg Ala Asn Leu Leu Leu Gln Glu Lys Ile Gly Ser Gln Glu Asn
                405                 410                 415

Ser Val Lys Pro Glu Asn Tyr Ser Lys Asn Pro Gln Leu Arg His Gln
            420                 425                 430

Leu Thr Ser Arg Ser Arg Ser Phe Ile His Pro Ala Asn Glu Tyr
        435                 440                 445

Leu Lys Asn Thr Phe Gly Asn Ser His Ser Asn Asp Ile Gly Lys Gly
    450                 455                 460

Val Glu Val Leu Ser Leu Thr Pro Ser Phe Met Asp Ile Pro Glu Lys
465                 470                 475                 480
```

```
Glu Arg Glu Thr Glu Arg Ser Pro Ser Ser Asn Tyr Ile Thr Asp Arg
                485                 490                 495

Pro Phe Thr Arg Lys Pro Arg Ser Ser Ser Ile Asp Val Asn His Arg
                500                 505                 510

Tyr Pro Pro Met Ala Pro Thr Thr Val Ala Thr Ser Pro Gly Val Leu
                515                 520                 525

Asn Asn Ala Val Ala Ser Asn Leu Asp Asp Gln Leu Ser Leu Thr Ser
                530                 535                 540

Leu Asn Ser Gln Pro Ser Ser Ile Ala Asn Met Met Asp Pro Ser
545                 550                 555                 560

Asn Leu Ala Glu Gln Ser Ser Ile His Ser Val Pro Gln Ser Ile Asn
                565                 570                 575

Ser Pro Arg Met Pro Lys Thr Gly Ser Arg Gln Asp Lys Asn Ile His
                580                 585                 590

Thr Lys Lys Glu Glu Arg Asn Pro Leu Asn Asn Ile His Asp Leu Ser
                595                 600                 605

Gln Leu Glu Asn Val Pro Asp Glu Met Asn Gln Met Phe Ser Pro Pro
                610                 615                 620

Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
                645                 650                 655

Arg Asn Asp Leu Pro Asp Thr Ser Pro Met Ser Ser Ile Gln Thr Ala
                660                 665                 670

Ser Pro Pro Ser Gln Leu Leu Thr Asp Gln Gly Phe Ala Asp Leu Asp
                675                 680                 685

Asn Phe Met Ser Ser Leu
                690

<210> SEQ ID NO 10
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant 554 N->I,
      transcriptional activator

<400> SEQUENCE: 10

Met Val Leu Ile Asn Gly Ile Lys Tyr Ala Cys Glu Arg Cys Ile Arg
  1               5                  10                  15

Gly His Arg Val Thr Thr Cys Asn His Thr Asp Gln Pro Leu Met Met
                 20                  25                  30

Ile Lys Pro Lys Gly Arg Pro Ser Thr Thr Cys Asp Tyr Cys Lys Gln
             35                  40                  45

Leu Arg Lys Asn Lys Asn Ala Asn Pro Glu Gly Val Cys Thr Cys Gly
         50                  55                  60

Arg Leu Glu Lys Lys Lys Leu Ala Gln Lys Lys Glu Glu Ala Arg
 65                  70                  75                  80

Val Lys Ala Lys Glu Lys Gln Arg Lys Gln Cys Thr Cys Gly Thr Asp
                 85                  90                  95

Glu Val Cys Lys Tyr His Ala Gln Lys Arg His Leu Arg Lys Ser Pro
                100                 105                 110

Ser Ser Ser Gln Lys Lys Gly Arg Ser Ile Ser Arg Ser Gln Pro Met
            115                 120                 125
```

```
Phe Glu Arg Val Leu Ser Ser Thr Ser Leu Asp Ser Asn Met Leu Ser
130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Pro Leu Ser Ser Met Ser
            195                 200                 205

Phe Asn Phe Leu Thr Gly Asn Ile Asn Glu Thr Asn Gln Asn His Ser
210                 215                 220

Asn His Gln His Ser Lys Ser Ser Asn Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
            260                 265                 270

Ile Ser Asn Ser Arg Val Gly Glu Val Ser Val Pro Leu Glu Glu Tyr
        275                 280                 285

Ile Pro Ser Asp Ile Asp Gly Val Gly Arg Val Thr Asp Lys Ser Ser
290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
            340                 345                 350

Asn Gly Asn Gly Met Asn Asn Ser Asn Asn Asn Ile Asn Ser Asn
        355                 360                 365

Gly Asn Asp Lys Asn Asn Asn Ser Ser Arg Gln Glu His Gln Gly
370                 375                 380

Asn Gly Leu Phe Asp Met Phe Thr Asp Ser Ser Ser Ile Ser Thr Leu
385                 390                 395                 400

Ser Arg Ala Asn Leu Leu Leu Gln Glu Lys Ile Gly Ser Gln Glu Asn
            405                 410                 415

Ser Val Lys Pro Glu Asn Tyr Ser Lys Asn Pro Gln Leu Arg His Gln
            420                 425                 430

Leu Thr Ser Arg Ser Arg Ser Phe Ile His His Pro Ala Asn Glu Tyr
        435                 440                 445

Leu Lys Asn Thr Phe Gly Asn Ser His Ser Asn Asp Ile Gly Lys Gly
    450                 455                 460

Val Glu Val Leu Ser Leu Thr Pro Ser Phe Met Asp Ile Pro Glu Lys
465                 470                 475                 480

Glu Arg Glu Thr Glu Arg Ser Pro Ser Ser Asn Tyr Ile Thr Asp Arg
                485                 490                 495

Pro Phe Thr Arg Lys Pro Arg Ser Ser Ser Ile Asp Val Asn His Arg
            500                 505                 510

Tyr Pro Pro Met Ala Pro Thr Val Ala Thr Ser Pro Gly Ala Leu
        515                 520                 525

Asn Asn Ala Val Ala Ser Asn Leu Asp Asp Gln Leu Ser Leu Thr Ser
530                 535                 540

Leu Asn Ser Gln Pro Ser Ser Ile Ala Ile Met Met Met Asp Pro Ser
```

-continued

```
                545                 550                 555                 560
Asn Leu Ala Glu Gln Ser Ser Ile His Ser Val Pro Gln Ser Ile Asn
                    565                 570                 575

Ser Pro Arg Met Pro Lys Thr Gly Ser Arg Gln Asp Lys Asn Ile His
                580                 585                 590

Thr Lys Lys Glu Glu Arg Asn Pro Leu Asn Asn Ile His Asp Leu Ser
            595                 600                 605

Gln Leu Glu Asn Val Pro Asp Glu Met Asn Gln Met Phe Ser Pro Pro
        610                 615                 620

Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
                645                 650                 655

Arg Asn Asp Leu Pro Asp Thr Ser Pro Met Ser Ser Ile Gln Thr Ala
            660                 665                 670

Ser Pro Pro Ser Gln Leu Leu Thr Asp Gln Gly Phe Ala Asp Leu Asp
        675                 680                 685

Asn Phe Met Ser Ser Leu
        690

<210> SEQ ID NO 11
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant 591 I->V,
      transcriptional activator

<400> SEQUENCE: 11

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
                20                  25                  30

Ile Lys Pro Lys Gly Arg Pro Ser Thr Thr Cys Asp Tyr Cys Lys Gln
            35                  40                  45

Leu Arg Lys Asn Lys Asn Ala Asn Pro Glu Gly Val Cys Thr Cys Gly
        50                  55                  60

Arg Leu Glu Lys Lys Lys Leu Ala Gln Lys Ala Lys Glu Glu Ala Arg
65                  70                  75                  80

Val Lys Ala Lys Glu Lys Gln Arg Lys Gln Cys Thr Cys Gly Thr Asp
                85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
        115                 120                 125

Phe Glu Arg Val Leu Ser Ser Thr Ser Leu Asp Ser Asn Met Leu Ser
        130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Pro Leu Ser Ser Met Ser
```

-continued

```
            195                 200                 205
Phe Asn Phe Leu Thr Gly Asn Ile Asn Glu Thr Asn Gln Asn His Ser
210                 215                 220
Asn His Gln His Ser Lys Ser Ser Asn Trp Gln Asp Ser Ser Val
225                 230                 235                 240
Ser Leu Pro Ala Lys Ala Asp Ser Arg Leu Asn Met Met Asp Lys Asn
                245                 250                 255
Asn Ser Val Gly Leu Asp Leu Leu Gly His Ser Lys Arg Ile Ser Pro
            260                 265                 270
Ile Ser Asn Ser Arg Val Gly Glu Val Ser Val Pro Leu Glu Glu Tyr
        275                 280                 285
Ile Pro Ser Asp Ile Asp Gly Val Gly Arg Val Thr Asp Lys Ser Ser
    290                 295                 300
Leu Val Tyr Asp Trp Pro Phe Asp Glu Ser Ile Glu Arg Asn Phe Ser
305                 310                 315                 320
Thr Thr Ala Thr Ala Ala Thr Gly Glu Ser Lys Phe Asp Ile Asn Asp
                325                 330                 335
Asn Cys Asn Arg Ile Asn Ser Lys Ser Tyr Ser Lys Thr Asn Ser Met
            340                 345                 350
Asn Gly Asn Gly Met Asn Asn Ser Asn Asn Asn Ile Asn Ser Asn
        355                 360                 365
Gly Asn Asp Lys Asn Asn Asn Ser Ser Arg Gln Glu His Gln Gly
370                 375                 380
Asn Gly Leu Phe Asp Met Phe Thr Asp Ser Ser Ser Ile Ser Thr Leu
385                 390                 395                 400
Ser Arg Ala Asn Leu Leu Leu Gln Glu Lys Ile Gly Ser Gln Glu Asn
                405                 410                 415
Ser Val Lys Pro Glu Asn Tyr Ser Lys Asn Pro Gln Leu Arg His Gln
            420                 425                 430
Leu Thr Ser Arg Ser Arg Ser Phe Ile His His Pro Ala Asn Glu Tyr
        435                 440                 445
Leu Lys Asn Thr Phe Gly Asn Ser His Ser Asn Asp Ile Gly Lys Gly
    450                 455                 460
Val Glu Val Leu Ser Leu Thr Pro Ser Phe Met Asp Ile Pro Glu Lys
465                 470                 475                 480
Glu Arg Glu Thr Glu Arg Ser Pro Ser Asn Tyr Ile Thr Asp Arg
                485                 490                 495
Pro Phe Thr Arg Lys Pro Arg Ser Ser Ser Ile Asp Val Asn His Arg
            500                 505                 510
Tyr Pro Pro Met Ala Pro Thr Thr Val Ala Thr Ser Pro Gly Ala Leu
        515                 520                 525
Asn Asn Ala Val Ala Ser Leu Asp Asp Gln Leu Ser Leu Thr Ser
    530                 535                 540
Leu Asn Ser Gln Pro Ser Ser Ile Ala Asn Met Met Asp Pro Ser
545                 550                 555                 560
Asn Leu Ala Glu Gln Ser Ser Ile His Ser Val Pro Gln Ser Ile Asn
                565                 570                 575
Ser Pro Arg Met Pro Lys Thr Gly Ser Arg Gln Asp Lys Asn Val His
            580                 585                 590
Thr Lys Lys Glu Glu Arg Asn Pro Leu Asn Asn Ile His Asp Leu Ser
        595                 600                 605
Gln Leu Glu Asn Val Pro Asp Glu Met Asn Gln Met Phe Ser Pro Pro
    610                 615                 620
```

Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
            645                 650                 655

Arg Asn Asp Leu Pro Asp Thr Ser Pro Met Ser Ile Gln Thr Ala
        660                 665                 670

Ser Pro Pro Ser Gln Leu Leu Thr Asp Gln Gly Phe Ala Asp Leu Asp
            675                 680                 685

Asn Phe Met Ser Ser Leu
        690

<210> SEQ ID NO 12
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant 605 H->Y,
      transcriptional activator

<400> SEQUENCE: 12

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
                20                  25                  30

Ile Lys Pro Lys Gly Arg Pro Ser Thr Thr Cys Asp Tyr Cys Lys Gln
            35                  40                  45

Leu Arg Lys Asn Lys Asn Ala Asn Pro Glu Gly Val Cys Thr Cys Gly
    50                  55                  60

Arg Leu Glu Lys Lys Lys Leu Ala Gln Lys Ala Lys Glu Glu Ala Arg
65                  70                  75                  80

Val Lys Ala Lys Glu Lys Gln Arg Lys Gln Cys Thr Cys Gly Thr Asp
                85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
        115                 120                 125

Phe Glu Arg Val Leu Ser Ser Thr Ser Leu Asp Ser Asn Met Leu Ser
    130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Leu Ser Ser Met Ser
        195                 200                 205

Phe Asn Phe Leu Thr Gly Asn Ile Asn Glu Thr Asn Gln Asn His Ser
    210                 215                 220

Asn His Gln His Ser Lys Ser Ser Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
            260                 265                 270

-continued

```
Ile Ser Asn Ser Arg Val Gly Glu Val Ser Val Pro Leu Glu Glu Tyr
        275                 280                 285

Ile Pro Ser Asp Ile Asp Gly Val Gly Arg Val Thr Asp Lys Ser Ser
290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
                340                 345                 350

Asn Gly Asn Gly Met Asn Asn Ser Asn Asn Asn Ile Asn Ser Asn
        355                 360                 365

Gly Asn Asp Lys Asn Asn Asn Ser Ser Arg Gln Glu His Gln Gly
    370                 375                 380

Asn Gly Leu Phe Asp Met Phe Thr Asp Ser Ser Ser Ile Ser Thr Leu
385                 390                 395                 400

Ser Arg Ala Asn Leu Leu Gln Glu Lys Ile Gly Ser Gln Glu Asn
                405                 410                 415

Ser Val Lys Pro Glu Asn Tyr Ser Lys Asn Pro Gln Leu Arg His Gln
        420                 425                 430

Leu Thr Ser Arg Ser Arg Ser Phe Ile His His Pro Ala Asn Glu Tyr
        435                 440                 445

Leu Lys Asn Thr Phe Gly Asn Ser His Ser Asn Asp Ile Gly Lys Gly
    450                 455                 460

Val Glu Val Leu Ser Leu Thr Pro Ser Phe Met Asp Ile Pro Glu Lys
465                 470                 475                 480

Glu Arg Glu Thr Glu Arg Ser Pro Ser Ser Asn Tyr Ile Thr Asp Arg
                485                 490                 495

Pro Phe Thr Arg Lys Pro Arg Ser Ser Ser Ile Asp Val Asn His Arg
                500                 505                 510

Tyr Pro Pro Met Ala Pro Thr Thr Val Ala Thr Ser Pro Gly Ala Leu
        515                 520                 525

Asn Asn Ala Val Ala Ser Asn Leu Asp Asp Gln Leu Ser Leu Thr Ser
530                 535                 540

Leu Asn Ser Gln Pro Ser Ser Ile Ala Asn Met Met Met Asp Pro Ser
545                 550                 555                 560

Asn Leu Ala Glu Gln Ser Ser Ile His Ser Val Pro Gln Ser Ile Asn
                565                 570                 575

Ser Pro Arg Met Pro Lys Thr Gly Ser Arg Gln Asp Lys Asn Ile His
                580                 585                 590

Thr Lys Lys Glu Glu Arg Asn Pro Leu Asn Asn Ile Tyr Asp Leu Ser
        595                 600                 605

Gln Leu Glu Asn Val Pro Asp Glu Met Asn Gln Met Phe Ser Pro Pro
610                 615                 620

Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
                645                 650                 655

Arg Asn Asp Leu Pro Asp Thr Ser Pro Met Ser Ser Ile Gln Thr Ala
                660                 665                 670

Ser Pro Pro Ser Gln Leu Leu Thr Asp Gln Gly Phe Ala Asp Leu Asp
        675                 680                 685
```

Asn Phe Met Ser Ser Leu
    690

<210> SEQ ID NO 13
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant 622 S->F,
      transcriptional activator

<400> SEQUENCE: 13

Met Val Leu Ile Asn Gly Ile Lys Tyr Ala Cys Glu Arg Cys Ile Arg
 1               5                   10                  15

Gly His Arg Val Thr Thr Cys Asn His Thr Asp Gln Pro Leu Met Met
                20                  25                  30

Ile Lys Pro Lys Gly Arg Pro Ser Thr Thr Cys Asp Tyr Cys Lys Gln
            35                  40                  45

Leu Arg Lys Asn Lys Asn Ala Asn Pro Glu Gly Val Cys Thr Cys Gly
    50                  55                  60

Arg Leu Glu Lys Lys Leu Ala Gln Lys Ala Lys Glu Glu Ala Arg
65                  70                  75                  80

Val Lys Ala Lys Glu Lys Gln Arg Lys Gln Cys Thr Cys Gly Thr Asp
                85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
            115                 120                 125

Phe Glu Arg Val Leu Ser Ser Thr Ser Leu Asp Ser Asn Met Leu Ser
    130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Leu Ser Ser Met Ser
    195                 200                 205

Phe Asn Phe Leu Thr Gly Asn Ile Asn Glu Thr Asn Gln Asn His Ser
210                 215                 220

Asn His Gln His Ser Lys Ser Asn Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
            260                 265                 270

Ile Ser Asn Ser Arg Val Gly Glu Val Ser Val Pro Leu Glu Glu Tyr
        275                 280                 285

Ile Pro Ser Asp Ile Asp Gly Val Gly Arg Val Thr Asp Lys Ser Ser
    290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

-continued

```
Asn Cys Asn Arg Ile Asn Ser Lys Ser Tyr Ser Lys Thr Asn Ser Met
                340                 345                 350
Asn Gly Asn Gly Met Asn Asn Ser Asn Asn Asn Ile Asn Ser Asn
            355                 360                 365
Gly Asn Asp Lys Asn Asn Asn Ser Ser Arg Gln Glu His Gln Gly
        370                 375                 380
Asn Gly Leu Phe Asp Met Phe Thr Asp Ser Ser Ser Ile Ser Thr Leu
385                 390                 395                 400
Ser Arg Ala Asn Leu Leu Gln Glu Lys Ile Gly Ser Gln Glu Asn
                405                 410                 415
Ser Val Lys Pro Glu Asn Tyr Ser Lys Asn Pro Gln Leu Arg His Gln
                420                 425                 430
Leu Thr Ser Arg Ser Arg Ser Phe Ile His His Pro Ala Asn Glu Tyr
            435                 440                 445
Leu Lys Asn Thr Phe Gly Asn Ser His Ser Asn Asp Ile Gly Lys Gly
        450                 455                 460
Val Glu Val Leu Ser Leu Thr Pro Ser Phe Met Asp Ile Pro Glu Lys
465                 470                 475                 480
Glu Arg Glu Thr Glu Arg Ser Pro Ser Ser Asn Tyr Ile Thr Asp Arg
                485                 490                 495
Pro Phe Thr Arg Lys Pro Arg Ser Ser Ser Ile Asp Val Asn His Arg
                500                 505                 510
Tyr Pro Pro Met Ala Pro Thr Thr Val Ala Thr Ser Pro Gly Ala Leu
            515                 520                 525
Asn Asn Ala Val Ala Ser Asn Leu Asp Asp Gln Leu Ser Leu Thr Ser
        530                 535                 540
Leu Asn Ser Gln Pro Ser Ser Ile Ala Asn Met Met Met Asp Pro Ser
545                 550                 555                 560
Asn Leu Ala Glu Gln Ser Ser Ile His Ser Val Pro Gln Ser Ile Asn
                565                 570                 575
Ser Pro Arg Met Pro Lys Thr Gly Ser Arg Gln Asp Lys Asn Ile His
                580                 585                 590
Thr Lys Lys Glu Glu Arg Asn Pro Leu Asn Asn Ile His Asp Leu Ser
            595                 600                 605
Gln Leu Glu Asn Val Pro Asp Glu Met Asn Gln Met Phe Phe Pro Pro
        610                 615                 620
Leu Lys Ser Met Asn Arg Pro Asp Ala Ile Arg Glu Asn Ser Ser Ser
625                 630                 635                 640
Ser Asn Phe Ile Ile Gln Gly Asn Ser Met Ile Ser Thr Pro Ser Gly
                645                 650                 655
Arg Asn Asp Leu Pro Asp Thr Ser Pro Met Ser Ser Ile Gln Thr Ala
                660                 665                 670
Ser Pro Pro Ser Gln Leu Leu Thr Asp Gln Gly Phe Ala Asp Leu Asp
            675                 680                 685
Asn Phe Met Ser Ser Leu
        690
```

<210> SEQ ID NO 14
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant 639 S->F,
      transcriptional activator

<400> SEQUENCE: 14

```
Met Val Leu Ile Asn Gly Ile Lys Tyr Ala Cys Glu Arg Cys Ile Arg
 1               5                  10                  15

Gly His Arg Val Thr Thr Cys Asn His Thr Asp Gln Pro Leu Met Met
            20                  25                  30

Ile Lys Pro Lys Gly Arg Pro Ser Thr Thr Cys Asp Tyr Cys Lys Gln
        35                  40                  45

Leu Arg Lys Asn Lys Asn Ala Asn Pro Glu Gly Val Cys Thr Cys Gly
    50                  55                  60

Arg Leu Glu Lys Lys Leu Ala Gln Lys Ala Lys Glu Glu Ala Arg
65                  70                  75                  80

Val Lys Ala Lys Glu Lys Gln Arg Lys Gln Cys Thr Cys Gly Thr Asp
                85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
        115                 120                 125

Phe Glu Arg Val Leu Ser Ser Thr Ser Leu Asp Ser Asn Met Leu Ser
    130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Leu Ser Ser Met Ser
        195                 200                 205

Phe Asn Phe Leu Thr Gly Asn Ile Asn Glu Thr Asn Gln Asn His Ser
    210                 215                 220

Asn His Gln His Ser Lys Ser Ser Asn Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
            260                 265                 270

Ile Ser Asn Ser Arg Val Gly Glu Val Ser Val Pro Leu Glu Glu Tyr
        275                 280                 285

Ile Pro Ser Asp Ile Asp Gly Val Gly Arg Val Thr Asp Lys Ser Ser
    290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Asn Ser Met
            340                 345                 350

Asn Gly Asn Gly Met Asn Asn Ser Asn Asn Asn Ile Asn Ser Asn
        355                 360                 365

Gly Asn Asp Lys Asn Asn Asn Ser Arg Gln Glu His Gln Gly
    370                 375                 380

Asn Gly Leu Phe Asp Met Phe Thr Asp Ser Ser Ser Ile Ser Thr Leu
385                 390                 395                 400

Ser Arg Ala Asn Leu Leu Leu Gln Glu Lys Ile Gly Ser Gln Glu Asn
```

```
                405                 410                 415
Ser Val Lys Pro Glu Asn Tyr Ser Lys Asn Pro Gln Leu Arg His Gln
            420                 425                 430

Leu Thr Ser Arg Ser Arg Ser Phe Ile His His Pro Ala Asn Glu Tyr
            435                 440                 445

Leu Lys Asn Thr Phe Gly Asn Ser His Ser Asn Asp Ile Gly Lys Gly
            450                 455                 460

Val Glu Val Leu Ser Leu Thr Pro Ser Phe Met Asp Ile Pro Glu Lys
465                 470                 475                 480

Glu Arg Glu Thr Glu Arg Ser Pro Ser Ser Asn Tyr Ile Thr Asp Arg
            485                 490                 495

Pro Phe Thr Arg Lys Pro Arg Ser Ser Ile Asp Val Asn His Arg
            500                 505                 510

Tyr Pro Pro Met Ala Pro Thr Thr Val Ala Thr Ser Pro Gly Ala Leu
            515                 520                 525

Asn Asn Ala Val Ala Ser Asn Leu Asp Asp Gln Leu Ser Leu Thr Ser
            530                 535                 540

Leu Asn Ser Gln Pro Ser Ser Ile Ala Asn Met Met Met Asp Pro Ser
545                 550                 555                 560

Asn Leu Ala Glu Gln Ser Ser Ile His Ser Val Pro Gln Ser Ile Asn
            565                 570                 575

Ser Pro Arg Met Pro Lys Thr Gly Ser Arg Gln Asp Lys Asn Ile His
            580                 585                 590

Thr Lys Lys Glu Glu Arg Asn Pro Leu Asn Asn Ile His Asp Leu Ser
            595                 600                 605

Gln Leu Glu Asn Val Pro Asp Glu Met Asn Gln Met Phe Ser Pro Pro
            610                 615                 620

Leu Lys Ser Met Asn Arg Pro Asp Ala Ile Arg Glu Asn Ser Phe Ser
625                 630                 635                 640

Ser Asn Phe Ile Ile Gln Gly Asn Ser Met Ile Ser Thr Pro Ser Gly
            645                 650                 655

Arg Asn Asp Leu Pro Asp Thr Ser Pro Met Ser Ser Ile Gln Thr Ala
            660                 665                 670

Ser Pro Pro Ser Gln Leu Leu Thr Asp Gln Gly Phe Ala Asp Leu Asp
            675                 680                 685

Asn Phe Met Ser Ser Leu
            690

<210> SEQ ID NO 15
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant 673 S->L,
      transcriptional activator

<400> SEQUENCE: 15

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
            20                  25                  30

Ile Lys Pro Lys Gly Arg Pro Ser Thr Thr Cys Asp Tyr Cys Lys Gln
            35                  40                  45

Leu Arg Lys Asn Lys Asn Ala Asn Pro Glu Gly Val Cys Thr Cys Gly
```

-continued

```
                50                  55                  60
Arg Leu Glu Lys Lys Lys Leu Ala Gln Lys Ala Lys Glu Glu Ala Arg
 65                  70                  75                  80

Val Lys Ala Lys Glu Lys Gln Arg Lys Gln Cys Thr Cys Gly Thr Asp
                 85                  90                  95

Glu Val Cys Lys Tyr His Ala Gln Lys Arg His Leu Arg Lys Ser Pro
                100                 105                 110

Ser Ser Ser Gln Lys Lys Gly Arg Ser Ile Ser Arg Ser Gln Pro Met
                115                 120                 125

Phe Glu Arg Val Leu Ser Ser Thr Ser Leu Asp Ser Asn Met Leu Ser
                130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
                180                 185                 190

Asp Gln Asn Phe Ser Val Pro Gln Ser Pro Leu Ser Ser Met Ser
                195                 200                 205

Phe Asn Phe Leu Thr Gly Asn Ile Asn Glu Thr Asn Gln Asn His Ser
                210                 215                 220

Asn His Gln His Ser Lys Ser Ser Asn Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
                260                 265                 270

Ile Ser Asn Ser Arg Val Gly Glu Val Ser Val Pro Leu Glu Glu Tyr
                275                 280                 285

Ile Pro Ser Asp Ile Asp Gly Val Gly Arg Val Thr Asp Lys Ser Ser
                290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
                340                 345                 350

Asn Gly Asn Gly Met Asn Asn Ser Asn Asn Asn Ile Asn Ser Asn
                355                 360                 365

Gly Asn Asp Lys Asn Asn Asn Ser Ser Arg Gln Glu His Gln Gly
                370                 375                 380

Asn Gly Leu Phe Asp Met Phe Thr Asp Ser Ser Ser Ile Ser Thr Leu
385                 390                 395                 400

Ser Arg Ala Asn Leu Leu Leu Gln Glu Lys Ile Gly Ser Gln Glu Asn
                405                 410                 415

Ser Val Lys Pro Glu Asn Tyr Ser Lys Asn Pro Gln Leu Arg His Gln
                420                 425                 430

Leu Thr Ser Arg Ser Arg Ser Phe Ile His His Pro Ala Asn Glu Tyr
                435                 440                 445

Leu Lys Asn Thr Phe Gly Asn Ser His Ser Asn Asp Ile Gly Lys Gly
                450                 455                 460

Val Glu Val Leu Ser Leu Thr Pro Ser Phe Met Asp Ile Pro Glu Lys
465                 470                 475                 480
```

-continued

```
Glu Arg Glu Thr Glu Arg Ser Pro Ser Ser Asn Tyr Ile Thr Asp Arg
            485                 490                 495

Pro Phe Thr Arg Lys Pro Arg Ser Ser Ile Asp Val Asn His Arg
        500                 505                 510

Tyr Pro Pro Met Ala Pro Thr Val Ala Thr Ser Pro Gly Ala Leu
        515                 520                 525

Asn Asn Ala Val Ala Ser Asn Leu Asp Asp Gln Leu Ser Leu Thr Ser
    530                 535                 540

Leu Asn Ser Gln Pro Ser Ser Ile Ala Asn Met Met Met Asp Pro Ser
545                 550                 555                 560

Asn Leu Ala Glu Gln Ser Ser Ile His Ser Val Pro Gln Ser Ile Asn
                565                 570                 575

Ser Pro Arg Met Pro Lys Thr Gly Ser Arg Gln Asp Lys Asn Ile His
            580                 585                 590

Thr Lys Lys Glu Glu Arg Asn Pro Leu Asn Asn Ile His Asp Leu Ser
        595                 600                 605

Gln Leu Glu Asn Val Pro Asp Glu Met Asn Gln Met Phe Ser Pro Pro
    610                 615                 620

Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
                645                 650                 655

Arg Asn Asp Leu Pro Asp Thr Ser Pro Met Ser Ser Ile Gln Thr Ala
            660                 665                 670

Leu Pro Pro Ser Gln Leu Leu Thr Asp Gln Gly Phe Ala Asp Leu Asp
        675                 680                 685

Asn Phe Met Ser Ser Leu
        690

<210> SEQ ID NO 16
<211> LENGTH: 9
<212> TYPE: DNA
<213> ORGANISM: Artificial Sequence
<220> FEATURE:
<223> OTHER INFORMATION: synthetic promoter region sequence Haa1p
      transcription factor binding site
<220> FEATURE:
<221> NAME/KEY: modified_base
<222> LOCATION: (2)...(3)
<223> OTHER INFORMATION: n = g, a, c or t

<400> SEQUENCE: 16 gnnsmrgvg                                                              9

<210> SEQ ID NO 17
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant mut24,
      transcriptional activator

<400> SEQUENCE: 17

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
            20                  25                  30
```

```
Ile Lys Pro Lys Gly Arg Pro Ser Thr Thr Cys Asp Tyr Cys Lys Gln
             35                  40                  45

Leu Arg Lys Asn Lys Asn Ala Asn Pro Glu Gly Val Cys Thr Cys Gly
 50                  55                  60

Arg Leu Glu Lys Lys Leu Ala Gln Lys Ala Lys Glu Glu Ala Arg
 65                  70                  75                  80

Val Lys Ala Lys Glu Lys Gln Arg Lys Gln Cys Thr Cys Gly Thr Asp
             85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
            115                 120                 125

Phe Glu Arg Val Leu Ser Ser Thr Ser Leu Asp Ser Asn Met Leu Ser
            130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Leu Ser Ser Met Ser
            195                 200                 205

Phe Asn Phe Leu Thr Gly Asn Ile Asn Glu Thr Asn Gln Asn His Ser
            210                 215                 220

Asn His Gln His Ser Lys Ser Ser Asn Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
                260                 265                 270

Ile Ser Asn Ser Arg Val Gly Glu Val Ser Val Pro Leu Glu Glu Tyr
            275                 280                 285

Ile Pro Ser Asp Ile Asp Gly Val Gly Arg Val Thr Asp Lys Ser Ser
            290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
                340                 345                 350

Asn Gly Asn Gly Met Asn Asn Ser Asn Asn Asn Ile Asn Ser Asn
            355                 360                 365

Gly Asn Asp Lys Asn Asn Asn Ser Ser Arg Gln Glu His Gln Gly
            370                 375                 380

Asn Gly Leu Phe Asp Met Phe Thr Asp Ser Ser Ser Ile Ser Thr Leu
385                 390                 395                 400

Ser Arg Ala Asn Leu Leu Leu Gln Glu Lys Ile Gly Ser Gln Glu Asn
                405                 410                 415

Ser Val Lys Pro Glu Asn Tyr Ser Lys Asn Pro Gln Leu Arg His Gln
                420                 425                 430

Leu Thr Ser Arg Ser Arg Ser Phe Ile His His Pro Ala Asn Glu Tyr
            435                 440                 445

Leu Lys Asn Thr Phe Gly Asn Ser His Ser Asn Asp Ile Gly Lys Gly
```

```
                450                 455                 460
Val Glu Val Leu Ser Leu Thr Pro Ser Phe Met Asp Ile Pro Glu Lys
465                 470                 475                 480

Glu Arg Glu Thr Glu Arg Ser Pro Ser Ser Asn Tyr Ile Thr Asp Arg
                485                 490                 495

Pro Phe Thr Arg Lys Pro Arg Ser Ser Ser Ile Asp Val Asn His Arg
            500                 505                 510

Tyr Pro Pro Met Ala Pro Thr Thr Val Ala Thr Ser Pro Gly Ala Leu
        515                 520                 525

Asn Asn Ala Val Ala Ser Asn Leu Asp Asp Gln Leu Ser Leu Thr Ser
    530                 535                 540

Leu Asn Ser Gln Pro Ser Ser Ile Ala Asn Met Met Met Asp Pro Ser
545                 550                 555                 560

Asn Leu Ala Glu Gln Ser Ser Ile His Ser Val Pro Gln Ser Ile Asn
                565                 570                 575

Ser Pro Arg Met Pro Lys Thr Gly Ser Arg Gln Asp Lys Asn Ile His
            580                 585                 590

Thr Lys Lys Glu Glu Arg Asn Pro Leu Asn Asn Ile His Asp Leu Ser
        595                 600                 605

Gln Leu Glu Asn Val Pro Asp Glu Met Asn Gln Met Phe Ser Pro Pro
610                 615                 620

Leu Lys Ser Met Asn Arg Ala Asp Ala Ile Arg Glu Asn Ser Ser Ser
625                 630                 635                 640

Ser Asn Ile Ile Ile Gln Gly Asn Ser Met Ile Ser Thr Pro Ser Gly
                645                 650                 655

Arg Asn Asp Leu Pro Asp Thr Ser Pro Met Ser Ser Ile Gln Thr Ala
            660                 665                 670

Ser Pro Pro Ser Gln Leu Leu Thr Asn Gln Gly Phe Ala Asp Trp Asp
        675                 680                 685

Asn Phe Met Ser Ser Leu
    690

<210> SEQ ID NO 18
<211> LENGTH: 616
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant mut33,
      transcriptional activator

<400> SEQUENCE: 18

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
                20                  25                  30

Ile Lys Pro Lys Gly Arg Pro Ser Thr Thr Cys Asp Tyr Cys Lys Gln
        35                  40                  45

Leu Arg Lys Asn Lys Asn Ala Asn Pro Glu Gly Val Cys Thr Cys Gly
    50                  55                  60

Arg Leu Glu Lys Lys Leu Ala Gln Lys Lys Glu Glu Ala Arg
65                  70                  75                  80

Val Lys Ala Lys Glu Lys Gln Arg Lys Gln Cys Thr Cys Gly Thr Asp
                85                  90                  95

Glu Val Cys Lys Tyr His Ala Gln Lys Arg His Leu Arg Lys Ser Pro
```

```
                    100                 105                 110
        Ser Ser Ser Gln Lys Lys Gly Arg Ser Ile Ser Arg Ser Gln Pro Met
                        115                 120                 125
        Phe Glu Arg Val Leu Ser Ser Thr Ser Leu Asp Ser Asn Met Leu Ser
            130                 135                 140
        Gly His Gly Ala Leu Ser Asp Thr Ser Ser Ile Leu Thr Ser Thr Phe
        145                 150                 155                 160
        Leu Asp Ser Glu Pro Gly Val Gly Lys Ile Ser Lys Asp Tyr His His
                        165                 170                 175
        Val Pro Ser Leu Ala Ser Ile Ser Ser Leu Gln Ser Ser Gln Ser Leu
                    180                 185                 190
        Asp Gln Asn Phe Ser Val Pro Gln Ser Pro Pro Leu Ser Ser Met Ser
                    195                 200                 205
        Phe Asn Phe Leu Thr Gly Asn Ile Asn Glu Thr Asn Gln Asn His Ser
            210                 215                 220
        Asn His Gln His Ser Lys Ser Ser Asn Asn Trp Gln Asp Ser Ser Val
        225                 230                 235                 240
        Ser Leu Pro Ala Lys Ala Asp Ser Arg Leu Asn Met Met Asp Lys Asn
                        245                 250                 255
        Asn Ser Val Gly Leu Asp Leu Leu Gly His Ser Lys Arg Ile Ser Pro
                    260                 265                 270
        Ile Ser Asn Ser Arg Val Gly Glu Val Ser Val Pro Leu Glu Glu Tyr
                275                 280                 285
        Ile Pro Ser Asp Ile Asp Gly Val Gly Arg Val Thr Asp Lys Ser Ser
                290                 295                 300
        Leu Val Tyr Asp Trp Pro Phe Asp Glu Ser Ile Glu Arg Asn Phe Ser
        305                 310                 315                 320
        Thr Thr Ala Thr Ala Ala Thr Gly Glu Ser Lys Phe Asp Ile Asn Asp
                        325                 330                 335
        Asn Cys Asn Arg Ile Asn Ser Lys Ser Tyr Ser Lys Thr Asn Ser Met
                    340                 345                 350
        Asn Gly Asn Gly Met Asn Asn Ser Asn Asn Asn Ile Asn Ser Asn
                    355                 360                 365
        Gly Asn Asp Lys Asn Asn Asn Ser Ser Arg Gln Glu His Gln Gly
            370                 375                 380
        Asn Gly Leu Phe Asp Met Phe Thr Asp Ser Ser Ser Ile Ser Thr Leu
        385                 390                 395                 400
        Ser Arg Ala Asn Leu Leu Leu Gln Glu Lys Ile Gly Ser Gln Glu Asn
                        405                 410                 415
        Ser Val Lys Pro Glu Asn Tyr Ser Lys Asn Pro Gln Leu Arg His Gln
                    420                 425                 430
        Leu Thr Ser Arg Ser Arg Ser Phe Ile His His Pro Ala Asn Glu Tyr
                    435                 440                 445
        Leu Lys Asn Thr Phe Gly Asn Ser His Ser Asn Val Ile Gly Lys Gly
                    450                 455                 460
        Val Glu Val Leu Ser Leu Thr Pro Ser Phe Met Asp Ile Pro Glu Lys
        465                 470                 475                 480
        Glu Arg Glu Thr Glu Arg Ser Pro Ser Asn Tyr Ile Thr Asp Arg
                        485                 490                 495
        Pro Phe Thr Arg Lys Pro Arg Ser Ser Ser Ile Asp Val Asn His Arg
                    500                 505                 510
        Tyr Pro Pro Met Ala Pro Thr Thr Val Ala Thr Ser Pro Gly Ala Leu
                    515                 520                 525
```

```
Asn Asn Ala Val Ala Ser Asn Leu Asp Asp Gln Leu Ser Leu Thr Ser
            530                 535                 540

Leu Asn Ser Gln Pro Ser Ser Ile Ala Asn Met Met Met Asp Pro Ser
545                 550                 555                 560

Asn Leu Ala Glu Gln Ser Ser Ile His Ser Val Pro Gln Ser Ile Asn
                565                 570                 575

Ser Pro Arg Met Pro Lys Thr Gly Ser Arg Gln Asp Lys Asn Ile His
            580                 585                 590

Thr Lys Lys Glu Glu Arg Asn Pro Leu Asn Asn Ile His Asp Leu Ser
        595                 600                 605

Gln Leu Glu Met Tyr Gln Thr Arg
    610                 615

<210> SEQ ID NO 19
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant mut36,
      transcriptional activator

<400> SEQUENCE: 19

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
                20                  25                  30

Ile Lys Pro Lys Gly Arg Pro Ser Thr Thr Cys Asp Tyr Cys Lys Gln
            35                  40                  45

Leu Arg Lys Asn Lys Asn Ala Asn Pro Glu Gly Val Cys Thr Cys Gly
    50                  55                  60

Arg Leu Glu Lys Lys Leu Ala Gln Lys Ala Lys Glu Glu Ala Arg
65                  70                  75                  80

Val Lys Ala Lys Glu Lys Gln Arg Lys Gln Cys Thr Cys Gly Thr Asp
                85                  90                  95

Glu Val Cys Lys Tyr His Ala Gln Lys Arg His Leu Arg Lys Ser Pro
                100                 105                 110

Ser Ser Ser Gln Lys Lys Gly Arg Ser Ile Ser Arg Ser Gln Pro Met
            115                 120                 125

Phe Glu Arg Val Leu Ser Ser Thr Ser Leu Asp Ser Asn Met Leu Ser
130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Pro Leu Ser Ser Met Ser
        195                 200                 205

Phe Asn Phe Leu Thr Gly Asn Ile Asn Glu Thr Asn Gln Asn His Ser
210                 215                 220

Asn His Gln His Ser Lys Ser Ser Asn Asn Trp Gln Asp Ser Ser Val
225                 230                 235                 240

Ser Leu Pro Ala Lys Ala Asp Ser Arg Leu Asn Met Met Asp Lys Asn
                245                 250                 255
```

-continued

```
Asn Ser Val Gly Leu Asp Leu Gly His Ser Lys Arg Ile Ser Pro
            260                 265                 270
Ile Ser Asn Ser Arg Val Gly Glu Val Ser Val Pro Leu Glu Glu Tyr
        275                 280                 285
Ile Pro Ser Asp Ile Asp Gly Val Gly Arg Val Thr Asp Lys Ser Ser
    290                 295                 300
Leu Val Tyr Asp Trp Pro Phe Asp Glu Ser Ile Glu Arg Asn Phe Ser
305                 310                 315                 320
Thr Thr Ala Thr Ala Ala Thr Gly Glu Ser Lys Phe Asp Ile Asn Asp
                325                 330                 335
Asn Cys Asn Arg Ile Asn Ser Lys Ser Tyr Ser Lys Thr Asn Ser Met
            340                 345                 350
Asn Gly Asn Gly Met Asn Asn Ser Asn Asn Asn Ile Asn Ser Asn
        355                 360                 365
Gly Asn Asp Lys Asn Asn Asn Ser Ser Arg Gln Glu His Gln Gly
    370                 375                 380
Asn Gly Leu Phe Asp Met Phe Thr Asp Ser Ser Ser Ile Ser Thr Leu
385                 390                 395                 400
Ser Arg Ala Asn Leu Leu Gln Glu Lys Ile Gly Ser Gln Asp Asn
                405                 410                 415
Ser Val Lys Pro Glu Asn Tyr Ser Lys Asn Pro Gln Leu Arg His Gln
            420                 425                 430
Leu Thr Ser Arg Ser Arg Ser Ser Ile His His Pro Ala Asn Glu Tyr
        435                 440                 445
Leu Lys Asn Thr Phe Gly Asn Ser His Ser Asn Asp Ile Gly Lys Gly
    450                 455                 460
Val Glu Val Leu Ser Leu Thr Pro Ser Phe Met Asp Ile Pro Glu Lys
465                 470                 475                 480
Glu Arg Glu Thr Glu Arg Ser Pro Ser Ser Asn Tyr Ile Thr Asp Arg
                485                 490                 495
Pro Phe Thr Arg Lys Pro Arg Ser Ser Ser Phe Asp Val Asn His Arg
            500                 505                 510
Tyr Pro Pro Met Ala Pro Thr Thr Val Ala Thr Ser Pro Gly Ala Leu
        515                 520                 525
Asn Asn Ala Val Ala Ser Asn Leu Asp Asp Gln Leu Ser Leu Thr Ser
    530                 535                 540
Leu Asn Ser Gln Pro Ser Ser Ile Ala Asn Met Met Met Asp Pro Ser
545                 550                 555                 560
Asn Leu Ala Glu Gln Ser Ser Ile His Ser Val Pro Gln Ser Ile Asn
                565                 570                 575
Ser Pro Arg Met Pro Lys Thr Gly Ser Arg Gln Asp Lys Asn Ile His
            580                 585                 590
Thr Lys Lys Glu Glu Arg Asn Pro Leu Asn Asn Ile His Asp Leu Ser
        595                 600                 605
Gln Leu Glu Asn Val Pro Asp Glu Met Asn Gln Met Phe Ser Pro Pro
    610                 615                 620
Leu Lys Ser Met Asn Arg Pro Asp Ala Ile Arg Glu Asn Ser Ser Ser
625                 630                 635                 640
Ser Asn Phe Ile Ile Gln Gly Asn Ser Met Ile Ser Thr Pro Ser Gly
                645                 650                 655
Arg Asn Asp Leu Pro Asp Thr Ser Pro Met Ser Ser Ile Gln Thr Ala
            660                 665                 670
```

Ser Pro Pro Ser Gln Leu Leu Thr Val Gln Gly Phe Ala Asp Leu Asp
            675                 680                 685

Asn Phe Met Ser Ser Leu
    690

<210> SEQ ID NO 20
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3
      promoter DNA-binding transcription factor Haa1p
      site-directed acetate resistant mutant mut5,
      transcriptional activator

<400> SEQUENCE: 20

Met Val Leu Ile Asn Gly Ile Lys Tyr Ala Cys Glu Arg Cys Ile Arg
 1               5                  10                  15

Gly His Arg Val Thr Thr Cys Asn His Thr Asp Gln Pro Leu Met Met
             20                  25                  30

Ile Lys Pro Lys Gly Arg Pro Ser Thr Thr Cys Asp Tyr Cys Lys Gln
         35                  40                  45

Leu Arg Lys Asn Lys Asn Ala Asn Pro Glu Gly Val Cys Thr Cys Gly
 50                  55                  60

Arg Leu Glu Lys Lys Lys Leu Ala Gln Lys Ala Lys Glu Glu Ala Arg
 65                  70                  75                  80

Val Lys Ala Lys Glu Lys Gln Arg Lys Gln Cys Thr Cys Gly Thr Asp
             85                  90                  95

Glu Val Cys Lys Tyr His Ala Gln Lys Arg His Leu Arg Lys Ser Pro
        100                 105                 110

Ser Ser Ser Gln Lys Lys Gly Arg Ser Ile Ser Arg Ser Gln Pro Met
        115                 120                 125

Phe Glu Arg Val Leu Ser Ser Thr Ser Leu Asp Ser Asn Met Leu Ser
130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Tyr His His
                165                 170                 175

Val Pro Ser Leu Ala Ser Ile Ser Ser Leu Gln Ser Ser Gln Ser Leu
            180                 185                 190

Asp Gln Asn Phe Ser Val Pro Gln Ser Pro Leu Ser Ser Met Ser
        195                 200                 205

Phe Asn Phe Leu Thr Gly Asn Ile Asn Glu Thr Asn Gln Asn His Ser
210                 215                 220

Asn His Gln His Ser Lys Ser Ser Asn Asn Trp Gln Asp Ser Ser Val
225                 230                 235                 240

Ser Leu Pro Ala Lys Ala Asp Ser Arg Leu Asn Met Met Asp Lys Asn
            245                 250                 255

Asn Ser Val Gly Leu Asp Leu Leu Gly His Ser Lys Arg Ile Ser Pro
        260                 265                 270

Ile Ser Asn Ser Arg Val Gly Glu Val Ser Val Pro Leu Glu Glu Tyr
        275                 280                 285

Ile Pro Ser Asp Ile Asp Gly Val Gly Arg Val Thr Asp Lys Ser Ser
        290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
            325                 330                 335

Asn Cys Asn Arg Ile Asn Ser Lys Ser Tyr Ser Lys Thr Asn Ser Met
            340                 345                 350

Asn Gly Asn Gly Met Asn Asn Ser Asn Asn Asn Ile Asn Ser Asn
        355                 360                 365

Gly Asn Asp Lys Asn Asn Asn Ser Ser Arg Gln Glu His Gln Gly
370                 375                 380

Asn Gly Leu Phe Asp Met Phe Thr Asp Ser Ser Ile Ser Thr Leu
385                 390                 395                 400

Ser Arg Ala Asn Leu Leu Leu Gln Glu Lys Ile Gly Ser Gln Glu Asn
            405                 410                 415

Ser Val Lys Pro Glu Asn Tyr Ser Lys Asn Pro Gln Leu Arg His Gln
            420                 425                 430

Leu Thr Ser Arg Ser Arg Ser Phe Ile His His Pro Ala Asn Glu Tyr
            435                 440                 445

Leu Lys Asn Thr Phe Gly Asn Ser His Ser Asn Asp Ile Gly Lys Gly
            450                 455                 460

Val Glu Val Leu Ser Leu Thr Leu Ser Phe Met Asp Ile Pro Glu Lys
465                 470                 475                 480

Glu Arg Glu Thr Glu Arg Ser Pro Ser Ser Asn Tyr Ile Thr Asp Arg
            485                 490                 495

Pro Phe Thr Arg Lys Pro Arg Ser Ser Ser Ile Asp Val Asn His Arg
            500                 505                 510

Tyr Pro Pro Met Ala Pro Thr Thr Val Ala Thr Ser Pro Gly Ala Leu
            515                 520                 525

Asn Asn Ala Val Ala Ser Asn Leu Asp Asp Gln Leu Ser Leu Thr Ser
            530                 535                 540

Leu Asn Ser Gln Pro Ser Ser Ile Ala Asn Met Met Met Gly Pro Ser
545                 550                 555                 560

Asn Leu Ala Glu Gln Ser Ser Ile His Ser Val Pro Gln Ser Ile Asn
            565                 570                 575

Ser Pro Arg Met Pro Lys Thr Gly Ser Arg Gln Asp Lys Asn Ile His
            580                 585                 590

Thr Lys Lys Glu Glu Arg Asn Pro Leu Asn Asn Ile His Asp Leu Ser
            595                 600                 605

Gln Leu Glu Asn Val Pro Asp Glu Met Asn Gln Met Phe Ser Pro Pro
            610                 615                 620

Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
            645                 650                 655

Arg Asn Asp Leu Pro Asp Thr Ser Pro Met Ser Asn Ile Gln Thr Ala
            660                 665                 670

Ser Pro Pro Ser Gln Leu Leu Thr Asp Gln Gly Phe Ala Asp Leu Asp
            675                 680                 685

Asn Phe Met Ser Ser Leu
    690

<210> SEQ ID NO 21
<211> LENGTH: 694
<212> TYPE: PRT
<213> ORGANISM: Artificial Sequence
<220> FEATURE:
<223> OTHER INFORMATION: synthetic Saccharomyces cerevisiae strain TR3 promoter DNA-binding transcription factor Haa1p
consensus sequence, transcriptional activator

<400> SEQUENCE: 21

```
Met Val Leu Ile Asn Gly Ile Lys Tyr Ala Cys Glu Arg Cys Ile Arg
  1               5                  10                  15

Gly His Arg Val Thr Thr Cys Asn His Thr Asp Gln Pro Leu Met Met
             20                  25                  30

Ile Lys Pro Lys Gly Arg Pro Ser Thr Thr Cys Asp Tyr Cys Lys Gln
         35                  40                  45

Leu Arg Lys Asn Lys Asn Ala Asn Pro Glu Gly Val Cys Thr Cys Gly
     50                  55                  60

Arg Leu Glu Lys Lys Lys Leu Ala Gln Lys Ala Lys Glu Glu Ala Arg
 65                  70                  75                  80

Val Lys Ala Lys Glu Lys Gln Arg Lys Gln Cys Thr Cys Gly Thr Asp
                 85                  90                  95

Glu Val Cys Lys Tyr His Ala Gln Lys Arg His Leu Arg Lys Ser Pro
                100                 105                 110

Ser Ser Ser Gln Lys Lys Gly Arg Ser Ile Ser Arg Ser Gln Pro Met
            115                 120                 125

Phe Glu Arg Val Leu Ser Ser Thr Ser Leu Asp Ser Asn Met Leu Ser
130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
                180                 185                 190

Asp Gln Asn Phe Ser Val Pro Gln Ser Pro Leu Ser Ser Met Ser
            195                 200                 205

Phe Asn Phe Leu Thr Gly Asn Ile Asn Glu Thr Asn Gln Asn His Ser
210                 215                 220

Asn His Gln His Ser Lys Ser Ser Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
                260                 265                 270

Ile Ser Asn Ser Arg Val Gly Glu Val Ser Val Pro Leu Glu Glu Tyr
            275                 280                 285

Ile Pro Ser Asp Ile Asp Gly Val Gly Arg Val Thr Asp Lys Ser Ser
        290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
                340                 345                 350

Asn Gly Asn Gly Met Asn Ser Asn Asn Asn Ile Asn Ser Asn
            355                 360                 365

Gly Asn Asp Lys Asn Asn Asn Ser Ser Arg Gln Glu His Gln Gly
        370                 375                 380

Asn Gly Leu Phe Asp Met Phe Thr Asp Ser Ser Ser Ile Ser Thr Leu
385                 390                 395                 400
```

-continued

```
Ser Arg Ala Asn Leu Leu Gln Glu Lys Ile Gly Ser Gln Glu Asn
            405                 410                 415
Ser Val Lys Pro Glu Asn Tyr Ser Lys Asn Pro Gln Leu Arg His Gln
        420                 425                 430
Leu Thr Ser Arg Ser Arg Ser Phe Ile His His Pro Ala Asn Glu Tyr
        435                 440                 445
Leu Lys Asn Thr Phe Gly Asn Ser His Ser Asn Asp Ile Gly Lys Gly
    450                 455                 460
Val Glu Val Leu Ser Leu Thr Pro Ser Phe Met Asp Ile Pro Glu Lys
465                 470                 475                 480
Glu Arg Glu Thr Glu Arg Ser Pro Ser Ser Asn Tyr Ile Thr Asp Arg
            485                 490                 495
Pro Phe Thr Arg Lys Pro Arg Ser Ser Ser Ile Asp Val Asn His Arg
            500                 505                 510
Tyr Pro Pro Met Ala Pro Thr Thr Val Ala Thr Ser Pro Gly Ala Leu
        515                 520                 525
Asn Asn Ala Val Ala Ser Asn Leu Asp Asp Gln Leu Ser Leu Thr Ser
    530                 535                 540
Leu Asn Ser Gln Pro Ser Ser Ile Ala Asn Met Met Met Asp Pro Ser
545                 550                 555                 560
Asn Leu Ala Glu Gln Ser Ser Ile His Ser Val Pro Gln Ser Ile Asn
            565                 570                 575
Ser Pro Arg Met Pro Lys Thr Gly Ser Arg Gln Asp Lys Asn Ile His
            580                 585                 590
Thr Lys Lys Glu Glu Arg Asn Pro Leu Asn Asn Ile His Asp Leu Ser
        595                 600                 605
Gln Leu Glu Asn Val Pro Asp Glu Met Asn Gln Met Phe Ser Pro Pro
    610                 615                 620
Leu Lys Ser Met Asn Arg Pro Asp Ala Ile Arg Glu Asn Ser Ser Ser
625                 630                 635                 640
Ser Asn Phe Ile Ile Gln Gly Asn Ser Met Ile Ser Thr Pro Ser Gly
            645                 650                 655
Arg Asn Asp Leu Pro Asp Thr Ser Pro Met Ser Ser Ile Gln Thr Ala
            660                 665                 670
Ser Pro Pro Ser Gln Leu Leu Thr Asp Gln Gly Phe Ala Asp Leu Asp
        675                 680                 685
Asn Phe Met Ser Ser Leu
        690
```